(12) United States Patent
Homan et al.

(10) Patent No.: US 7,566,447 B2
(45) Date of Patent: Jul. 28, 2009

(54) BIOCIDES

(75) Inventors: Jane Homan, Hillpoint, WI (US);
Michael Imboden, Madison, WI (US);
Michael Riggs, Tucson, AZ (US);
Stephane Carryn, Brussels (BE);
Deborah A. Schaefer, Tuscon, AZ (US)

(73) Assignees: Iogenetics, LLC, Madison, WI (US);
The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 11/254,500

(22) Filed: Oct. 20, 2005

(65) Prior Publication Data

US 2006/0147442 A1 Jul. 6, 2006

Related U.S. Application Data

(63) Continuation-in-part of application No. 10/844,837, filed on May 13, 2004.

(60) Provisional application No. 60/470,841, filed on May 15, 2003, provisional application No. 60/620,642, filed on Oct. 20, 2004.

(51) Int. Cl.
*A61K 38/43* (2006.01)
*A61L 9/01* (2006.01)
*C07K 14/00* (2006.01)
*C07K 17/00* (2006.01)
*C07K 1/00* (2006.01)
*C12P 21/08* (2006.01)
*C07K 16/00* (2006.01)
*C11D 3/386* (2006.01)
*C12S 11/00* (2006.01)

(52) U.S. Cl. ............... 424/94.1; 424/76.8; 530/350; 530/388.6; 930/240; 510/305

(58) Field of Classification Search .............. None
See application file for complete search history.

(56) References Cited

U.S. PATENT DOCUMENTS

| 4,816,567 A | | 3/1989 | Cabilly |
| 5,019,411 A | * | 5/1991 | Johnson et al. ............. 426/52 |
| 5,433,955 A | | 7/1995 | Bredehorst et al. |
| 5,550,145 A | | 8/1996 | Olund et al. |
| 5,601,825 A | | 2/1997 | Hansen et al. |
| 5,618,840 A | | 4/1997 | Wright |
| 5,750,496 A | * | 5/1998 | Forney et al. .............. 514/2 |
| 5,871,714 A | | 2/1999 | Budny et al. |
| 5,874,079 A | * | 2/1999 | Weinrauch et al. ........ 424/94.6 |
| 5,891,490 A | | 4/1999 | Merabet |
| 6,013,918 A | | 1/2000 | Bushnell et al. |
| 6,015,882 A | * | 1/2000 | Petersen et al. ............ 530/350 |
| 6,063,905 A | | 5/2000 | Capra et al. |
| 6,086,936 A | | 7/2000 | Wilson et al. |
| 6,103,505 A | * | 8/2000 | Clausen et al. ............. 435/134 |
| 6,110,463 A | * | 8/2000 | Riggs et al. ............. 424/151.1 |
| 6,159,447 A | | 12/2000 | Budny et al. |
| 6,165,526 A | | 12/2000 | Newman |
| 6,172,040 B1 | * | 1/2001 | Naidu ..................... 514/6 |
| 6,265,187 B1 | | 7/2001 | Scott et al. |
| 6,323,020 B1 | * | 11/2001 | Perryman et al. ........ 435/252.3 |
| 6,376,450 B1 | * | 4/2002 | Ghosh et al. ............. 510/392 |
| 6,475,484 B1 | * | 11/2002 | Weiss et al. ............. 424/94.6 |
| 6,562,617 B1 | | 5/2003 | Anderson et al. |
| 6,830,745 B1 | | 12/2004 | Budny et al. |
| 6,984,503 B1 | | 1/2006 | Wang et al. |
| 7,063,837 B2 | | 6/2006 | Fischetti et al. |
| 2002/0015697 A1 | * | 2/2002 | Beckman et al. ........... 424/94.4 |
| 2002/0048576 A1 | * | 4/2002 | Anderson et al. ........ 424/94.63 |
| 2003/0114377 A1 | | 6/2003 | Kirkland et al. |
| 2004/0009167 A1 | | 1/2004 | Rider |
| 2004/0052814 A1 | | 3/2004 | Shi et al. |
| 2004/0115207 A1 | | 6/2004 | Irwin et al. |
| 2005/0014932 A1 | | 1/2005 | Imboden |
| 2005/0170334 A1 | | 8/2005 | Mikayama et al. |

FOREIGN PATENT DOCUMENTS

WO 00/23593 4/2000

OTHER PUBLICATIONS

Rehg et al. Effect of Interferon-gamma in experimental *C.parvum* infection. Jorunal of Infectious diseases, 1996; 174:229-32.*
Schaefer et al. Infection and Immunity, May 2000, p. 2608-2616.*
Hunt et al. Pediatric Research, Mar. 2002, vol. 51 p. 370-376.*
Riggs et al. Animicrobial Agents and Chemotherapy, Feb. 2002, p. 275-282.*
Searcy et al. Applied and Environmental Microbiology, Sep. 2006, p. 6242-6247.*
Carey et al. Water Research, 2004, 38:818-862.*
Howe et al. Emerging Infectious Diseases, 2002, 8:619-624.*
Definition of Kitchenware -Merriam-Webster Online Dictionary.*
Kato et al. J. Parasitol 88(4), 2002 pp. 718-722.*

(Continued)

*Primary Examiner*—Robert B Mondesi
*Assistant Examiner*—Oluwatosin Ogunbiyi
(74) *Attorney, Agent, or Firm*—Casimir Jones, S.C.

(57) ABSTRACT

The present invention relates to the use of biocide (e.g., bactericidal enzyme) to target pathogens. In particular, the present invention provides biocides for use in health care (e.g., human and veterinary), agriculture (e.g., animal and plant production), and food processing (e.g., water purification).

5 Claims, 23 Drawing Sheets

OTHER PUBLICATIONS

Sitaram et al. Current Drug Targets 2002 vol. 3 pp. 259-267.*
Saito et al. J Dairy Sci vol. 74 pp. 3724-3730.*
Yoshida et al. J Dairy Sci vol. 83 pp. 2211-2215.*
Definition of Treatment—American Heritage Dictionary of the English Language: 4$^{th}$ edition. 2000 -Online.*
Jenkins. Vetrinary Parasitology 101 (2001) p. 291-310.*
Graczyk et al. Applied and Environmental Microbiology Jul. 1998 p. 2736-2738.*
Garcia et al. Diagnostic Medical Parasitology 2$^{nd}$ edition 1993 p. 49-51.*
Carryn et al. International Journal of Antimicrobial Agents vol. 24S (2004) p. S117.*
Freshney (Culture of Animal Cells, A Manual of Basic Technique, Alan R. Liss, Inc., 1983, New York, p. 4).*
Carryn et al. International Journal of Antimicrobial Agents vol. 24S (2004) p. S117.*
Prins et al. Antonie van Leeuwenhoek, vol. 49, p. 585-595, 1983.*
Foye's Principles of Medicinal Chemistry, Fifth Edition, D.A. Williams and T.L. Lemke, editors, Lippincott Williams and Wilkins, Philadelphia, 2002, 5th edition, Chapter 6, p. 119, left column under Alternative Drug Delivery Methods for Peptides and Proteins.*
definition of treatment. American Heritage Dictionary. http://www.bartleby.com/61/43/T0334300. retrieved Oct. 24, 2006.*
Freshney, R. Ian: A Manual of Basic Technique. Chapter 4: Culture of Animal Cells, Alan R. Liss, Inc., 1983, New York.*
Cohen, S. "Colorado Firm Recalls Beef Trim And Ground Beef Products For Possible *E. coli* O157:H7" Recall Release, FSIS-RC-055-2002.
Buzby et al., "Bacterial Foodborne Disease: Medical Costs and Productivity Losses" 1996. Food and Consumer Economics Division, Economic Research Service U.S. Department of Agriculture, Economic Report No. 741.
During,K., et al., "The non-enzymatic microbicidal activity of lysozymes", FEBS Lett., 449(2-3):93-100 (1999).
H.D. Kusumaningrum, G. Intl J Food Microbial. Survival of Foodborne pathogens on stainless steem surfaces and Cross contamination. Aug. 25;85(3):227-36 [2003].
Reusens-Billen, et al., "Prevention of the cytotoxic effect of IL-1 by human lysozyme on isolated rat islets", Diabetes Res. Clin. Pract., 23(2):85-94(1994).
Takada, K., et al., "Binding of Lysozyme to Lipopolysaccharide Supresses Tumor Necrosis Factor Production In Vivo", Infect. Immun., 62(4):1171-1175 (1994).
Takada, K., et al., "Lysozyme Regulates LPS-Induced Interleuken-6 Release in Mice", Circ. Shock, 44(4):169-174 (1994).
Qu, X.D. and Lehrer,R.I. 'Secretory Phospholipase A2 is the Principal Bactericide for *Staphylococci* and other Gram-Positive Bacteria in Human Tears', Infect. Immun., 66:2791-2797 (1998).
Qu, X.D., et al., "Secretion of Type II Phospholipase A2 and Cryptdin by Rat Small Intestinal Paneth Cells", Infect. Immun., 64:5161-5165 (1996).
Buckland, A.G. and Wilton, D.C., "The antibacterial properties of secreted phospholipases A2", Biochim. Biophys. Acta, 1488(1-2):71-82 (2000).
Grönroos, J.O., et al., "Bactericidal Group IIA Phospholipase A2 in Serum of Patients with Bacterial Infections", J. Infect. Dis., 185:1767-1772 (2002).
Laine, V.J., et al., "Resistance of Transgenic Mice Expressing Human Group II Phospholipase A2 to *Escheria coli* Infection", Infect. Immun., 68(1):87-92 (2000).
Koduri, R.S., et al., "Action of Human Group IIa Secreted Phospholipase A2 on Cell Membranes", J. Biol. Chem., 273:32142-31153 (1998).
Laine, V.J., et al., "Protection of Group II Phospholipase A2 Against *Staphyloccus aureus*", J. Immunol., 162:7402-7408 (1999).
Okhuysen, P.C., et al., "*Cryptosporidium parvum* Metalloaminopeptidase Inhibitors Prevent In Vitro Excystation", Antimicrob. Agents Chemother., 40:2781-2784 (1996).
Forney, J.R., et al., "Efficacy of Serine Protease Inhibitors Against *Cryptospordium parvum* infection in a Bovine Fallopian Tube Epithelial Cell Culture", J. Parasitol., 82(4) 638-640 (1996).
Forney, J.R., et al., "A Role for Host Phosphoinositide 3-Kinase and Cytoskeletal Remodeling during *Cryptosporidium parvum* Infection", Infect. Immun., 67(2) 844-852 (1999).
Nesterenko, M.V., et al., "A metallo-dependent cysteine proteinase of *Cryptosporidium parvum* associated with the surface of sporozoites", Microbios., 83:77-88 (1995).
Mannion, B.A., et al., "Separation of Sublethal and Lethal Effects of the Bactericidal/Permeability Increasing Protein on *Escheria coli*",J. Clin. Invest., 85(3):853-860 (1990).
Prohinar, P., et al., "OmpR-dependent and OmpR-independent responses of *Escheria coli* to sublethal attack by the neutrophil bactericidal/permeability increasing protein", Mol. Microbiol., 43(6):1493-1504 (2002).
Selsted et al., "Purification and Antibacterial Activity of Antimicrobial Peptides if Rabbit Granulocytes", Infect. Immun., 45:150-154 (1984).
Zeya et al., "Antimicrobial Specificity of Leukocyte Lysosomal Cationic Proteins," Science, 154:1049 1051 [1966].
Zeya et al., "Characertization of Cationic Protein-Bearing Granules of Polymorphonuclear Leukocytes," Lab. Invest., 24:229 236 [1971].
Lehrer, et al., "Direct Inactivation of Viruses by MCP-1 and MCP-2, Natural Peptide Antibiotics from Rabbit Leukocytes", J. Virol. 54(2) pp. 467-472 (1985).
Selsted et al., "Activity of Rabbit Leukocyte Peptieds Against *Candida albicans*", Infect. Immun., 49:202-206 (1985).
Segal, et al., "In Vitro Effect of Phagocyte Cationic Peptides on *Coccidioides immitis*", J.Infect.Disease, 151:890-894 (1985).
Tzipori, S., Adv. Parasitol., 40:187-221 [1998].
Costerton et al., "Microbial Biofilms", Annu Rev Microbiol; 49:711-45(1995).
Lehrer, et al., "Nonoxidative Fungicidal Mechanisms of Mammalian Granulocytes: Demonstration of Components with Candidacidal Activity in Human, Rabbit . . . ", Infect. & Immun.
Tomkin, et al. "Guidelines to Prevent Post-Processing Contamination from Listeria monocytogenes", Dairy, Food Environ Sanit; 19:551-62 (1999).
Welbourn and Williams "New Listeria Control Measures Under Consideration", Dairy, Food Environ Sanit ; 19:399-401(1999).
Tuttle, J., et al., "Lessons from a large outbreak of *Escheria coli* 0157:H7 infections: insights into the infectious dose and method of widespread contamination of hamburger patties", Epidemiol. Infect., 122:185-192 (1999).
Beumer, et al., "Listeria species in domestic environments", Epidemiol Infect. ;117(3):437-42 Dec. (1996).
Zichichi, et al., "Pseudomonas *aeruginosa folliculitis* after shower/bath exposure", Int J Dermatol. 39(4):270-3 Apr. (2000).
Kumar, C.G. and Anand, S.K. "Significance of microbial biofilms in food industry: a review", Int J Food Microbiol; 42:9-27 (1998).
Zottola and Sasahara, "Microbial biofilms in the fodd processing industry-Should they be a concern?", Int J Food Microbiol; 23:125-48 (1994).
Mattick et al., "The survival of foodborne pathogens during domestic washing-up and subsequent transfer onto washing-up sponges, kitchen surfaces and food", Int J Food Microbiol. 25;85(3):213-26 (2003).
Kusumaningrum et al., "Survival of foodborne pathogens on stainless steel surfaces and cross-contamination to foods", Int J Food Microbiol. 85(3):227-36 (2003).
Silverman and Nieland, "Hot tub Dermatitis: A familial outbreak of *Pseudomonas folliculitis*", J Am Acad Dermatol.; 8(2) pp. 153-Feb. 6 (1983).
Murphy et al., "Defensins Are Mitogenic for Epithelial Cells and Fibroblasts", J Cell. Physiol., 155:408-13 (1993).
Blackman and Frank, "Growth of Listeria monocytogenes as a Biofilm on Various Food-Processing Surfaces", J Food Prot; 59:827-31 (1996).
Frank and Koffi, "Surface-adherent Growth of Listeria Monocytogenes is Associated with Increased Resistance to Surfactant Sanitizers and Heat", J Food Prot; 53:550-4 (1990).
Krysinski, "Effect of Cleaners and Sanitizers on Listeria monocytogenes Attached to Product Contact Surfaces", J Food Prot ; 55:246-51 (1992).

Ronner and Wong "Biofilm Development and Sanitizer Inactivation of Listeria monocytogenes and *Salmonella typhimurium* on Stainless Steel and . . . ", J Food Prot; 56:750-8 (1993).

Dunsmore, et al., "Design and Performance of Systems for Cleaning Product-Contact Surfaces of Food Equipment: A Review", J Food Prot; 44:220-40(1981).

Helke and Wong, "Survuval and Growth Characteristics of *Listeria monocytogenes* and *Salmonella typhimurium* on Stainless Steel and Buna-N Rubber", J Food Prot ; 57:963-8(1994).

Lehrer and Ladra "Fungicidal Components of Mammalian Granulocytes Active against *Cryptococcus neoformans*", J. Infect. Dis. 136(1) pp. 96-9 (1977).

McGwire, B.S., Olson, C.L., Tack, B.F. and Engman, D.M. (2003) Killing of African trypanosomes by antimicrobial peptides. J. Infect. Dis. 188, 146-152.

Forney, J.R., et al., "Antagonistic Effect of Human Alpha-1Antitrypsin on Excystation of *Cryptosporidium parvum* Oocysts", J. Parasitol., 83:771-774 (1997).

U.S. Dept. Ag. "Dairy Heifer Morbidity, Mortality, and Health Management Focusing on Preweaned Heifers", pp. 1-22 (1994).

Novello, A. "High Prevalence of Chlamydial and Gonococcal Infection in Women entering Jails and Juvenile Detention Centers"MMWR Morb. Mortal. Wkly. Rep., 48(36):803-805 (1999).

National Dairy Heifer Evaluation Project, USDA APHIS NAHMS [1994].

Grau, F., "Prevention of Microbial contamination in the export of beef abattoir", In: Smulders FJM ed. Amsterdam: Elsevier, 221-234 (1987)..

Thomas, et al., "Prevention of Microbial Contamination in the poultry processing plant", Smulders FJM ed. Amsterdan: Elsevier, 1987:163-180.

Perryman, L.E., et al., "Protection of claves against cryptosporidiosis with immune bovine colostrum induced by a *Cryptosporidium parvum* recombinant protein", Vaccine, 17:2142-2149 (1999).

Pritchard, G.C., et al., "Verocytotoxin-producing *Escheria coli* 0157 on a farm open to the public: outbreak investigation and longitudinal bacteriological study," Vet. Rec., 147:259-264 (2000).

Characklis, W.G. "Biofilm processes", In: Characklis WG and Marshall KC eds. New York: John Wiley & Sons, pp. 195-231(1990).

Kim, C.W., "Cryptosporidiosis in Pigs and Horses", In: J.P. Dubey, C.A. Speer, and R. Fayer eds. Boca Raton, FL: CRC Press, pp. 105-111 (1990).

Chappell, C., et al., "Infectivity of *Crypotosporidium parvum* in Healthy Adults With Preexisting Anti-C. Parvum Serum Immunoglobulin G", Am J. Trop. Med Hyg., 60(1), pp. 157-164 (1999).

Eisenhauer, P., et al., "Purification And Antimicrobial Properties Of Three Defensins From Rat Neutrophils", Infect. and Immun., 57(7) pp. 2021-2027 (1989).

Fore, J., "The effects of business practices, licensing, and intellectual property on development and dissemination of the polymerase chain reaction: case study", J. Biomed. Disc. & Collabo., 1(7) (2006).

Ganz, T., et al., "Defensins, Natural Peptide Antibiotics of Human Neutrophils", J. Clin. Invest. 76 pp. 1427-35 Oct. (1985).

Langer, R., and Riggs, M., "*Cryptosporidium parvum* Apical Complex Glycoprotein CSL Contains a Sporozoite Ligand for Intestinal Epithelial Cells", Infect. & Immun. 67(10) pp. 5282-91 (1999).

Langer, R., et al., "Characterization of an Intestinal Epithelial Cell Receptor Recognized by the *Cryptosporidium parvum* Sporozoite Ligand CSL", Infect. & Immun. 69(3) pp. 1661-70 (2001).

Moreira, L., et al., "Bee Venom Phospholipase Inhibits Malaria Parasite Development in Transgenic Mosquitoes", J. Biol. Chem. 277(43) pp. 40839-43 (2002).

Selsted, M. and Harwig, S. "Purification, Primary Structure, and Antimicrobial Activities of a Guinea Pig Neutrophil Defensin", Infect. & Immun. 55(9) pp. 2281-6 (1987).

Wilde, C., et al., "Purification and Characterization of Human Neutrophil Peptide 4, a Novel Member of the Defensin Family", J. Biol. Chem. 264.

Wong, A. "Biofilms in Food Processing Environments", J. Dairy Sci. 81 pp. 2765-2770 (1998).

McGwire, B. "Killing of African Trypanosomes by Antimicrobial Peptides", J. Infect. Disease; 188 pp. 146-152 (2003).

Flint, S.H., et al., "Biofilms In Dairy Manufacturing Plant-Description, Current Concerns and Methods of Control", Biofouling, vol. 11(1) pp. 81-97 (1997).

Riggs, M.W., et al., "Protective Monoclonal Antibody Defines a Circumsporozite-Like Glycoprotein Exoantigen of *Cryptosaporidium parvum* Sporozoites and Merozoites", J. of Immunology, 158 pp. 1787-1795 (1997).

Barker, J., and Bloomfield, S.F., "Survival of *Salmonella* In Bathrooms and toilets in domestic homes following salmonellosis", J. of Applied Microbiology, 89, pp. 137-144 (2000).

Ibrahim, H.R., et al., "Genetic evidence that antibacterial activity off lysozyme is independent of its catlaytic function", FEBS Letters, 506 pp. 27-32 (2001).

Tzipori, S., and Ward, H., "Cryptosporidiosus: biology, pathogenesis and disease", Microbes and Infection, 4 pp. 1047-1058 (2002).

Zeya et al., "Antimicrobial Specificity of Leukocyte Lysosomal Cationic Proteins," Science, 154:1049 1051 [1966].

Hancock, D.D., et al., "The prevalence of *Escheria coli* 0157.H7 in dairy and beef cattle in Washington State", Epidemiol. Infect., 113(2):199-207 (1994).

Riggs, M. , Microbes Infect., Recent advances in cryptosporidiosis: the immune response. Microbes. Infect 4:1067-1080, 2002 4:1067 [2002].

Robinson, C. and Sauer, R. "Optimizing the stability of single-chain proteins by linker length and composition mutagenesis", Poc.Natl. Acad. Sci. 95 pp. 5929-34 (1998).

Schaefer, D.A., et al., "Characterization and Formulation of Multiple Epitope-Specific Neutralizing Monoclonal Antibodies for Passive Immunization against Cryptosporidiosus," Infection and Immunity 68:2608-2616.

Pellegrini, A., et al., Biochem. Biophys. Res. Commun., Identification and Isolation of the Bactericidal Domains in the Proteinase Inhibitor Aprotinin, 222(2):559-565 [1996].

Takada, K., et al., "Binding of Lysozyme to Lipopolysaccharide Supresses Tumor Necrosis Factor Production In Vivo", Infect. Immun., vol. 62(4), pp. 1171-1175 (1994).

Tzipori, S., and Ward, H., "Cryptosporidiosus: biology, pathogenesis and disease", Microbes and Infection, 4 pp. 1047-58 (2002).

Zottola and Sasahara, "Microbial biofilms in the fodd processing industy-Should they be a concern?", Int J Food Microbiol; 23:125-48 (1994).

Gerhard, et al., "Prospects for Universal Influenza Virus Vaccine", Emerging Infectious Diseases, vol. 12, pp. 569-74 (2006).

Zebedee, et al., "Influenza A Virus M2 Protein: Monoclonal Antibody Restriction of Virus Growth and Detection of M2 in Virions", Journal of Virology, vol. 62, pp. 2762-2772 (1988).

ABBAS et al., Cellular and Molecular Immunology 4th ed. 2000 pp. 50-51.

Okuda et al. "New Type of Antibody-Enzyme Conjugate Which Specifically Kills *Candida albicans*", Infection and Immunity Feb. 1980, pp. 690-692.

Cortruvo et al., "Waterborne Zoonoses: Idnetification, Causes and Control". Emerging Issues in Water and Infectious Diseases Series, World Helath Organization, Section V, pp. 209-212, 2004.

Lis et al., "Galactose Oxidase-Glucan Binding Domain Fusion Proteins as Targeting Inhibitors of Dental Plaque Bacteria", Antimicrobial Agents and Chemotherapy, May 1997, pp. 999-1003.

Merriam Webster Dictionary definition of foodstuff.

Merriam Webster Dictionary definition of microorganism.

Yoshida, et al. "Separation of Lactoferrin-a and -b from Bovine *Colostrum*", J. Dairy Sci 83:2211-2215.

Saito et al., "Potent Bactericidal Activity of Bovine Lactoferrin Hydrolysate produced by Heat Treatment at Acidic pH", J. Dairy Sci 74:3724:3730.

Randall et al., "J. Chain Synthesis and Secretion of Hexameric IgM is Differentially Regulated by Lipopolysaccharide and Interleukin 5", PNAS vol. 89, pp. 962-966, 1992.

Schultz et al. "BPI'ANCA is found in reactive arthritis caused by *Yersinia* and Salmonell infection and recognize exclusively the C-terminal part of the BPI molecule", Scand. J. Rheumaltol. 2000, vol. 29, pp. 226-231.

Medvedev et al., "Regulation of fas and fas-ligand expression in NK cells by Cytokines and the involvement of fas-ligand in NK/LAK cell-mediated cytotoxity." Cytokine, Jun. 6, 1997, vol. 9, No. 6, pp. 394-404.

Yoshida, Shigeto, "Bacteria expressing single-chain immunotoxin inhibit malaria parasite development in mosquitoes", Molecular and Biochemical Parasitology, vol. 113, No. 1, Mar. 2001, pp. 89-96, XP002429871, ISSN: 0166-6851.

Oren, et al, "Structure and organization of the human antimicrobial peptide LL-37 in phospholipid membranes: relevance to the molecular basis for its non-cell-selective activity". Biochem. J. Aug. 1, 1999. vol. 341, Pt. 3, pp. 501-513; abstract; p. 502, para 1.

Perryman, et al., "Kinetics of *Cryptosporidium parvum* Sporozoite Neutralization by Monoclonal Antibodies". Immune Bovine Serum, and Immune Bovine Colostrum. Infect. Immun. Jan. 1990, vol. 58, No. 1, pp. 257-259.

Cayman Chemical CPLA2 Assay kit technical bulletin pp. 1-8, Catalog No. 765021.

Calbiochem, Lactoferrin ELISA kit, Catalog No. 427275, Rev. 4 Nov. 2005 RFH, 6 pages.

Merriam Webster Dictionary definition of foodstuff http://www.m-w.com/cgi-bin/dictionary?book=Dictionary&va=microorganism retrieved Feb. 24, 2007.

Merriam Webster Dictionary definition of microorganism http://www.m-w.com/cgi-bin/dictionary?book=Dictionary&va=foodstuff retrieved Feb. 24, 2007.

Yoshida, et al. "Separation of Lactoferrin-a and -b from Bovine Colostrum", J. Dairy Sci 83:2211-2215, 2000.

Saito et al., "Potent Bactericidal Activity of Bovine Lactoferrin Hydrolysate produced by Heat Treatment at Acidic pH", J. Dairy Sci 74:3724:3730, 1991.

Schultz et al. "BPI'ANCA is found in reactive arthritis caused by Yersinia and Salmonell infection and recognize exclusively the C-terminal part of the BPI molecule", Scand. J. Rheumaltol. 2000, vol. 29, pp. 226-231.

Perryman, et al., "Kinetics of Cryptosporidium Parvum Sporozoite Neutralization by Monoclonal Antibodies". Immune Bovine Serum, and Immune Bovine Colostrum. Infect. Immun. Jan. 1990, vol. 58, No. 1, pp. 257-259.

Cayman Chemical CPLA2 Assay kit technical bulletin pp. 1-8, Catalog No. 765021 Feb. 17, 2003, Cayman Chemical Company, Ann Arbor, MI.

* cited by examiner

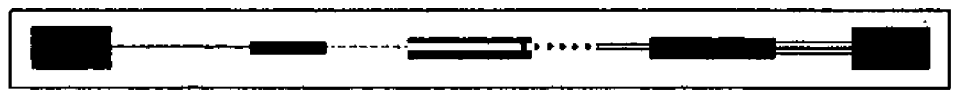

- Moloney Murine Leukemia Virus 5'LTR
- Moloney Murine Leukemia Virus extended packaging region
- bovine alpha-lactalbumin Promoter **
- α-Lactalbumin signal peptide
- Murine IgG2a heavy chain gene (cDNA)
- Encephalomyocarditis virus internal ribosome entry site
- α-Lactalbumin signal peptide
- Murine antibody κ light chain gene (cDNA)
- RNA transport element
- Moloney Murine Leukemia Virus 3' LTR

B

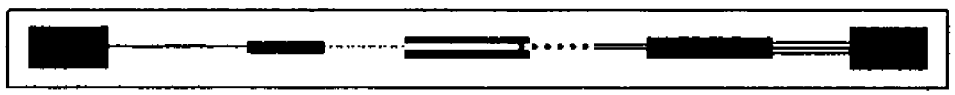

- Moloney Murine Leukemia Virus 5'LTR
- Moloney Murine Leukemia Virus extended packaging region
- bovine alpha-lactalbumin Promoter **
- α-Lactalbumin signal peptide
- Murine IgG2a heavy chain gene (cDNA)
- Encephalomyocarditis virus internal ribosome entry site
- α-Lactalbumin signal peptide
- Murine antibody κ light chain gene (cDNA)
- RNA transport element
- Moloney Murine Leukemia Virus 3' LTR

Figure 3

Figure 3 PLA2 Neutralization of *C. parvum* Sporozoites

Figure 8

Human CD14-PLA2 construct (SEQ ID NO:97)

```
TCCGGTCGACCTATGGCTATTGGCCAGGTTCAATACTATGTATTGGCCCTA
TGCCATATAGTATTCCATATATGGGTTTTCCTATTGACGTAGATAGCCCCT
CCCAATGGGCGGTCCCATATACCATATATGGGGCTTCCTAATACCGCCCAT
AGCCACTCCCCCATTGACGTCAATGGTCTCTATATATGGTCTTTCCTATTG
ACGTCATATGGGCGGTCCTATTGACGTATATGGCGCCTCCCCCATTGACGT
CAATTACGGTAAATGGCCCGCCTGGCTCAATGCCCATTGACGTCAATAGG
ACCACCCACCATTGACGTCAATGGGATGGCTCATTGCCCATTCATATCCGT
TCTCACGCCCCCTATTGACGTCAATGACGGTAAATGGCCCACTTGGCAGTA
CATCAATATCTATTAATAGTAACTTGGCAAGTACATTACTATTGGAAGTAC
GCCAGGGTACATTGGCAGTACTCCCATTGACGTCAATGGCGGTAAATGGC
CCGCGATGGCTGCCAAGTACATCCCCATTGACGTCAATGGGGAGGGGCAA
TGACGCAAATGGGCGTTCCATTGACCTAAATGGGCGGTAGGCGTGCCTAA
TGGGAGGTCTATATAAGCAATGCTCGTTTAGGGAACCGCCATTCTGCCTG
GGGACGTCGGAGGAGCTCGAATGGAGCGCGCGTCCTGCTTGTTGCTGCTG
CTGCTGCCGCTGGTGCACGTCTCTGCGACCACGCCAGAACCTTGTGAGCTG
GACGATGAAGATTTCCGCTGCGTCTGCAACTTCTCCGAACCTCAGCCCGAC
TGGTCCGAAGCCTTCCAGTGTGTGTCTGCAGTAGAGGTGGAGATCCATGC
CGGCGGTCTCAACCTAGAGCCGTTTCTAAAGCGCGTCGATGCGGACGCCG
ACCCGCGGCAGTATGCTGACACGGTCAAGGCTCTCCGCGTGCGGCGGCTC
ACAGTGGGAGCCGCACAGGTTCCTGCTCAGCTACTGGTAGGCGCCCTGCG
TGTGCTAGCGTACTCCCGCCTCAAGGAACTGACGCTCGAGGACCTAAAGA
TAACCGGCACCATGCCTCCGCTGCCTCTGGAAGCCACAGGACTTGCACTTT
CCAGCTTGCGCCTACGCAACGTGTCGTGGGCGACAGGGCGTTCTTGGCTC
GCCGAGCTGCAGCAGTGGCTCAAGCCAGGCCTCAAGGTACTGAGCATTGC
CCAAGCACACTCGCCTGCCTTTTCCTGCGAACAGGTTCGCGCCTTCCCGGC
CCTTACCAGCCTAGACCTGTCTGACAATCCTGGACTGGGCGAACGCGGAC
TGATGGCGGCTCTCTGTCCCCACAAGTTCCCGGCCATCCAGAATCTAGCGC
TGCGCAACACAGGAATGGAGACGCCCACAGGCGTGTGCGCCGCACTGGC
```

Figure 8 (cont.)

```
GGCGGCAGGTGTGCAGCCCCACAGCCTAGACCTCAGCCACAACTCGCTGC
GCGCCACCGTAAACCCTAGCGCTCCGAGATGCATGTGGTCCAGCGCCCTG
AACTCCCTCAATCTGTCGTTCGCTGGGCTGGAACAGGTGCCTAAAGGACT
GCCAGCCAAGCTCAGAGTGCTCGATCTCAGCTGCAACAGACTGAACAGGG
CGCCGCAGCCTGACGAGCTGCCCGAGGTGGATAACCTGACACTGGACGGG
AATCCCTTCCTGGTCCCTGGAACTGCCCTCCCCCACGAGGGCTCAATGAAC
TCCGGCGTGGTCCCAGCCTGTGCACGTTCGACCCTGTCGGTGGGGGTGTCG
GGAACCCTGGTGCTGCTCCAAGGGGCCCGGGGCTTTGCCGGTGGAGGCGG
TTCAGGCGGAGGTGGCTCTGGCGGTGGCGGATCGAAGACCCTCCTACTGT
TGGCAGTGATCATGATCTTTGGCCTACTGCAGGCCCATGGGAATTTGGTGA
ATTTCCACAGAATGATCAAGTTGACGACAGGAAAGGAAGCCGCACTCAGT
TATGGCTTCTACGGCTGCCACTGTGGCGTGGGTGGCAGAGGATCCCCCAA
GGATGCAACGGATCGCTGCTGTGTCACTCATGACTGTTGCTACAAACGTCT
GGAGAAACGTGGATGTGGCACCAAATTTCTGAGCTACAAGTTTAGCAACT
CGGGGAGCAGAATCACCTGTGCAAAACAGGACTCCTGCAGAAGTCAACTG
TGTGAGTGTGATAAGGCTGCTGCCACCTGTTTTGCTAGAAACAAGACGAC
CTACAATAAAAGTACCAGTACTATTCCAATAAACACTGCAGAGGGAGCA
CCCCTCGTTGCTGAGTCCCCTCTTCCCTGGAAACCTTCCACCCAGTGCTGA
ATTTCCCTCTCTCATACCCTCCCTCCCTACCCTAACCAAGTTCCTTGGCCAT
GCAGAAAGCATCCCTCACCCATCCTAGAGGCCAGGCAGGAGCCCTTCTAT
ACCCACCCAGAATGAGACATCCAGCAGATTCCAGCCTTCTACTGCTCTCC
TCCACCTCAACTCCGTGCTTAACCAAAGAAGCTGTACTCCGGGGGGTCTCT
TCTGAATAAAGCAATTAGC
```

1-678 Simian CMV promoter 679-1803 Coding sequence for human CD14

1804-1848 Codon-optimized Glycine serine linker 1849-2280 Coding sequence for human PLA2 group IIA 2281-2541 3'UTR with poly-A site

Figure 9

Human LRP-PLA2 construct (SEQ ID NO:98)

```
TCCGGTCGACCTATGGCTATTGGCCAGGTTCAATACTATGTATTGGCCCTA
TGCCATATAGTATTCCATATATGGGTTTTCCTATTGACGTAGATAGCCCCT
CCCAATGGGCGGTCCCATATACCATATATGGGGCTTCCTAATACCGCCCAT
AGCCACTCCCCCATTGACGTCAATGGTCTCTATATATGGTCTTTCCTATTG
ACGTCATATGGGCGGTCCTATTGACGTATATGGCGCCTCCCCCATTGACGT
CAATTACGGTAAATGGCCCGCCTGGCTCAATGCCCATTGACGTCAATAGG
ACCACCCACCATTGACGTCAATGGGATGGCTCATTGCCCATTCATATCCGT
TCTCACGCCCCCTATTGACGTCAATGACGGTAAATGGCCCACTTGGCAGTA
CATCAATATCTATTAATAGTAACTTGGCAAGTACATTACTATTGGAAGTAC
GCCAGGGTACATTGGCAGTACTCCCATTGACGTCAATGGCGGTAAATGGC
CCGCGATGGCTGCCAAGTACATCCCCATTGACGTCAATGGGGAGGGGCAA
TGACGCAAATGGGCGTTCCATTGACGTAAATGGGCGGTAGGCGTGCCTAA
TGGGAGGTCTATATAAGCAATGCTCGTTTAGGGAACCGCCATTCTGCCTG
GGGACGTCGGAGGAGCTCGAATGGGGGCCTTGGCAAGAGCCCTGCCGTCC
ATACTGCTGGCATTGCTGCTTACGTCCACCCCAGAGGCTCTGGGTGCCAAC
CCCGGCTTGGTCGCCAGGATCACCGACAAGGGACTGCAGTATGCGGCCCA
GGAGGGGCTATTGGCTCTGCAGAGTGAGCTGCTCAGGATCACGCTGCCTG
ACTTCACCGGGGACTTGAGGATCCCCCACGTCGGCCGTGGGCGCTATGAG
TTCCACAGCCTGAACATCCACAGCTGTGAGCTGCTTCACTCTGCGCTGAGG
CCTGTCCCCGGCCAGGGCCTGAGTCTCAGCATCTCCGACTCCTCCATCCGG
GTCCAGGGCAGGTGGAAGGTGCGCAAGTCATTCTTCAAACTACAGGGCTC
CTTTGATGTCAGTGTCAAGGGCATCAGCATTTCGGTCAACCTCCTGTTGGG
CAGCGAGTCCTCCGGGAGGCCCACAGGTTACTGCCTCAGCTGCAGCAGTG
ACATCGCTGACGTGGAGGTGGACATGTCGGGAGATTCGGGGTGGCTCTTG
AACCTCTTCCACAACCAGATTGAGTCCAAGTTCCAGAAAGTACTCGAGAG
CAGGGGTGGAGGCGGTTCAGGCGGAGGTGGCTCTGGCGGTGGCGGATCG
AAGACCCTCCTACTGTTGGCAGTGATCATGATCTTTGGCCTACTGCAGGCC
CATGGGAATTTGGTGAATTTCCACAGAATGATCAAGTTGACGACAGGAAA
```

Figure 9 (cont.)

GGAAGCCGCACTCAGTTATGGCTTCTACGGCTGCCACTGTGGCGTGGGTG
GCAGAGGATCCCCCAAGGATGCAACGGATCGCTGCTGTGTCACTCATGAC
TGTTGCTACAAACGTCTGGAGAAACGTGGATGTGGCACCAAATTTCTGAG
CTACAAGTTTAGCAACTCGGGGAGCAGAATCACCTGTGCAAAACAGGACT
CCTGCAGAAGTCAACTGTGTGAGTGTGATAAGGCTGCTGCCACCTGTTTTG
CTAGAAACAAGACGACCTACAATAAAAGTACCAGTACTATTCCAATAAA
CACTGCAGAGGGAGCACCCCTCGTTGCTGAGTCCCCTCTTCCCTGGAAACC
TTCCACCCAGTGCTGAATTTCCCTCTCTCATACCCTCCCTCCCTACCCTAAC
CAAGTTCCTTGGCCATGCAGAAAGCATCCCTCACCCATCCTAGAGGCCAG
GCAGGAGCCCTTCTATACCCACCCAGAATGAGACATCCAGCAGATTTCCA
GCCTTCTACTGCTCTCCTCCACCTCAACTCCGTGCTTAACCAAAGAAGCTG
TACTCCGGGCGGTCTCTTCTGAATAAAGCAATTAGC 1-678 Simian CMV promoter 679-1267 Coding sequence for human LPB 1268-1311 Codon-optimized Glycine serine linker 1312-1743 Coding sequence for human PLA2 group IIA 1744-2003 3'UTR with poly-A initiation site

Figure 10

Human MBL-PLA2 construct (SEQ ID NO:99)

```
TCCGGTCGACCTATGGCTATTGGCCAGGTTCAATACTATGTATTGGCCCTA
TGCCATATAGTATTCCATATATGGGTTTTCCTATTGACGTAGATAGCCCCT
CCCAATGGGCGGTCCCATATACCATATATGGGGCTTCCTAATACCGCCCAT
AGCCACTCCCCATTGACGTCAATGGTCTCTATATATGGTCTTTCCTATTG
ACGTCATATGGGCGGTCCTATTGACGTATATGGCGCCTCCCCCATTGACGT
CAATTACGGTAAATGGCCCGCCTGGCTCAATGCCCATTGACGTCAATAGG
ACCACCCACCATTGACGTCAATGGGATGGCTCATTGCCCATTCATATCCGT
TCTCACGCCCCTATTGACGTCAATGACGGTAAATGGCCCACTTGGCAGTA
CATCAATATCTATTAATAGTAACTTGGCAAGTACATTACTATTGGAAGTAC
GCCAGGGTACATTGGCAGTACTCCCATTGACGTCAATGGCGGTAAATGGC
CCGCGATGGCTGCCAAGTACATCCCCATTGACGTCAATGGGGAGGGGCAA
TGACGCAAATGGGCGTTCCATTGACGTAAATGGGCGGTAGGCGTGCCTAA
TGGGAGGTCTATATAAGCAATGCTCGTTTAGGGAACCGCCATTCTGCCTG
GGGACGTCGGAGGAGCTCGAATGTCCCTGTTTCCATCACTCCCTCTCCTTC
TCCTGAGTATGGTGGCAGCGTCTTACTCAGAAACTGTGGCCTGTGAGGAT
GCCCAAAAGACCTGCCCTGCAGTGATTGCCTGTAGCTCTCCAGGCATCAA
CGGCTTCCCAGGCAAAGATGGGCGTGATGGCACCAAGGGAGAAAAGGGG
GAACCAGGCCAAGGGCTCAGAGGCTTACAGGGCCCCCCTGGAAAGTTGG
GGCCTCCAGGAAATCCAGGGCCTTCTGGGTCACCAGGACCAAAGGGCCAA
AAAGGAGACCCTGGAAAAAGTCCGGATGGTGATAGTAGCCTGGCTGCCTC
AGAAAGAAAAGCTCTGCAAACAGAAATGGCACGTATCAAAAAGTGGCTG
ACCTTCTCTCTGGGCAAACAAGTTGGGAACAAGTTCTTCCTGACCAATGGT
GAAATAATGACCTTTGAAAAAGTGAAGGCCTTGTGTGTCAAGTTCCAGGC
CTCTGTGGCCACCCCAGGAATGCTGCAGAGAATGGAGCCATTCAGAATC
TCATCAAGGAGGAAGCCTTCCTGGGTATCACTGATGAAGACAGAAGGG
CAGTTTGTGGATCTGACAGGAAATAGACTGACCTACACAAACTGGAACGA
GGGTGAACCCAACAATGCTGGTTCTGATGAAGATTGTGTATTGCTACTGA
AAAATGGCCAGTGGAATGACGTCCCCTGCTCCACCTCCCATCTGGCCGTCT
```

Figure 10 (cont.)

```
GTGAGTTCCCTATCGGTGGAGGCGGTTCAGGCGGAGGTGGCTCTGGCGGT
GGCGGATCGAAGACCCTCCTACTGTTGGCAGTGATCATGATCTTTGGCCTA
CTGCAGGCCCATGGGAATTTGGTGAATTTCCACAGAATGATCAAGTTGAC
GACAGGAAAGGAAGCCGCACTCAGTTATGGCTTCTACGGCTGCCACTGTG
GCGTGGGTGGCAGAGGATCCCCCAAGGATGCAACGGATCGCTGCTGTGTC
ACTCATGACTGTTGCTACAAACGTCTGGAGAAACGTGGATGTGGCACCAA
ATTTCTGAGCTACAAGTTTAGCAACTCGGGGAGCAGAATCACCTGTGCAA
AACAGGACTCCTGCAGAAGTCAACTGTGTGAGTGTGATAAGGCTGCTGCC
ACCTGTTTTGCTAGAAACAAGACGACCTACAATAAAAGTACCAGTACTA
TTCCAATAAACACTGCAGAGGGAGCACCCCTCGTTGCTGAGTCCCCTCTTC
CCTGGAAACCTTCCACCCAGTGCTGAATTTCCCTCTCTCATACCCTCCCTC
CCTACCCTAACCAAGTTCCTTGGCCATGCAGAAAGCATCCCTCACCCATCC
TAGAGGCCAGGCAGGAGCCCTTCTATACCCACCCAGAATGAGACATCCAG
CAGATTTCCAGCCTTCTACTGCTCTCCTCCACCTCAACTCCGTGCTTAACC
AAAGAAGCTGTACTCCGGGGGGTCTCTTCTGAATAAAGCAATTAGC
```

1-678 Simian CMV promoter 679-1425 Coding sequence for human MBL 1423-1467 Codon-optimized Glycine serine linker 1468-1899 Coding sequence for human PLA2 group IIA 1900-2159 3'UTR with poly-A initiation site

Figure 11

Human SP-D-PLA2 construct (SEQ ID NO:100)

TCCGGTCGACCTATGGCTATTGGCCAGGTTCAATACTATGTATTGGCCCTA
TGCCATATAGTATTCCATATATGGGTTTTCCTATTGACGTAGATAGCCCCT
CCCAATGGGCGGTCCCATATACCATATATGGGGCTTCCTAATACCGCCCAT
AGCCACTCCCCCATTGACGTCAATGGTCTCTATATATGGTCTTTCCTATTG
ACGTCATATGGGCGGTCCTATTGACGTATATGGCGCCTCCCCCATTGACGT
CAATTACGGTAAATGGCCCGCCTGGCTCAATGCCCATTGACGTCAATAGG
ACCACCCACCATTGACGTCAATGGGATGGCTCATTGCCCATTCATATCCGT
TCTCACGCCCCCTATTGACGTCAATGACGGTAAATGGCCCACTTGGCAGTA
CATCAATATCTATTAATAGTAACTTGGCAAGTACATTACTATTGGAAGTAC
GCCAGGGTACATTGGCAGTACTCCCATTGACGTCAATGGCGGTAAATGGC
CCGCGATGGCTGCCAAGTACATCCCCATTGACGTCAATGGGGAGGGGCAA
TGACGCAAATGGGCGTTCCATTGACGTAAATGGGCGGTAGGCGTGCCTAA
TGGGAGGTCTATATAAGCAATGCTCGTTTAGGGAACCGCCATTCTGCCTG
GGGACGTCGGAGGAGCTCGAATGCTGCTCTTCCTCCTCTCTGCACTGGTCC
TACTCACACAGCCCCTGGGCTACCTGGAAGCAGAAATGAAGACCTACTCC
CACAGAACAACGCCCAGTGCTTGCACCCTGGTCATGTGTAGCTCAGTGGA
GAGTGGCCTGCCTGGTCGCGATGGACGGGATGGGAGAGAGGGCCCTCGG
GGCGAGAAGGGGGACCCAGCTTTGCCAGGAGCTGCAGGGCAAGCAGGGA
TGCCTGGACAAGCTGGCCCAGTTGGGCCCAAAGGGGACAATGGCTCTGTT
GGAGAACCTGGACCAAAGGGAGACACTGGGCCAAGTGGACCTCCAGGAC
CTCCCGGTGTGCCTGGTCCAGCTGGAAGAGAAGGTCCCCTGGGGAAGCAG
GGGAACATAGGACCTCAGGGCAAGCCAGGCCCAAAAGGAGAAGCTGGGC
CCAAAGGAGAAGTAGGTGCCCCAGGCATGCAGGGCTCGGCAGGGGCAAG
AGGCCTCGCAGGCCCTAAGGGAGAGCGAGGTGTCCCTGGTGAGCGTGGA
GTCCCTGGAAACGCAGGGGCAGCAGGGTCTGCTGGAGCCATGGGTCCCCA
GGGAAGTCCAGGTGCCAGGGGACCCCGGGATTGAAGGGGGACAAAGGC
ATTCCTGGAGACAAAGGAGCAAAGGGAGAAAGTGGGCTTCCAGATGTTG
CTTCTCTGAGGCAGCAGGTTGAGGCCTTACAGGGACAAGTACAGCACCTC
CAGGCTGCTTTCTCTCAGTATAAGAAAGTTGAGCTCTTCCCAAATGGCCAA

Figure 11 (cont.)

```
AGTGTCGGGGAGAAGATTTTCAAGACAGCAGGCTTTGTAAAACCATTTAC
GGAGGCACAGCTGCTGTGCACACAGGCTGGTGGACAGTTGGCCTCTCCAC
GCTCTGCCGCTGAGAATGCCGCCTTGCAACAGCTGGTCGTAGCTAAGAAC
GAGGCTGCTTTCCTGAGCATGACTGATTCCAAGACAGAGGGCAAGTTCAC
CTACCCCACAGGAGAGTCCCTGGTCTATTCCAACTGGGCCCCAGGGGAGC
CCAACGATGATGGCGGGTCAGAGGACTGTGTGGAGATCTTCACCAATGGC
AAGTGGAATGACAGGGCTTGTGGAGAAAAGCGTCTTGTGGTCTGCGAGTT
CGGTGGAGGCGGTTCAGGCGGAGGTGGCTCTGGCGGTGGCGGATCGAAG
ACCCTCCTACTGTTGGCAGTGATCATGATCTTTGGCCTACTGCAGGCCCAT
GGGAATTTGGTGAATTTCCACAGAATGATCAAGTTGACGACAGGAAAGGA
AGCCGCACTCAGTTATGGCTTCTACGGCTGCCACTGTGGCGTGGGTGGCA
GAGGATCCCCCAAGGATGCAACGGATCGCTGCTGTCACTCATGACTGT
TGCTACAAACGTCTGGAGAAACGTGGATGTGGCACCAAATTTCTGAGCTA
CAAGTTTAGCAACTCGGGGAGCAGAATCACCTGTGCAAAACAGGACTCCT
GCAGAAGTCAACTGTGTGAGTGTGATAAGGCTGCTGCCACCTGTTTTGCTA
GAAACAAGACGACCTACAATAAAAGTACCAGTACTATTCCAATAAACAC
TGCAGAGGGAGCACCCCTCGTTGCTGAGTCCCCTCTTCCCTGGAAACCTTC
CACCCAGTGCTGAATTTCCCTCTCTCATACCCTCCCTCCCTACCCTAACCA
AGTTCCTTGGCCATGCAGAAAGCATCCCTCACCCATCCTAGAGGCCAGGC
AGGAGCCCTTCTATACCCACCCAGAATGAGACATCCAGCAGATTTCCAGC
CTTCTACTGCTCTCCTCCACCTCAACTCCGTGCTTAACCAAAGAAGCTGTA
CTCCGGGGGGTCTCTTCTGAATAAAGCAATTAGC
```

1-678 Simian CMV promoter 679-1803 Coding sequence for human SP-D 1804-1848 Codon-optimized Glycine serine linker 1849-2280 Coding sequence for human PLA2 group IIA 2281-2540 3'UTR with poly-A initiation site

Figure 12

Mouse IgM-PLA2 construct (SEQ ID NO:101)

TCCGGTCGACCTATGGCTATTGGCCAGGTTCAATACTATGTATTGGCCCTA
TGCCATATAGTATTCCATATATGGGTTTTCCTATTGACGTAGATAGCCCCT
CCCAATGGGCGGTCCCATATACCATATATGGGGCTTCCTAATACCGCCCAT
AGCCACTCCCCCATTGACGTCAATGGTCTCTATATATGGTCTTTCCTATTG
ACGTCATATGGGCGGTCCTATTGACGTATATGGCGCCTCCCCCATTGACGT
CAATTACGGTAAATGGCCCGCCTGGCTCAATGCCCATTGACGTCAATAGG
ACCACCCACCATTGACGTCAATGGGATGGCTCATTGCCCATTCATATCCGT
TCTCACGCCCCTATTGACGTCAATGACGGTAAATGGCCCACTTGGCAGTA
CATCAATATCTATTAATAGTAACTTGGCAAGTACATTACTATTGGAAGTAC
GCCAGGGTACATTGGCAGTACTCCCATTGACGTCAATGGCGGTAAATGGC
CCGCGATGGCTGCCAAGTACATCCCCATTGACGTCAATGGGGAGGGGCAA
TGACGCAAATGGGCGTTCCATTGACGTAAATGGGCGGTAGGCGTGCCTAA
TGGGAGGTCTATATAAGCAATGCTCGTTTAGGGAACCGCCATTCTGCCTG
GGGACGTCGGAGGAGCTCGAATGGCTGTCCTGGTGCTGTTCCTCTGCCTG
GTTGCATTTCCAAGCTGTGTCCTGTCCCAGGTGCAGCTGAAGGAGTCAGG
ACCTGGCCTGCTGGCGCCCTCACAGAGCCTGTCCATCACTTGCACTGTCTC
TGGGTTTTCATTAACCAACTATGGTGTACATTGGGTTCGCCAGCCTCCAGG
AAAGGGTCTGGAGTGGCTGGGAGTAATATGGGCTGGTGGAAACACAAATT
ATAATTCGGCTTTTATGTCCAGACTGAGCATCACCAAAGACAACTCCAAG
AGCCAAGTTTTCATAAAAATGAACAGTCTGCAAACTGATGACACAGCCAT
GTACTACTGTGCCAGAGAATATAGGCACGGGGCTTACTATGCTATGGACT
ACTGGGGTCAAGGAACCTCAGTCACCGTCTCCTCAGAGTCAGTCCTTC
CCAAATGTCTTCCCCCTCGTCTCCTGCGAGAGCCCCCTGTCTGATAAGAAT
CTGGTGGCCATGGGCTGCCTGGCCCGGGACTTCCTGCCCAGCACCATTTCC
TTCACCTGGAACTACCAGAACAACACTGAAGTCATCCAGGGTATCAGAAC
CTTCCCAACACTGAGGACAGGGGGCAAGTACCTAGCCACCTCGCAGGTGT
TGCTGTCTCCCAAGAGCATCCTTGAAGGTTCAGATGAATACCTGGTATGCA
AAATCCACTACGGAGGCAAAAACAGAGATCTGCATGTGCCCATTCCAGCT
GTCGCAGAGATGAACCCCAATGTAAATGTGTTCGTCCCACCACGGGATGG

Figure 12 (cont.)

```
CTTCTCTGGCCCTGCACCACGCAAGTCTAAACTCATCTGCGAGGCCACGA
ACTTCACTCCAAAACCGATCACAGTATCCTGGCTAAAGGATGGGAAGCTC
GTGGAATCTGGCTTCACCACAGATCCGGTGACCATCGAGAACAAAGGATC
CACACCCCAAACCTACAAGGTCATAAGCACACTTACCATCTCTGAAATCG
ACTGGCTGAACCTGAATGTGTACACCTGCCGTGTGGATCACAGGGGTCTC
ACCTTCTTGAAGAACGTGTCCTCCACATGTGCTGCCAGTCCCTCCACAGAC
ATCCTGACCTTCACCATCCCCCCCTCCTTTGCCGACATCTTCCTCAGCAAG
TCCGCTAACCTGACCTGTCTGGTCTCAAACCTGGCAACCTATGAAACCCTG
AATATCTCCTGGGCTTCTCAAAGTGGTGAACCACTGGAAACCAAAATTAA
AATCATGGAAAGCCATCCCAATGGCACCTTCAGTGCTAAGGGTGTGGCTA
GTGTTTGTGTGGAAGACTGGAATAACAGGAAGGAATTTGTGTGTACTGTG
ACTCACAGGGATCTGCCTTCACCACAGAAGAAATTCATCTCAAAACCCAA
TGAGGTGCACAAACATCCACCTGCTGTGTACCTGCTGCCACCAGCTCGTG
AGCAACTGAACCTGAGGGAGTCAGCCACAGTCACCTGCCTGGTGAAGGGC
TTCTCTCCTGCAGACATCAGTGTGCAGTGGCTTCAGAGAGGGCAACTCTTG
CCCCAAGAGAAGTATGTGACCAGTGCCCCGATGCCAGAGCCTGGGGCCCC
AGGCTTCTACTTTACCCACAGCATCCTGACTGTGACAGAGGAGGAATGGA
ACTCCGGAGAGACCTATACCTGTGTTGTAGGCCACGAGGCCCTGCCACAC
CTGGTGACCGAGAGGACCGTGGACAAGTCCACTGGTAAACCCACACTGTA
CAATGTCTCCCTGATCATGTCTGACACAGGCGGCACCTGCTATTGAAATTC
GCCCCTCTCCCTCCCCCCCCCCTAACGTTACTGGCCGAAGCCGCTTGGAAT
AAGGCCGGTGTGCGTTTGTCTATATGTTATTTTCCACCATATTGCCGTCTTT
TGGCAATGTGAGGGCCCGGAAACCTGGCCCTGTCTTCTTGACGAGCATTC
CTAGGGGTCTTTCCCCTCTCGCCAAAGGAATGCAAGGTCTGTTGAATGTCG
TGAAGGAAGCAGTTCCTCTGGAAGCTTCTTGAAGACAAACAACGTCTGTA
GCGACCCTTTGCAGGCAGCGGAACCCCCACCTGGCGACAGGTGCCTCTG
CGGCCAAAAGCCACGTGTATAAGATACACCTGCAAAGGCGGCACAACCCC
AGTGCCACGTTGTGAGTTGGATAGTTGTGGAAAGAGTCAAATGGCTCTCC
TCAAGCGTATTCAACAAGGGGCTGAAGGATGCCCAGAAGGTACCCCATTG
TATGGGATCTGATCTGGGGCCTCGGTGCACATGCTTTACATGTGTTTAGTC
GAGGTTAAAAAAACGTCTAGGCCCCCCGAACCACGGGGACGTGGTTTTCC
TTTGAAAAACACGATGATGGTGGAGGCGGTTCAGGCGGAGGTGGCTCTGG
```

Figure 12 (cont.)

CGGTGGCGGATCGAAGACCCTCCTACTGTTGGCAGTGATCATGATCTTTGG
CCTACTGCAGGCCCATGGGAATTTGGTGAATTTCCACAGAATGATCAAGT
TGACGACAGGAAAGGAAGCCGCACTCAGTTATGGCTTCTACGGCTGCCAC
TGTGGCGTGGGTGGCAGAGGATCCCCCAAGGATGCAACGGATCGCTGCTG
TGTCACTCATGACTGTTGCTACAAACGTCTGGAGAAACGTGGATGTGGCA
CCAAATTTCTGAGCTACAAGTTTAGCAACTCGGGGAGCAGAATCACCTGT
GCAAAACAGGACTCCTGCAGAAGTCAACTGTGTGAGTGTGATAAGGCTGC
TGCCACCTGTTTTGCTAGAAACAAGACGACCTACAATAAAAAGTACCAGT
ACTATTCCAATAAACACTGCAGAGGGAGCACCCCTCGTTGCTGAAATTCG
CCCCTCTCCCTCCCCCCCCCTAACGTTACTGGCCGAAGCCGCTTGGAATA
AGGCCGGTGTGCGTTTGTCTATATGTTATTTTCCACCATATTGCCGTCTTTT
GGCAATGTGAGGGCCCGGAAACCTGGCCCTGTCTTCTTGACGAGCATTCC
TAGGGGTCTTTCCCCTCTCGCCAAAGGAATGCAAGGTCTGTTGAATGTCGT
GAAGGAAGCAGTTCCTCTGGAAGCTTCTTGAAGACAAACAACGTCTGTAG
CGACCCTTTGCAGGCAGCGGAACCCCCCACCTGGCGACAGGTGCCTCTGC
GGCCAAAAGCCACGTGTATAAGATACACCTGCAAAGGCGGCACAACCCC
AGTGCCACGTTGTGAGTTGGATAGTTGTGGAAAGAGTCAAATGGCTCTCC
TCAAGCGTATTCAACAAGGGGCTGAAGGATGCCCAGAAGGTACCCCATTG
TATGGGATCTGATCTGGGGCCTCGGTGCACATGCTTTACATGTGTTTAGTC
GAGGTTAAAAAAACGTCTAGGCCCCCCGAACCACGGGGACGTGGTTTTCC
TTTGAAAAACACGATGATAATATGAGTGTvCTvACTCAGGTCCTGGGGTTG
CTGCTGCTGTGGCTTACAGGTGCCAGATGTGACATCCAGATGACTCAGTCT
CCAGCCTCCCTATCTGCATCTGTGGGAGAAACTGTCACCATCACATGTCGA
GCAAGTGAGAACATTTACAGTTATTTAGCATGGTATCAGCAGAAACAGGG
AAAATCTCCTCAGTTCCTGGTCTATAATGCAGAAACCTTAGCAGAAGGTG
TGCCATCAAGGTTCAGTGGCAGTGGATCAGGCAAACAGTTTTCTCTGAAG
ATCAACAGCCTGCAGCCTGAAGATTTTGGGAGTTATTACTGTCAACATCAT
TATGGTACTCATCCGACGTTCGGTGGAGGCACCAAGCTGGAAATCAAACG
GGCTGATGCTGCACCAACTGTATCCATCTTCCCACCATCCAGTGAGCAGTT
AACATCTGGAGGTGCCTCAGTCGTGTGCTTCTTGAACAACTTCTACCCCAA
AGACATCAATGTCAAGTGGAAGATTGATGGCAGTGAACGACAAAATGGC
GTCCTGAACAGTTGGACTGATCAGGACAGCAAAGACAGCACCTACAGCAT

Figure 12 (cont.)

GAGCAGCACCCTCACGTTGACCAAGGACGAGTATGAACGACATAACAGCT
ATACCTGTGAGGCCACTCACAAGACATCAACTTCACCCATTGTCAAGAGC
TTCAACAGGAATGAGTGTTAGAGACAAAGGTCCTGAGACGCCACCACCAG
CTCCCCAGCTCCATCCTATCTTCCCTTCTAAGGTCTTGGAGGCTTCCCCAC
AAGCGACCTACCACTGTTGCGGTGCTCCAAACCTCCTCCCCACCTCCTTCT
CCTCCTCCTCCCTTTCCTTGGCTTTTATCATGCTAATATTTGCAGAAAATAT
TCAATAAAGTGAGTCTTTGCACTTGA 1-678 Simian CMV promoter
679-3041 Coding sequence for mouse IgM
3042-3086 Codon-optimized Glycine serine linker
3087-3518 Coding sequence for human PLA2 group IIA
3519-4099 ECMV IRES element
4100-4804 Coding sequence for mouse kappa light chain
4805-5013 3'UTR with poly-A site

Figure 13

Parasiticidal Activity of Biocides Against C. parvum Sporozoites
(10 ug/ml 15 min)

Figure 14

P values (two-tail) for viability calculated compared to control
(no biocide 15 min 37°C)

| | P value |
|---|---|
| LF | 0.12853 |
| LFH | 2.24E-12 |
| LFB | 8.21E-13 |
| CAT | 2.53E-16 |
| IND | 1.78E-12 |
| BD1 | 4.52E-12 |
| BD2 | 2.05E-13 |
| LYZ | 0.058071 |
| PLA2 | 2.81E-07 |
| PI-PLC | 1.48E-06 |
| 3E2 | 0.942201 |
| 1E10 | 0.5672 |
| 3H2 | 0.352857 |

Figure 15
Effect of Biocides on *C. parvum* Sporozoite Infectivity for Caco-2 Human Intestinal Epithelial Cells Quantitated by Automated Immunofluorescence Microscopy

Figure 16

P values (two-tail) for neutralization calculated compared to control (no biocide)

|        | 1 ug/ml  | 10 ug/ml |
|--------|----------|----------|
| 3E2    | -        | 0.00074  |
| LF     | 0.839041 | 0.348925 |
| LFH    | 0.001001 | 0.004386 |
| LFB    | 0.005193 | 0.000397 |
| CAT    | 0.000608 | 0.00017  |
| IND    | 0.000277 | 0.000343 |
| BD1    | 0.000105 | 5.06E-05 |
| BD2    | 0.000224 | 0.000186 |
| LYZ    | 0.73383  | 0.113256 |
| PLA2   | 9.56E-05 | 0.000282 |
| PI-PLC | 0.000111 | 0.001162 |

BIOCIDES

This Application is a continuation in part of copending patent application Ser. No. 10/844,837, filed May 13, 2004, which claim priority to provisional patent application Ser. No. 60/470,841, filed May 15, 2003 and claims priority to provisional patent application 60/620,642, filed Oct. 20, 2004.

FIELD OF THE INVENTION

The present invention relates to the use of biocide (e.g., bactericidal enzyme) to neutralize pathogens. In particular, the present invention provides biocides for use in health care (e.g., human and veterinary), agriculture (e.g., animal and plant production), and food processing (e.g., water purification).

BACKGROUND OF THE INVENTION

The majority of people in the industrialized world have access to an abundance of inexpensive processed food products. The safety, quality, and wholesomeness of these products are usually unquestioned. The availability of inexpensive food products is largely a result of advances in farm mechanization and improved industries of scale in food processing and distribution operations. The mechanization of the family farm has not come without certain drawbacks however. One of the drawbacks of large-scale food processing operations, and of meat processing in particular, is the occasional contamination (e.g., bacterial, fungal, etc.) and subsequent distribution of large quantities of contaminated products sometimes with dire consequences. Food safety researchers have determined that the introduction of even a few contaminated carcasses into the production lines of large scale food processing operations is often enough to contaminate entire batches of product. The meat packing industry is particularly susceptible to carcass contamination during dehiding, evisceration, splitting, chilling, and fabrication. Further contamination of previously uncontaminated meat products may occur during grinding, processing, and transport. This type of contamination has lead to several major meat product recalls, including the recall of 24 million pounds of ground beef by the Hudson Beef Co. in 1997, and more recently, the recall of 19 million pounds of beef and related products by the ConAgra Beef Company in July 2002. (See, Recall Release, FSIS-RC-055-2002). The economic impact of food safety and spoilage is very large. USDA ERS estimates that the leading six bacterial food borne pathogens cause $2.9-6.7 billion in medical costs and lost productivity annually in the US (Buzby et al., Bacterial Foodborne Disease: Medical Costs and Productivity Losses. 1996. Food and Consumer Economics Division, Economic Research Service U.S. Department of Agriculture. Agricultural Economic Report 741)

Many meat product recalls are the result of contamination by the bacterium *Escherichia coli* O157:H7. This bacterium is commonly isolated from the gastrointestinal tract and feces of cattle. Direct contact with cattle can be a source of human infection. However, the principal route of transmission to humans is through fecal contamination of carcasses at slaughter. (J. Tuttle et al., Epidemiol Infect., 122:185-192 [1999]). Every year in the United States the O157:H7 bacterium causes about 70,000 cases of hemorrhagic diarrhea and renal disease. Children, the elderly, and the immunocompromised are most susceptible to foodborne illness caused by *Escherichia coli* O157:H7. Virulent strains of *Escherichia coli* are not the only foodborne pathogens of concern.

*Listeria monocytogenes* has emerged as another dangerous, but relatively uncommon foodborne pathogen. Despite being an uncommon source of illness, *L. monocytogenes* is ubiquitous in agricultural and food processing environments and can cause serious human and animal infections. The infection caused by *L. monocytogenes* is commonly called Listeriosis. Listeriosis occurs in sporadic and epidemic forms throughout the world. (See e.g., B. Lorber, Clin. Infect. Dis., 24(1): 1-9 [1997]; J. M. Farber et al., Microbiol. Rev., 55:476-511 [1991]; and W. F. Schlech, Clin. Infect. Dis., 31:770-775 [2000]). A multistate outbreak of Listeriosis has been reported in the United States. (Morb. Mortal. Wkly. Report, 49(50):1129-1130 [2000] erratum in Morb. Mortal. Wkly. Report, 50(6):101 [2001]). Since May 2000, 29 illnesses caused by a strain of *Listeria monocytogenes* have been identified in 10 states: New York (15 cases); Georgia (3 cases); Connecticut, Ohio, and Michigan (2 cases each); and California, Pennsylvania, TennesSee, Utah, and Wisconsin (1 case each).

Listeriosis, in its most severe form, is an invasive disease that affects immunocompromised patients and has the highest case-fatality rate of any foodborne illnesses. (B. G. Gellin et al., Amer. J. Epidemiol., 133:392-401 [1991]; D. B. Louria et al., Ann. NY Acad. Sci., 174:545-551 [1970]; J. McLauchlin, Epidemiol. Infect., 104:191-201 [1990]; V. Goulet and P. Marchetti, Scand. J. Infect. Dis., 28:367-374 [1996]; and C. J. Bula et al., Clin. Infect Dis., 20:66-72 [1995]). In immunocompetent persons, it can also cause severe disease as well as outbreaks of benign febrile gastroenteritis. (P. Aureli et al., New Engl. J. Med., 342:1236-41 [2000]). Another form of human disease is perinatal infection, which is associated with a high rate of fetal loss (including full-term stillbirths) and serious neonatal disease (J. McLauchlin, Epidemiol. Infect., 104:181-190 [1990]).

Most, perhaps all, of listeriosis in humans occurs after consumption of contaminated food (e.g., meat and cheese) products. (A. Schuchat et al., J. Amer. Med. Assoc., 267: 2041-2045 [1992]). While uncommon, Listeriosis causes about half the foodborne disease fatalities in the US each year. Additionally, many mild cases of listeriosis and inapparent *Listeria* infections go unreported. For those susceptible to listeriosis, ingestion of even small doses of *L. monocytogenes* is often sufficient for infection. About 2,500 cases of listeriosis are reported in the US each year, of these about 20% or 500 cases are fatal.

In 1989, the USDA FSIS implemented a testing program for *L. monocytogenes* in cooked meat products and adopted a zero tolerance position for *L. monocytogenes* contamination in ready to eat products. Guidelines promulgated by the American Association of Meat Processors for current Good Manufacturing Practices for Ready to Eat meat products address the need for environmental monitoring for *Listeria* as a component of HACCP programs. The ecology of *L. monocytogenes* and its increasing prevalence and/or detection in food preparation establishments has lead to major recalls of processed meat products. In October 2002 the USDA issued a recall notice, which when further expanded, constituted the largest meat product recall on record for 28 million pounds of processed turkey products (See, USDA FSIS Recall Notification Report 090-2002 EXP Recall from Pilgrims Pride Corp dba Wampler Foods Inc. Nov. 4, 2002). The recall was in response to detection of *L. monocytogenes* at multiple points in the facilities and equipment used to process the recalled turkey.

A number of approaches have been tried to increase the safety and wholesomeness of the nation's meat and agricultural products. For example, some approaches have focused on the exposing food products to one or more types of pathogen destroying processes, including ionizing radiation or ultra high temperatures and pressures. (See e.g., U.S. Pat. Nos. 5,891,490; 6,013,918; 6,086,936; and 6,165,526 etc.). U.S. Pat. No. 6,165,526 is representative of these approaches. This patent describes an UV radiation and ultra high temperature method for sterilizing food products.

A number of other approaches have focused on providing mixtures of chemicals (e.g., acids, surfactants, emulsifying agents, and organic phosphates) that inactivate bacteria and bacterial spores in food products. (See e.g., U.S. Pat. Nos. 5,550,145; and 5,618,840). U.S. Pat. No. 5,618,840, for instance, describes an antibacterial oil-in-water emulsion for inhibiting the growth of *Helicobacter pylori*.

The various compositions and methods previously described for food sterilization have certain advantages and certain other disadvantages. One disadvantage is that the manufacture and additional or large quantities of artificial chemicals to food products can be costly and logistically difficult. Moreover, the current chemical food sterilization agents are indiscriminate and are thus inappropriate for addition into food products such as cheese and yogurt that require the beneficial action of certain bacteria for their production. The addition of artificial chemical compounds to food products or subjecting the products to irradiation or temperature and pressure extremes can also produce unpleasant organoleptic qualities. Another disadvantage is the publics' generally negative perception of food irradiation and the addition of chemical additives.

Still other efforts have been directed to producing food washes to remove residual surface impurities such as waxes and pesticides sometimes acquired during food product production, processing, and transporting. For instance, U.S. Pat. No. 6,367,488 describes a chemical wash for fruits and vegetables made from surfactants, such as oleate, and alcohol ethoxylates, and neutralized phosphoric acid. While these washes are useful for removing surface contaminates and surface bacteria from solid food products, these compositions are inappropriate for sterilizing homogenized food products such as ground beef.

While each of these above-mentioned compositions and methods has particular advantages and disadvantages, the need still exists for compositions and methods that reduce the amount of pathogenic bacteria shed by feedlot animals (e.g., bovines, porcines, and the like), that induce immunity in feedlot animals to pathogens, and for edible compositions that safety destroy harmful foodborne pathogens.

A further major economic problem confronting the food processing industry is that of bacterial spoilage. In particular, dairy and processed meat products are susceptible to bacterial spoilage by organisms such as the Lactic acid bacteria (e.g., *Lactobacillus* etc.) (Kraft A A. Health hazards vs. food spoilage. Boca Raton, Fla.: CRC Press, Inc., 1992). These organisms are widely distributed in nature, and can easily outcompete other bacteria under low oxygen tension and low pH conditions that are common in processed dairy and meat foods (Stamer. Lactic acid bacteria. In: Defigueiredo M P and Splittstoesser D F eds. Westport, Conn.: AVI Publishing, 1976). Over 20% of the fruit and vegetable products harvested for human consumption are believed to be lost to post-harvest microbial spoilage (Jay, J. Modern Food Microbiology $4^{th}$ ed Van Norstand Reinhold New York, 1992).

SUMMARY OF THE INVENTION

The present invention relates to the use of biocide (e.g., bactericidal enzyme) to target pathogens. In particular, the present invention provides biocides for use in health care (e.g., human and veterinary), agriculture (e.g., animal and plant production), and food processing (e.g., water purification).

Accordingly, in some embodiments, the present invention provides a kit comprising a protein biocide active against *Cryptosporidium parvum* and instructions for using the kit to neutralize the *Cryptosporidium parvum*. In some embodiments, the protein biocide comprises at least an active portion of an enzyme (e.g., including, but not limited to, lactoferrin hydrolysate, lactoferrin b, cathelicidin, indolicidin, beta-defensin-2, deta-defensin-1, phopholipase A2, and phosphoinositol specific phospholipase C).

In other embodiments, the present invention provides a method of treating an object, subject, food product, food or animal carcass contaminated or infected with or suspected of being contaminated or infected with *Cryptosporidium parvum* (e.g., a *Cryptosporidium parvum* sporozoite) comprising providing a protein biocide active against *Cryptosporidium parvum*; and applying the protein biocide to the object, subject, food product, food, or animal carcass under conditions such that the recombinant fusion protein neutralizes the *Cryptosporidium parvum* suspected of contaminating or infecting the object, subject, food product, food or animal carcass. In preferred embodiments, the protein biocide comprises at least an active portion of an enzyme (e.g., lactoferrin hydrolysate, lactoferrin b, cathelicidin, indolicidin, beta-defensin-2, deta-defensin-1, phopholipase A2, or phosphoinositol specific phospholipase C).

In some embodiments, the object is food processing equipment, military equipment, personal protective gear, medical devices, domestic objects (e.g., an appliance or a surface), or building structures (e.g., heating and ventilation equipment, a wall or wall cavity, a swimming pool, or a plumbing system). In some embodiments, the animal carcass comprises a bovine, porcine, avian, or aquatic carcass or part thereof.

In some embodiments, the food product is drinking water. In other embodiments, the food product is a meat product, a processed meat product, vegetable, leaf, stem, seed, fruit, root, beer, wine, a dairy product, or animal feed. In some embodiments, the food product is in the process of being produced.

In some embodiments, the subject is a mammal (e.g., a ruminant (e.g., bovine), or a human). In other embodiments, the subject is an avian species. In some embodiments, the subject is suspected of being contaminated or infected with an antibiotic resistant organism. In certain embodiments, the subject is suspected of being contaminated or infected with an artificially engineered organism. In some embodiments, the subject is deceased.

DESCRIPTION OF THE FIGURES

FIG. 1 shows one contemplated retrovector construct embodiment of the present invention.

FIG. 2A shows a full size antibody with biocide linked to the N-terminus of the heavy chain. FIG. 2B shows a full size antibody with biocide linked to the C-terminus of the heavy chain. FIG. 2C shows a single chain antibody with biocide linked to the N-terminus of the light chain. FIG. 2D shows a single chain antibody with biocide linked to the C-terminus of the heavy chain. In FIGS. 2A-2D abbreviations used are as follows: LTR, long terminal repeat; EPR, extended packaging region; neo, neomycin selection marker; sCMV, simian cytomegalovirus; SP, signal peptide; X, biocide; L, (G4S)3-4 linker; HC, antibody heavy chain; IRES1, internal ribosome entry site from encephalomyocarditis virus; LC, antibody light chain; and RESE (RNA stabilization element).

FIG. 3 shows PLA2 neutralization of *C. parvum* in one embodiment of the present invention.

FIG. 5A shows a full size antibody with biocide linked to the N-terminus of the heavy chain. FIG. 5B shows a full size antibody with biocide linked to the C-terminus of the heavy chain. FIG. 5C shows a single chain antibody with biocide linked to the N-terminus of the light chain. FIG. 5D shows a single chain antibody with biocide linked to the C-terminus of the heavy chain.

FIG. 8 shows an exemplary Human CD14-PLA2 construct of the present invention (SEQ ID NO:97).

FIG. 9 shows an exemplary Human LBP-PLA2 construct of the present invention (SEQ ID NO:98).

FIG. 10 shows an exemplary Human MBL-PLA2 construct of the present invention (SEQ ID NO:99).

FIG. 11 shows an exemplary Human SP-D-PLA2 construct of the present invention (SEQ ID NO:100).

FIG. 12 shows an exemplary Mouse IgM-PLA2 construct of the present invention (SEQ ID NO:101).

FIG. 13 shows the parasticidal activity of different biocides against *C. parvum* spores.

FIG. 14 shows the P-values for the data of FIG. 13 against a no-biocide control.

FIG. 15 shows the effect of biocides on *C. parvum* sporozoite infectivity for Caco-2 human intestinal epithelial cells.

FIG. 16 shows the P-values for the data in FIG. 15.

DEFINITIONS

Figure 2:
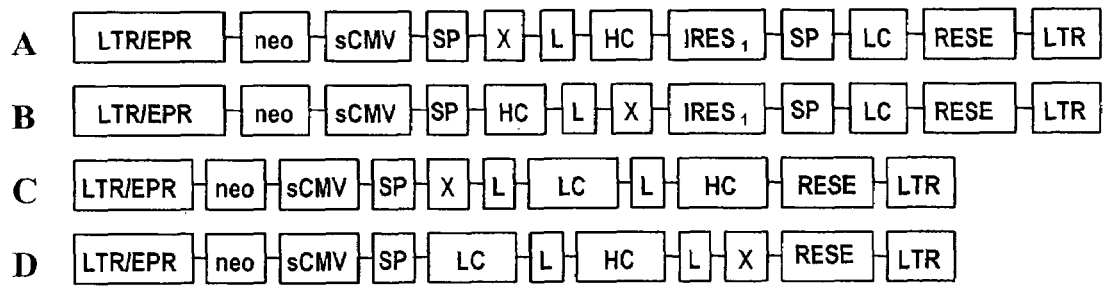
FIGS. 2A-2D show various contemplated retrovector elements used for production in mammalian cell culture of certain biocide fusions.

To facilitate an understanding of the present invention, a number of terms and phrases are defined below:

As used herein, the terms "biocide" or "biocides" refer to at least a portion of a naturally occurring or synthetic molecule (e.g., peptides) that directly kills or promotes the death and/or attenuation of (e.g., prevents growth and/or replication) of biological targets (e.g., bacteria, parasites, yeast, viruses, fungi, protozoans and the like). Examples of biocides include, but are not limited to, bactericides, viricides, fungicides, parasiticides, and the like.

As used herein, the terms "protein biocide" and "protein biocides" refer to at least a portion of a naturally occurring or synthetic peptide molecule that directly kills or promotes the death and/or attenuation of (e.g., prevents growth and/or replication) of biological targets (e.g., bacteria, parasites, yeast, viruses, fungi, protozoans and the like). Examples of biocides include, but are not limited to, bactericides, viricides, fungicides, parasiticides, and the like.

As used herein, the term "neutralization," "pathogen neutralization," "and spoilage organism neutralization" refer to destruction or inactivation (e.g., loss of virulence) of a "pathogen" or "spoilage organism" (e.g., bacterium, parasite, virus, fungus, mold, prion, and the like) thus preventing the pathogen's or spoilage organism's ability to initiate a disease state in a subject or cause degradation of a food product.

As used herein, the term "spoilage organism" refers to microorganisms (e.g., bacteria or fungi), which cause degradation of the nutritional or organoleptic quality of food and reduces its economic value and shelf life. Exemplary food spoilage microorganisms include, but are not limited to, *Zygosaccharomyces bailii, Aspergillus niger, Saccharomyces cerivisiae, Lactobacillus plantarum, Streptococcus faecalis*, and *Leuconostoc mesenteroides*.

As used herein, the term "microorganism targeting molecule" refers to any molecule (e.g., protein) that interacts with a microorganism. In preferred embodiments, the microorganism targeting molecule specifically interacts with microorganisms at the exclusion of non-microorganism host cells. Preferred microorganism targeting molecules interact with broad classes of microorganism (e.g., all bacteria or all gram positive or negative bacteria). However, the present invention also contemplates microorganism targeting molecules that interact with a specific species or sub-species of microorganism. In some preferred embodiments, microorganism targeting molecules interact with "Pathogen Associated Molecular Patterns (PAMPS)". In some embodiments, microorganism targeting molecules are recognition molecules that are known to interact with or bind to PAMPS (e.g., including, but not limited to, as CD14, lipopolysaccharide binding protein (LBP), surfactant protein D (SP-D), and Mannan binding lectin (MBL)). In other embodiments, microorganism targeting molecules are antibodies (e.g., monoclonal antibodies directed towards PAMPS or monoclonal antibodies directed to specific organisms or serotype specific epitopes).

As used herein the term "biofilm" refers to an aggregation of microorganisms (e.g., bacteria) surrounded by an extracellular matrix or slime adherent on a surface in vivo or ex vivo, wherein the microorganisms adopt altered metabolic states.

As used herein, the term "host cell" refers to any eukaryotic cell (e.g., mammalian cells, avian cells, amphibian cells, plant cells, fish cells, insect cells, yeast cells, and bacteria cells, and the like), whether located in vitro or in vivo (e.g., in a transgenic organism).

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors.

As used herein, the term "multiplicity of infection" or "MOI" refers to the ratio of integrating vectors: host cells used during transfection or infection of host cells. For example, if 1,000,000 vectors are used to transfect 100,000 host cells, the multiplicity of infection is 10. The use of this term is not limited to events involving infection, but instead encompasses introduction of a vector into a host by methods such as lipofection, microinjection, calcium phosphate precipitation, and electroporation.

As used herein, the term "genome" refers to the genetic material (e.g., chromosomes) of an organism or a host cell.

The term "nucleotide sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences, or portions thereof, of structural genes (e.g., reporter genes, selection marker genes, oncogenes, drug resistance genes, growth factors, etc.), and non-coding regulatory sequences that do not encode an mRNA or protein product (e.g., promoter sequence, polyadenylation sequence, termination sequence, enhancer sequence, etc.).

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

DNA molecules (e.g., genes) are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct the transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "exogenous gene" refers to a gene that is not naturally present in a host organism or cell, or is artificially introduced into a host organism or cell.

As used herein, the term "transgene" means a nucleic acid sequence (e.g., encoding one or more fusion protein polypeptides), which is introduced into the genome of a transgenic organism. A transgene can include one or more transcriptional regulatory sequences and other nucleic acid, such as introns, that may be necessary for optimal expression and secretion of a nucleic acid encoding the fusion protein. A transgene can include an enhancer sequence. A fusion protein sequence can be operatively linked to a tissue specific promoter, e.g., mammary gland specific promoter sequence that results in the secretion of the protein in the milk of a transgenic mammal, a urine specific promoter, or an egg specific promoter.

As used herein, the term "transgenic cell" refers to a cell containing a transgene.

A "transgenic organism," as used herein, refers to a transgenic animal or plant.

As used herein, a "transgenic animal" is a non-human animal in which one or more, and preferably essentially all, of the cells of the animal contain a transgene introduced by way of human intervention, such as by transgenic techniques known in the art. The transgene can be introduced into the cell, directly or indirectly by introduction into a precursor of the cell, by way of deliberate genetic manipulation, such as by microinjection or by infection with a recombinant virus.

Mammals are defined herein as all animals, excluding humans, which have mammary glands and produce milk.

As used herein, a "dairy animal" refers to a milk producing non-human mammal that is larger than a laboratory rodent (e.g., a mouse). In preferred embodiments, the dairy animals produce large volumes of milk and have long lactating periods (e.g., cows or goats).

As used herein, the term "plant" refers to either a whole plant, a plant part, a plant cell, or a group of plant cells, including plants that are actively growing (e.g. in soil) and those that have been harvested. The class of plants used in methods of the invention is generally as broad as the class of higher plants amenable to transformation techniques, including both monocotyledonous and dicotyledonous plants. It includes plants of a variety of ploidy levels, including polyploid, diploid and haploid.

As used herein, a "transgenic plant" is a plant, preferably a multi-celled or higher plant, in which one or more, and preferably essentially all, of the cells of the plant contain a transgene introduced by way of human intervention, such as by transgenic techniques known in the art.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "protein of interest" refers to a protein encoded by a nucleic acid of interest.

As used herein, the term "native" (or wild type) when used in reference to a protein refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acids are nucleic acids present in a form or setting that is different from that in which they are found in nature. In contrast, non-isolated nucleic acids are nucleic acids such as DNA and RNA that are found in the state in which they exist in nature.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain translated from the mRNA. The DNA or RNA sequence thus codes for the amino acid sequence.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5× SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5× SSPE (43.8 g/l NaCl, 6.9 g/l NaH$_2$PO$_4$ H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5× SSPE, 0.1 % SDS at 42° C. when a probe of about 500 nucleotides in length is employed.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include, but are not limited to, the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp.16.9-16.15.

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horseradish peroxidase.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review See e.g., Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]). In preferred embodiments, inducible retroviral promoters are utilized.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., mammillary gland) in the relative absence of expression of the same nucleotide sequence(s) of interest in a different type of tissue (e.g., liver).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element which is capable of directing selective expression of a nucleotide sequence of interest in a specific type of cell in the relative absence of expression of the same nucleotide sequence of interest in a different type of cell within the same tissue (e.g., cells infected with retrovirus, and more particularly, cells infected with BLV or HTLV). The term "cell type specific" when applied to a regulatory element also means a regulatory element capable of promoting selective expression of a nucleotide sequence of interest in a region within a single tissue.

The cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.), which is different from the level of transcription of the operably linked nucleic acid sequence in the absence of the stimulus.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to 104 copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" or "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which is incorporated herein by reference) and woodchuck mRNA processing enhancer (WPRE; WO 99/14310, incorporated herein by reference).

As used herein, the term "polycistronic" refers to an mRNA encoding more than one polypeptide chain (See, e.g., WO 93/03143, WO 88/05486, and European Pat. No. 117058, each of which is incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Vectors incorporating IRESs may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter (e.g., the inducible promoters of the present invention), which may be preferable depending on the use. The polycistronic message cassette can further comprise a cDNA or genomic DNA (gDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell.

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells that are susceptible to infection by the retrovirus. Through well-known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola), which is associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

A "subject" is an animal such as vertebrate, preferably a mammal, more preferably a human or a bovine. Mammals, however, are understood to include, but are not limited to, murines, simians, humans, bovines, cervids, equines, porcines, canines, felines etc.).

An "effective amount" is an amount sufficient to effect beneficial or desired results. An effective amount can be administered in one or more administrations, "Co-administration" refers to administration of more than one agent or therapy to a subject. Co-administration may be concurrent or, alternatively, the chemical compounds described herein may be administered in advance of or following the administration of the other agent(s). One skilled in the art can readily determine the appropriate dosage for co-administration. When co-administered with another therapeutic agent, both the agents may be used at lower dosages. Thus, co-administration is especially desirable where the claimed compounds are used to lower the requisite dosage of known toxic agents.

As used herein, the term "toxic" refers to any detrimental or harmful effects on a cell or tissue.

A "pharmaceutical composition" is intended to include the combination of an active agent with a carrier, inert or active, making the composition suitable for diagnostic or therapeutic use in vivo, in vivo or ex vivo.

As used herein, the term "pharmaceutically acceptable carrier" encompasses any of the standard pharmaceutical carriers, such as a phosphate buffered saline solution, water, and an emulsion, such as an oil/water or water/oil emulsion, and various types of wetting agents. The compositions also can include stabilizers and preservatives. For examples of carriers, stabilizers and adjuvants see Martin, Remington's Pharmaceutical Sciences, 15th Ed., Mack Publ. Co., Easton, Pa. (1975).

"Pharmaceutically acceptable salt" as used herein, relates to any pharmaceutically acceptable salt (acid or base) of a compound of the present invention, which, upon administration to a recipient, is capable of providing a compound of this invention or an active metabolite or residue thereof. As is known to those of skill in the art, "salts" of the compounds of the present invention may be derived from inorganic or organic acids and bases. Examples of acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds of the invention and their pharmaceutically acceptable acid.

As used herein, the term "nutraceutical," refers to a food substance or part of a food, which includes a fusion protein. Nutraceuticals can provide medical or health benefits, including the prevention, treatment, or cure of a disorder. The transgenic protein will often be present in the nutraceutical at a concentration of at least 100 µg/kg, more preferably at least 1 mg/kg, most preferably at least 10 mg/kg. A nutraceutical can include the milk of a transgenic animal.

As used herein, the term "purified" or "to purify" refers to the removal of undesired components from a sample. As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces, and Rickettsia*. All forms of bacteria are included within this definition including cocci, *bacilli*, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., C V Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red. In some embodiments, the bacteria are those capable of causing disease (pathogens) and those that cause product degradation or spoilage.

As used herein, the term "antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Inmunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]). In other embodiments, suitable monoclonal antibodies, including recombinant chimeric monoclonal antibodies and chimeric monoclonal antibody fusion proteins are prepared as described herein.

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity. In some embodiments, monoclonal antibodies are generated using the ABL-MYC method (See e.g., U.S. Pat. Nos. 5,705,150 and 5,244,656, each of which is herein incorporated by reference) (Neoclone, Madison, Wis.). ABL-MYC is a recombinant retrovirus that constitutively expresses v-abl and c-myc oncogenes. When used to infect antigen-activated splenocytes, this retroviral system rapidly induces antigen-specific plasmacytomas. ABL-MYC targets antigen-stimulated (Ag-stimulated) B-cells for transformation.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen-binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

GENERAL DESCRIPTION OF THE INVENTION

One embodiment of the present invention provides compositions and methods for treating and/or preventing illnesses in animals caused by pathogens. More particularly, the present invention provides therapeutic and prophylactic compositions directed to combating bacterial, parasitical, and fungal infections in humans and other animals (e.g., feedlot and domestic animals such as cows, chickens, turkeys, pigs, and sheep).

In preferred embodiments, the present invention provides fusion proteins comprising microorganism targeting molecules (e.g., including, but not limited to, monoclonal antibody and innate immune system receptors) directed against bacterial, parasitic, and fungal pathogens and methods of using and creating these molecules. In some of these embodiments, the antibodies are chimeras (e.g., murine-bovine). The present invention is not limited however to providing fusion proteins or chimeras.

In other embodiments, the present invention provides chimeric monoclonal antibodies directed against foodborne bacterial, protozoan and parasitic pathogens. However, the bacterial pathogens need not be foodborne (e.g., gastrointestinal). For example, additional embodiments are directed to providing therapeutic compositions and methods to combat other bacterial infections via other possible routes of transmission (e.g., respiratory, salivary, fecal-oral, skin-to-skin, bloodborne, genital, urinary, eye-to-eye, zoonotic, etc.). Moreover, other aspects of the present invention provide chimeric monoclonal antibodies against viruses, prions, fungal, protozoan and other parasitic and pathogenic sources of illness.

In addition to the compositions and methods discussed above, the present invention further provides chimeric recombinant monoclonal antibody fusion proteins. In some of these embodiments, the fusion proteins comprise one or more portions of an immunoglobulin and a portion of a biocide molecule, such as bactericides, viricides, fungicides, parasiticides, and the like. In preferred embodiments, the present invention provides antibody biocide fusion proteins, wherein the biocide component comprises a bactericidal enzyme such as human lysozyme, phospholipase A2 (groups I, II, V, X, and XII), lactoferrin, lactoperoxidase, and bacterial permeability increasing protein. In additional embodiments, the present provides fusion proteins comprising immune system complement proteins including cytokines such as the interferons (e.g., IFN-α, IFN-β, and IFN-γ) and the tumor necrosis factors (e.g., TNF-α, and TNF-β)and defensins. In preferred embodiments, the antibody portion of these fusion proteins binds specifically to a foodborne bacterial pathogen (e.g., *E. coli* O 157:H7, *Listeria monocytogenes*, *Campylobacter jejuni*, and the like).

The present invention also provides compositions comprising fusion proteins in an edible carrier such as whey protein. Preferred methods of using these compositions include, but are not limited to, food additives for human and animal (e.g., bovines) consumption, carcass decontaminating compounds used during processing and finishing feedlot animal (e.g., bovine) carcasses and poultry, as well as pharmaceutical compositions for both human and veterinary medicine. The present invention is not limited to the uses specifically recited herein.

In some embodiments, suitable food additive formulations of the present compositions include, but are not limited to, compositions directly applied to food products such as processed meat slices and dairy products in the form of sprays, powders, injected solutions, coatings, gels, rinses, dips, films (e.g., bonded), extrusions, among other known formulations.

Likewise, the present invention further provides compositions (e.g., rinses, sprays, and the like) for sanitizing food-processing, medical, military or household equipment. For example, some preferred embodiments of the present invention provide compositions for disinfecting meat-processing equipment. In this regard, the present invention contemplates that a number of food (e.g., meat) processors will benefit from using the compositions and methods of the present invention in their operations. In this regard, the present invention contemplates providing compositions to the entire range of meat processing operations from the largest commercial slaughterhouses to individual consumers.

Those skilled in the art will appreciate that the compositions disclosed herein can be readily formulated to include additional compounds common in the pharmaceutical arts such as, excipients, extenders, preservatives, and bulking agents depending on the intended use of a composition. Furthermore, ingestible formulations of these compositions may also comprise any material approved by the United States Department of Agriculture (USDA) for incorporation into food products such as substances that are generally recognized as safe (GRAS) including, food additives, flavorings, colorings, vitamins, minerals, and phytonutrients. The term phytonutrients as used herein, refers to organic compounds isolated from plants having biological effects including, but not limited to, compounds from the following classes of molecules: isoflavonoids, oligomeric proanthcyanidins, indol-3-carbinol, sulforaphone, fibrous ligands, plant phytosterols, ferulic acid, anthocyanocides, triterpenes, omega ⅗ fatty acids, polyacetylene, quinones, terpenes, cathechins, gallates, and quercitin.

In still further embodiments, the fusion proteins of the present invention are purified from the lactations of transgenic non-human mammals such as, cows, pigs, sheep, and goats. In particularly preferred embodiments, the transgenic animal is a cow. Consequently, the present invention further provides novel genetic constructs and methods of producing transgenic animals that express the compositions of the present invention in their lactation. The present invention also provides methods of inducing transgenic animals (e.g., bovines) to lactate upon maturation.

The present invention also provides methods of stably transfecting cell lines (e.g., mammalian, plant, insect, and amphibian) with encoding the fusion proteins disclosed herein. In preferred embodiments, the constructs of the present invention allow complex multicistronic gene constructs to be stably inserted into cells (e.g., mammalian, bacteria, fungal cells, plant, etc). The production of fusion proteins in mammalian cell lines (or in transgenic mammals) allows for their proper assembly and processing. Another method suitable for use in some embodiments of the present invention is protein production in mammalian tissue culture bioreactors.

Monoclonal antibodies are typically produced in mammalian cells to ensure correct processing, however mammalian tissue culture bioreactors are often expensive to operate thus placing products beyond mass applications. The ability to manufacture monoclonals in the milk of transgenic animals (e.g., bovines) is contemplated to expand the scope of monoclonal antibodies typically from individual medicine to applications for large populations. Production of the disclosed compositions in the milk of transgenic mammals (e.g., bovines) provides large quantities for economical distribution to food safety and processing operations. For instance, in preferred embodiments, the present invention contemplates that at reasonable expression levels of about one gram per liter of milk, a herd of 100 transgenic cows will produce about a metric ton of recombinant protein per year. This enables production of recombinant monoclonals at 100 fold less cost than in cell culture bioreactors. Accordingly, in preferred embodiments the present invention provides methods of creating transgenic bovines that produce the compositions of the present invention in their lactation. The present invention also provides methods of isolating and purifying the compositions of the present invention from the lactation of milk producing herd animals (e.g., cows, sheep, and goats and the like).

In still further embodiments, the present invention provides fusion protein enriched colostrum, or colostrum like products, for use as milk substitutes and nutritional supplements for nursing mammals and in particular for nursing feedlot animals. In preferred embodiments, these compositions comprise the microorganism targeting molecule fusion proteins of the present invention. The present invention also contemplates that introducing these compositions to nursing feedlot animals will reduce the colonization of the animal's gastrointestinal tract by pathogenic organisms such as *E. coli* O157:H7 and *Listeria monocytogenes* and *Cryptosporidium parvum*. Furthermore, the compositions may be added to feeds to control diseases such as coccidiosis, which are common in both cattle and chicken feeding operations. In particular, providing a fusion protein enriched milk replacer or colostrum supplement reduces the load of *E. coli* O157:H7 in the gastrointestinal tract of the neonate and specifically places the targeted pathogenic organisms at a competitive disadvantage in relation to normal gastrointestinal flora. The present invention further contemplates inducing a protective immune response in animals fed the preset fusion protein enriched colostrums and colostrum-like compositions. Accordingly, additional preferred embodiments of the present invention are directed to inducing an immune response in animals feed the present compositions.

The present invention provides compositions and methods directed against foodborne pathogens such as, but not limited to, *E. coli* O157:H7, *Listeria monocytogenes, Campylobacter jejuni, Clostridium botulinum, Clostridium perfringens, Staphylococcus aureus, Staphylococcus epidermidis, Staphylococcus pneumoniae, Staphylococcus saprophyticus, Staphylococcus mutans, Shigella dysenteriae, Salmonella typhi, Salmonella paratyphi, Salmonella enteritidis, Cryptosporidium parvum*, fungi, and the like. The present invention further provides composition and methods directed against food spoilage organisms such as, but not limited to, bacteria (e.g., *Lactobacillus, Leuconostoc, Pediococcus*, and *Streptococcus* and fungi (e.g., *Monilia, Trichoderma, Crinipellis, Moniliophthora, Phytophthora, Botrytis*, and *Fusarium*).

The present invention also provides compositions and methods directed against protozoans, particularly, apicomplexan protozoans including, but not limited to, coccidian, cryptosporidian, toxoplasman, malarial and trypanosomatid protozoans.

In preferred embodiments, the compositions of the present invention comprise a targeting molecule, for example an immunoglobulin subunit (or portion thereof), a biocide molecule (or portion thereof) such as, a bactericidal enzyme, (e.g., lysozyme), and a linker that connects the targeting molecule and the biocide molecule. In other preferred embodiments, the compositions further comprise a signaling molecule or sequence that predictably directs the composition to an intracellular or extracellular location.

In certain embodiments, the present invention provides broad spectrum antimicrobials. Broad spectrum antimicrobials find use as a preventative tool where the identity of possible food contaminants is unknown, and new organisms can emerge as serious threats. Broad spectrum antimicrobials are also well suited for use in medicine and biodefense in confronting an infection of unknown etiology.

Broad spectrum antimicrobials take advantage of the innate immune system, which provides an important front line defense through receptors on specialized cells (e.g., macrophages, neutrophils) that are capable of binding the vast majority of microbes to which these body surfaces are exposed. In some embodiments, recognition molecules such as CD14, lipopolysaccharide binding protein (LBP), surfactant protein D (SP-D), Toll receptors, and Mannan binding lectin (MBL) that recognize and bind to Pathogen Associated Molecular Patterns (PAMPs) common to many organisms are used as the targeting portion of fusion proteins of the present invention.

In other embodiments, broadly reactive monoclonal antibodies that bind to PAMPS are use as the targeting portion of the fusion proteins of the present invention. In preferred embodiments, biocidal enzymes are delivered in high concentrations to the surface of bacteria by expressing the two components, a microorganism targeting molecule and a biocidal payload as a fusion protein.

In still further embodiments, IgM (e.g., for increased avidity of binding to repetitive PAMPs) and secretory IgA (e.g., for greater stability in harsh environments) are used and instead of attaching the biocide directly to the targeting molecule, it is attached to the J chain that is used to assemble both pentameric IgM and dimeric IgA. By using components of the innate immune system the present invention provides antimicrobials that function effectively ex vivo (e.g., in food safety settings), as well as in vivo (e.g., in clinical medicine and veterinary medicine), which can confront a broad range of bacteria through the broad affinity of the innate recognition. Furthermore, because the recognition targets bacterial features that are essential to bacterial invasion and attachment, resistance is very unlikely to occur. The present invention thus provides a novel class of antimicrobials that find use in a variety of settings.

I. Immunoglobulins

Immunoglobulins (antibodies) are proteins generated by the immune system to provide a specific molecule capable of complexing with an invading molecule commonly referred to as an antigen. Natural antibodies have two identical antigen-binding sites, both of which are specific to a particular antigen. The antibody molecule recognizes the antigen by complexing its antigen-binding sites with areas of the antigen termed epitopes. The epitopes fit into the conformational architecture of the antigen-binding sites of the antibody, enabling the antibody to bind to the antigen.

The immunoglobulin molecule is composed of two identical heavy and two identical light polypeptide chains, held together by interchain disulfide bonds. Each individual light and heavy chain folds into regions of about 110 amino acids, assuming a conserved three-dimensional conformation. The light chain comprises one variable region (termed $V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions, $V_L$ and $V_H$, associate to form an "$F_V$" area that contains the antigen-binding site.

The variable regions of both heavy and light chains show considerable variability in structure and amino acid composition from one antibody molecule to another, whereas the constant regions show little variability. Each antibody recognizes and binds an antigen through the binding site defined by the association of the heavy and light chain, variable regions into an $F_V$ area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDRs from a light chain and the three CDRs from a corresponding heavy chain form the antigen-binding site.

Cleavage of naturally occurring antibody molecules with the proteolytic enzyme papain generates fragments that retain their antigen-binding site. These fragments, commonly known as Fab's (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Monoclonal antibodies against target antigens (e.g., a cell surface protein, such as receptors) are produced by a variety of techniques including conventional monoclonal antibody methodologies such as the somatic cell hybridization techniques of Kohler and Milstein, Nature, 256:495 (1975). Although in some embodiments, somatic cell hybridization procedures are preferred, other techniques for producing monoclonal antibodies are contemplated as well (e.g., viral or oncogenic transformation of B lymphocytes).

The preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Human monoclonal antibodies (mAbs) directed against human proteins can be generated using transgenic mice carrying the complete human immune system rather than-the mouse system. Splenocytes from the transgenic mice are immunized with the antigen of interest, which are used to produce hybridomas that secrete human mAbs with specific affinities for epitopes from a human protein. (See e.g., Wood et al., WO 91/00906, Kucherlapati et al., WO 91/10741; Lonberg et al., WO 92/03918; Kay et al., WO 92/03917 [each of which is herein incorporated by reference in its entirety]; N. Lonberg et al., Nature, 368:856-859 [1994]; L. L. Green et al., Nature Genet., 7:13-21 [1994]; S. L. Morrison et al., Proc. Nat. Acad. Sci. USA, 81:6851-6855 [1994]; Bruggeman et al., Immunol., 7:33-40 [1993]; Tuaillon et al., Proc. Nat. Acad. Sci. USA, 90:3720-3724 [1993]; and Bruggernan et al. Eur. J. Immunol., 21:1323-1326 [1991]).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies. (See e.g., Sastry et al., Proc. Nat. Acad. Sci. USA, 86:5728 [1989]; Huse et al., Science, 246: 1275 [1989]; and Orlandi et al., Proc. Nat. Acad. Sci. USA, 86:3833 [1989]). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and the PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies. (See e.g., Larrick et al., Biotechniques, 11:152-156 [1991]). A similar strategy can also been used to amplify human heavy and light chain variable regions from human antibodies (See e.g., Larrick et al., Methods: Companion to Methods in Enzymology, 2:106-110 [1991]).

In one embodiment, RNA is isolated from B lymphocytes, for example, peripheral blood cells, bone marrow, or spleen preparations, using standard protocols (e.g., U.S. Pat. No. 4,683,292 [incorporated herein by reference in its entirety]; Orlandi, et al., Proc. Nat. Acad. Sci. USA, 86:3833-3837 [1989]; Sastry et al., Proc. Nat. Acad. Sci. USA, 86:5728-5732 [1989]; and Huse et al., Science, 246:1275 [1989]). First strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation ingenerating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries, examples of methods and reagents particularly amenable for use in generating a variegated antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809 [each of which is herein incorporated by refernce in its entirety]; Fuchs et al., Biol. Technology, 9:1370-1372 [1991]; Hay et al., Hum. Antibod. Hybridomas, 3:81-85 [1992]; Huse et al., Science, 46:1275-1281 [1989]; Hawkins et al., J. Mol. Biol., 226:889-896 [1992]; Clackson et al., Nature, 352:624-628 [1991]; Gram et al., Proc. Nat. Acad. Sci. USA, 89:3576-3580 [1992]; Garrad et al., Bio/Technolog, 2:1373-1377 [1991]; Hoogenboom et al., Nuc. Acid Res., 19:4133-4137 [1991]; and Barbas et al., Proc. Nat. Acad. Sci. USA, 88:7978 [1991]. In certain embodiments, the V region domains of heavy and light chains can be expressed on the same polypeptide, joined by a flexible linker to form a single-chain Fv fragment, and the scFV gene subsequently cloned into the desired expression vector or phage genome.

As generally described in McCafferty et al., Nature, 348: 552-554 (1990), complete $V_H$ and $V_L$ domains of an antibody, joined by a flexible linker (e.g., $(Gly_4-Ser)_3$) can be used to produce a single chain antibody which can render the display package separable based on antigen affinity. Isolated scFV antibodies immunoreactive with the antigen can subsequently be formulated into a pharmaceutical preparation for use in the subject method.

Once displayed on the surface of a display package (e.g., filamentous phage), the antibody library is screened with the target antigen, or peptide fragment thereof, to identify and isolate packages that express an antibody having specificity for the target antigen. Nucleic acid encoding the selected antibody can be recovered from the display package (e.g., from the phage genome) and subcloned into other expression vectors by standard recombinant DNA techniques.

Specific antibody molecules with high affinities for a surface protein can be made according to methods known to those in the art, e.g., methods involving screening of libraries U.S. Pat. Nos. 5,233,409 and 5,403,484 (both incorporated herein by reference in their entireties). Further, the methods of these libraries can be used in screens to obtain binding determinants that are mimetics of the structural determinants of antibodies.

In particular, the Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence information, by a modeling procedure using previously determined three-dimensional structures from other antibodies obtained from NMR studies or crytallographic data.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allows the creation of large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages. Phage display libraries are known in the art.

Other techniques include affinity chromatography with an appropriate "receptor," e.g., a target antigen, followed by identification of the isolated binding agents or ligands by conventional techniques (e.g., mass spectrometry and NMR). Preferably, the soluble receptor is conjugated to a label (e.g., fluorophores, colorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library. (See e.g., W. C. Still et al., WO 94/08051 incorporated herein by reference in its entirety). In general, this method features the use of inert but readily detectable tags that are attached to the solid support or to the compounds. When an active compound is detected, the identity of the compound is determined by identification of the unique accompanying tag. This tagging method permits the synthesis of large libraries of compounds that can be identified at very low levels among to total set of all compounds in the library.

The term modified antibody is also intended to include antibodies, such as monoclonal antibodies, chimeric antibodies, and humanized antibodies which have been modified by, for example, deleting, adding, or substituting portions of the antibody. For example, an antibody can be modified by deleting the hinge region, thus generating a monovalent antibody. Any modification is within the scope of the invention so long as the antibody has at least one antigen binding region specific.

Chimeric mouse-human monoclonal antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 [each of which is herein incorporated by reference in its entirety]; Better et al., Science, 240:1041-1043 [1988]; Liu et al., Proc. Nat. Acad. Sci. USA, 84:3439-3443 [1987]; Liu et al., J. Immunol., 139:3521-3526 [1987]; Sun et al., Proc. Nat. Acad. Sci. USA, 84:214-218 [1987]; Nishimura et al., Canc. Res., 47:999-1005 [1987]; Wood et al., Nature, 314:446-449 [1985]; and Shaw et al., J. Natl. Cancer Inst., 80:1553-1559 [1988]).

The chimeric antibody can be further humanized by replacing sequences of the Fv variable region that are not directly involved in antigen binding with equivalent sequences from human Fv variable regions. General reviews of humanized chimeric antibodies are provided by S. L. Morrison, Science, 229:1202-1207 (1985) and by Oi et al., Bio. Techniques, 4:214 (1986). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-$GPII_bIII_a$ antibody producing hybridoma. The recombinant DNA encoding the chimeric antibody, or fragment thereof, can then be cloned into an appropriate expression vector.

Suitable humanized antibodies can alternatively be produced by CDR substitution (e.g., U.S. Pat. No. 5,225,539 (incorporated herein by reference in its entirety); Jones et al., Nature, 321:552-525 [1986]; Verhoeyan et al., Science, 239: 1534 [1988]; and Beidler et al., J. Immunol., 141:4053 [1988]). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs; using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In preferred embodiments, the fusion proteins include a monoclonal antibody subunit (e.g., a human, murine, or bovine), or a fragment thereof, (e.g., an antigen binding fragment thereof). The monoclonal antibody subunit or antigen binding fragment thereof can be a single chain polypeptide, a dimer of a heavy chain and a light chain, a tetramer of two heavy and two light chains, or a pentamer (e.g., IgM). IgM is a pentamer of five monomer units held together by disulfide bonds linking their carboxyl-terminal (Cμ4/Cμ4) domains and Cμ3/Cμ3 domains. The pentameric structure of IgM provides 10 antigen-binding sites, thus serum IgM has a higher valency than other types of antibody isotypes. With its high valency, pentameric IgM is more efficient than other antibody isotypes at binding multidimensional antigens (e.g., viral particles and red blood cells. However, due to its large pentameric structure, IgM does not diffuse well and is usually found in low concentrations in intercellular tissue fluids. The J chain of IgM allows the molecule to bind to receptors on secretary cells, which transport the molecule across epithelial linings to the external secretions that bathe the mucosal surfaces. In some embodiments, of the present invention take advantage of the low diffusion rate of pentameric IgM to help concentrate the fusion proteins of present invention at a site of interest. In preferred embodiments, monoclonal IgM, and fusion and chimeric proteins thereof, are directed to destroying *Cryptosporidium parvum* and other types of parasitic pathogens.

In some embodiments, an IgA is utilized to make a directed biocide. IgA's are preferably produced using either one, two or three constructs. IgA made by use of two or three retrovector constructs. For example, a retroviral construct can be produced in which the J-chain expression is driven by the long terminal repeat (LTR) promoter, and expression of a heavy chain and light chain separated by an IRES sequence is driven by an internal promoter. In another example, the heavy chain and light chain are provided in one vector and the J chain is provided in another vector. In another example, a third construct expressing the secretory component truncated form from poly IgR is provided.

In still other embodiments, secretion of a directed biocide is enhanced by transfecting a cell producing a directed biocide with a vector (e.g., a retroviral vector) that expressed secretory component. See U.S. Pat. No. 6,300,104; Koteswarra and Morrison, Proc. Natl. Acad. Sci. USA 94:6364-68 (1997).

In some preferred embodiments, the monoclonal antibody is a murine antibody or a fragment thereof. In other preferred embodiments, the monoclonal antibody is a bovine antibody or a fragment thereof. For example, the murine antibody can be produced by a hybridoma that includes a B cell obtained from a transgenic mouse having a genome comprising a heavy chain transgene and a light chain transgene fused to an immortalized cell. The antibodies can be of various isotypes, including, but not limited to: IgG (e.g., IgG1, IgG2, IgG2a, IgG2b, IgG2c, IgG3, IgG4); IgM; IgA1; IgA2; $IgA_{sec}$; IgD; and IgE. In some preferred embodiments, the antibody is an IgG isotype. In other preferred embodiments, the antibody is an IgM isotype. The antibodies can be full-length (e.g., an IgG1, IgG2, IgG3, or IgG4 antibody) or can include only an antigen-binding portion (e.g., a Fab, F(ab')$_2$, Fv or a single chain Fv fragment).

In preferred embodiments, the immunoglobulin subunit of the fusion proteins is a recombinant antibody (e.g., a chimeric or a humanized antibody), a subunit, or an antigen binding fragment thereof (e.g., has a variable region, or at least a complementarity determining region (CDR)).

In preferred embodiments, the immunoglobulin subunit of the fusion protein is monovalent (e.g., includes one pair of heavy and light chains, or antigen binding portions thereof). In other embodiments, the immunoglobulin subunit of the fusion protein is a divalent (e.g., includes two pairs of heavy and light chains, or antigen binding portions thereof). In preferred embodiments, the transgenic fusion proteins include an immunoglobulin heavy chain or a fragment thereof (e.g., an antigen binding fragment thereof).

In still other embodiments, the fusion proteins and/or or recombinant antibodies comprise an immunoglobulin having only heavy chains such as the HCAbs found in certain *Camelidae* (e.g., camels, dromedaries, and llamas) species, spotted ratfish, and nurse shark. While the present invention is not limited to any particular mechanisms, the present invention contemplates that there are differences between conventional antibodies and HCAbs in both the $V_H$ and $C_H$ regions. For instance, as reported by Muyldermans et al. and Nguyen et al., the sequences of HCAbs variable domains ($V_HH$) differ significantly from those of conventional antibodies ($V_H$). (S. Muyldermans et al., Protein, Eng., 7:1129-1135 [1994]; V. K. Nguyen et al., J. Mol. Biol., 275:413-418 [1998]; and V. K. Nguyen et al., Immunogenetics DOI 10.1007/s00251-002-0433-0 [2002]). Additionally, HCAbs lack the first domain of the constant region ($C_H$); the matured $V_HH$-DJ is directly joined to the hinge region. Separate sets of V and C genes encode conventional antibodies and HCAbs, however, conventional antibodies and HCAbs have some common D genes and appear to have identical $J_H$ regions. (V. K. Nguyen et al., EMBO J., 19:921-930 [2000]; and V. K. Nguyen et al., Adv. Immunol., 79:261-296 [2001]).

In yet other embodiments, IgM is used as the microorganism targeting molecule. IgMs bind with multiple epitopes, effectively enhancing the avidity of the binding. The genes for both SP-D and MBL of these molecules have been sequenced and both have been produced as recombinant molecules in full or truncated forms (Shrive et al., J Mol Biol 2003; 331: 509-23; Arora et al., J Biol Chem 2001; 276:43087-94).

In other embodiments, the microorganism targeting molecules are monoclonal antibodies that target PAMPs. In some embodiments, the monoclonal antibodies utilize the multimeric structure of IgM and IgA. The repetitive structure of many PAMPs allows antibodies to bind to two identical epitopes on one molecule or on separate molecules (cross-linking) on the bacterial surface. This type of interaction results in an overall higher binding energy per antibody molecule than the engagement of one single arm of the immunoglobulin in the binding; for the antibody to detach, both binding sites would have to be released at once. The avidity is proportionally higher for IgA, which is a dimer, bearing a total of 4 binding sites, or IgM which usually is a pentamer, having 10 binding sites.

Packing plants are harsh environments; secretory IgA is adapted to function in the gastrointestinal tract and its dimeric configuration is supported by a portion of the secretory component that assists its membrane transport. Thus IgM and IgA may offer advantages as targeting molecules over IgG. In certain embodiments, the fact that they are linked by a J chain, and in the case of IgA coexpressed with secretory component, allows for attaching the payload biocide to these auxiliary chains instead of to the Fc portion of the immunoglobulin itself. Accordingly, in some embodiments, the immunoglobulin J-chain is used as a microorganism targeting molecule.

In some embodiments, a system of hybridoma-like antibody preparation, developed by Neoclone (Madison, Wis.), is used in the production of monoclonal antibodies. Splenocytes from immunized mice are immortalized using a retrovector-mediated introduction of the abl-myc genes. On reintroduction into recipient mice one dominant immortalized B cell clone (plasmacytoma) outgrows all others and produces a monoclonal antibody in the ascitic fluid. The B cell clone can be harvested with the ascitic fluid that contains high concentration of monoclonal antibody. This process can be completed in 8-10 weeks.

II. Innate System Receptors

In some embodiments of the present invention, innate immunity receptors are used as microorganism targeting molecules due to their high affinity of interaction with a multitude of microorganisms. These receptors are all highly conserved structures across species, even across classes (Ezekowitz R A B and Hoffmann J A. Innate Immunity. Totowa, N.J.: HUmana Press, 2003). Many of these evolutionarily ancient receptors are found in Invertebrae (Aderem A and Ulevitch R J. Nature 2000; 406:782-7). Preferred microorganism targeting molecules are those that exist as soluble molecules in circulation.

In some embodiments, the microorganism targeting molecule is CD14, found on monocytes/macrophages and neutrophils (Haziot et al., J Immunol 1988; 141:547-52). This molecule exists as both a membrane-bound form, with a GPI anchor, and as a soluble form. Both versions of CD14 bind LPS with high affinity. The reported dissociation constant for LPS binding to CD14 is $K_D$ 3-7×10$^{-8}$ M (Tobias et al., J Biol Chem 1995; 270:10482-8). Haziot and co-workers have produced recombinant soluble human CD14 and have used it to study the binding to LPS (Haziot et al., J Immunol 1995; 154:6529-32), showing that soluble CD14 binds LPS under various conditions. LPS is one of the main components of the cell wall of Gram-negative bacteria. CD14 also binds to peptidoglycan structures with high affinity (Kd=25 nM) (Dziarski, Cell Mol Life Sci 2003; 60:1793-804; Dziarski et al., Chem Immunol 2000; 74:83-107; Dziarski et al., Infect Immun 2000; 68:5254-60.). Peptidoglycan (PGN) structures make up a substantial portion of the cell wall of Gram-negative and Gram-positive bacteria. In addition, CD14 binds to lipoteichoic acid on Gram-positive bacteria, lipoarabinomannan of mycobacteriae, lipoproteins from spirochetes and mycobacteriae, and others (Dziarski, Cell Mol Life Sci 2003; 60:1793-804). CD14 is a highly versatile receptor that interacts with an impressive variety of different bacteria.

In other embodiments, the microorganism targeting molecule is the LPS-binding protein (LBP) (Tobias et al., J Exp Med 1986; 164:777-93). LBP is an acute phase protein that is released into circulation upon a bacterial infection with Gram-negative bacteria or exposure to LPS. LBP can bind circulating or bound LPS, and through this interaction inhibit LPS-related septic shock (Lamping et al., J Clin Invest 1998; 101:2065-71). LBP can inhibit LPS-induced signaling by blocking LPS transfer from CD14 to Toll like receptor 4 (Thompson et al., J Biol Chem 2003; 278:28367-71). In addition, LBP is capable of removing LPS from mCD14 with high efficiency, indicating that LBP binds LPS more strongly than CD14. Separate studies aimed at comparing binding efficiencies between LPS, LBP, and CD14 have confirmed that LBP binds LPS with a roughly ten-fold higher affinity $K_D$ 3.5× 10$^{-9}$ M (Tobias et al., J Biol Chem 1995; 270:10482-8) than CD14. LBP has been cloned, sequenced and expressed by various groups (Schumann et al., Science 1990; 249:1429-31; Theofan et al., J Immunol 1994; 152:3623-9; Thompson et al., J Biol Chem 2003; 278:28367-71).

In still further embodiments, the microorganism targeting molecule is a member of the collectins, also called defense collagens (Van De Wetering et al., Eur J Biochem 2004; 271:1229-49). Surfactant protein D (SP-D) has been shown to interact with rough and smooth LPS on bacterial surfaces (Clark et al., Microbes Infect 2000; 2:273-8; Lawson and Reid, Immunol Rev 2000; 173:66-78) and therefore can target Gram-negative microorganisms. In other embodiments, mannan-binding lectin (MBL), from this family, which is known to target peptidoglycans (and hence Gram-positive bacteria) (Lu et al., Biochim Biophys Acta 2002; 1572:387-400), is utilized. Collectins assemble into multimers, effectively multiplying the number of binding sites per complex available for interaction with the microorganism's repetitive surface.

In other embodiments the Toll receptor family are used as pathogen targeting molecules; this group of cell bound receptors functions singly or in concert with other innate immune system receptors (Ezekowitz and Hoffmann, Innate Immunity. Totowa, N.J.: HUmana Press, 2003; Janeway and Medzhitov. Annu Rev Immunol 2002; 20:197-216; Medzhitov and Janeway, Trends Microbiol 2000; 8:452-6. Toll like receptors (TLRs) comprise a family of cell surface receptors that are related to the *Drosophila* Toll protein, a molecule involved in defense against fungal infection in the fly (Aderem and Ulevitch, Nature, 406:785-787 [2000]). Ten mammalian TLRs have been identified (Aderem and Ulevitch, Supra). Two members of the family, TLR2 and TLR4, have been better characterized and shown to mediate the response to multiple bacterial cell-wall components including lipopolysaccharide (LPS), lipopeptides, peptidoglycans (PGN) and lipoteichoic acid (LTA) (Yang et al., Nature, 395: 284-288 [1998]; Poltorak et al., Science, 282:2085-2088 [1998]; Aliprantis et al., Science, 285:736-739 [1999]; Chow et al., J. Biol. Chem., 274:10689-10692 [2000]; and Schwandner et al., J. Biol. Chem., 274: 17406-17409 [2000]). Mammalian TLRs have multiple leucine-rich repeats in the ectodomain and an intracellular Toll-IL1 receptor (TIR) domain that mediates a signaling cascade to the nucleus (Aderem and Ulevitch, Supra). Stimulation of TLR2 and TLR4 leads to the recruitment of the adaptor molecule MyD88 and the serine kinase IL-1R-associated kinase (IRAK), two signaling components that together with TRAF-6 mediate activation of NF-κB (Aderem and Ulevitch, Supra).

III. Linkers

In preferred embodiments, the transgenic fusion proteins comprise a targeting molecule (e.g., immunoglobulin heavy chain (or fragment thereof) and a light chain or (a fragment thereof)) connected to a biocide molecule by a linker. In preferred embodiments, the targeting molecule is linked via a peptide linker or is directly fused (e.g., covalently bonded) to the biocide molecule. In preferred embodiments, the transgenic fusion proteins assemble into dimeric, trimeric, tetrameric, pentameric, hexameric or higher polymeric complexes.

In preferred embodiments, the present invention provides retroviral constructs that encode in operable configuration an immunoglobulin (or portion thereof), a biocide molecule (or portion thereof), and a linker group that connects the immunoglobulin and the biocide. In some of these embodiments, the linker group comprises one amino acid moiety (e.g., $X_n$; wherein X is any amino acid or amino acid derivative; and n=1). In some of these embodiments, the linker group comprises at least one amino acid moiety (e.g., $X_n$; wherein X is any amino acid or amino acid derivative; and n≧2). Similarly, in other embodiments, the linker group comprises two or more repeating amino acids (e.g., $X_n Y_z$; wherein X and Y are any amino acid or amino acid derivative; and n≧1 and z≧1). In still further embodiments, the linker group comprises two or more repeating amino acids that form a repeating unit (e.g., $(X_n Y_z)_r$; wherein r≧1). The present invention is not intended to be limited, however, to the aforementioned linker groups. Those skilled in the art will appreciate that a number of other linker group configurations and compositions find use in certain embodiments of the present invention.

In particularly preferred embodiments, the linker group used has one or more of the following characteristics: 1) sufficient length and flexibility to allow for the rotation of the targeting molecule (e.g., immunoglobulin) and the biocide molecule (e.g., lysozyme) relative to one another; 2) a flexible extended conformation; 3) a propensity for developing ordered secondary or tertiary structures that interact with functional components; 4) nonreactive with the functional components of the construct (e.g., minimal hydrophobic or charged character to react with the functional protein domains); 5) sufficient resistant to degradation (e.g., digestion by proteases); and 6) allows the fusion protein to form a complex (e.g., a di-, tri-, tetra-, penta-, or higher multimeric complex) while retaining biological (e.g., biocidal) activity. The linker sequence should separate the target molecule and the biocide molecule of the fusion protein by a distance sufficient to ensure that each component properly folds into its secondary and tertiary structures.

In preferred embodiments, the peptide linker is from about 2 to 500, more preferably of from about 50 to 100, and even more preferably, from about 10 to 30 amino acids long. A polypeptide linker sequence of about 20 amino acids provides a suitable separation of functional protein domains, although longer or shorter linker sequences are contemplated. For example, in particularly preferred embodiments, the peptide linker is between 17 to 20 amino acids in length.

The present invention further contemplates peptide linkers comprised of the following amino acids: Gly, Ser, Asn, Thr or Ala. Typical surface amino acids in flexible protein regions include Gly, Ser, and Asn. The present invention contemplates that various amino acid sequence permutations of Gly, Ser, and optionally Asn, provide suitable linker sequences. However, the present invention is not limited to peptide linkers comprised of the aforementioned amino acids. For example, in some embodiments, the peptide linkers comprise further uncharged polar amino acids (e.g., Gin, or Tyr) and/or nonpolar amino acids (e.g., Val, Leu, Ileu, Pro, Phe, Met, Trp, Cys).

In some preferred embodiments, the peptide linker comprises one (or more) Gly-Ser elements. Fore example, in some of these embodiments, the peptide linker has the formula $(Ser_n\text{-}Gly_x)_y$, wherein n and x≧1, and y≧1. In some preferred embodiments, the peptide linker has the formula $(Ser\text{-}Gly_4)_y$, wherein y=1, 2, 3, 4, 5, 6, 7, 8 or more. In some other preferred embodiments, the peptide linker includes a sequence having the formula $(Ser\text{-}Gly_4)_3$. In still other preferred embodiments, the peptide linker comprises a sequence of the formula $((Ser\text{-}Gly_4)_3\text{-}Ser\text{-}Pro)$. Other peptide linker sequences are contemplated, including, but not limited to, $Gly_4SerGly_5Ser$, and $((Ser_4\text{-}Gly)_3\text{-}Ser\text{-}Pro)$.

In still further embodiments, the target molecule and the biocidal molecule comprising the fusion protein are fused directly without a linker sequence. In some embodiments, linker sequences are unnecessary where the fusion protein components have non-essential N-or C-terminal amino acid regions that separate functional domains and prevent steric interference.

IV. Biocides

The present invention provides novel fusion proteins. In preferred embodiments, the recombinant fusion proteins comprise one or more biocide molecules (e.g., a bactericidal enzyme) attached to the antibody portion of the construct via a linking group. The specificity of the monoclonal antibody portion of the construct targets the biocide molecule to a pathogen such as, for example, *E. coli* O157:H7, *Listeria monocytogenes, Campylobacter jejuni*, or *Cryptosporidium parvum*.

One benefit of the specific targeting ability of the fusion protein construct is that it allows for relative accumulation of biocide at locations where the targeted pathogens are challenging the animal. Increasing the local concentration of biocide relative to the targeted pathogens enhances the biocidal activity of the fusion protein construct. In particular, the present invention contemplates that directing the biocide (e.g., lysozyme, PLA2, and the like) to the immediate vicinity of the pathogen (e.g., a bacterium) via the antibody portion of the construct effectively increasing the biocide's local concentration, thus providing a significantly greater biocidal (e.g., bactericidal) effect than administering biocide alone (parasiticidal compounds). For example in the case of lysozyme, the affinity constant ($K_m$) of lysozyme for its substrate is approximately $10^{-3}$ M, while that of phospholipase A2 is approximately $10^{-4}$ M. However, the $K_d$ of a monoclonal antibody is usually in the range of $10^{-8}$ M to $10^{-11}$ M, thus antibodies have about 5 orders of magnitude higher affinity for their substrates than do biocidal molecules alone. Therefore, preferred embodiments of the present invention utilize monoclonal antibodies (or portions thereof) to specifically direct biocide molecules to a target by taking advantage of the antibody's very high affinity for target pathogens. Additionally, directing the fusion protein constructs to target pathogens also reduces the possible deleterious effects to the animal caused by systemic administration of the biocidal molecules.

In preferred embodiments, the directed biocidal approach described herein uses a monoclonal antibody to direct a naturally occurring bactericidal enzyme to the target pathogen. In some of these embodiments, the bactericidal enzyme(s) are components of the innate immune system. One such preferred bactericidal enzyme is lysozyme.

Lysozyme is naturally present in mammalian tissues and in secretions such as tears and mucus. Lysozyme is also found in many foods including, egg whites, cow milk, and human colostrum. The enzyme is widely reported to have antibacterial properties. Lysozyme is a glycosidase that targets the polysaccharides of many bacterial cell walls rendering them more susceptible to osmotic lysis. Lysozyme is a 1,4-β-N-acetylmurmidase that cleaves the glycosidic bond between C-1 of N-acetylmuramic acid and C-4 of N-acetylglucosamine of the peptidoglycan layer present in many bacterial cell walls (See e.g., M. Schindler et al., Biochemistry, 16(3):423-431 [1977]). While it is not clear whether this cleavage contributes to the bactericidal action of lysozyme (K. During et al., FEBS Lett., 449(2-3):93-100 [1999]; and H. R. Ibrahim et al., FEBS Lett., 506(1):27-32 [2001]), it is widely accepted that lysozyme plays an important role in defense against bacterial infection. Lysozyme has also been shown to bind to the lipid A portion of bacterial endotoxin. This interaction prevents the endotoxin from inducing the release of inflammatory components by lymphocytes and macrophages (See e.g., B. Reusens-Billen et al., Diabetes Res. Clin. Pract., 23(2):85-94 [1994]; K. Takada et al., Infect. Immun., 62(4):1171-1175 [1994]; and K. Takada et al., Circ. Shock, 44(4):169-174 [1994]).

Other proteins that form part of the innate immune system, and especially those secreted by the intestinal Paneth cells, are contemplated for targeting the structural integrity of sporozoites. For example, phopholipase A2 (PLA2) is another naturally occurring bactericidal enzyme contemplated for use in certain embodiments of the present invention. Secretory type II phospholipase A2 (sPLA(2)-IIA) is a 14 kD enzyme synthesized in a number of gland cells, including Paneth cells of intestinal mucosa, prostate gland cells, and lacrimal glands. It is present in cellular secretions on mucosal surfaces including intestinal mucus, seminal plasma, and tears (X. D. Qu and R. I. Lehrer, Infect. Immun., 66:2791-2797 [1998]; and X. D. Qu et al., Infect. Immun., 64:5161-5165 [1996]). Evidence suggests that phopholipase A2 has an important antibacterial role in addition to its inflammatory mediating role (See e.g., A. G. Buckland and D. C. Wilton, Biochim. Biophys. Acta, 1488(1-2):71-82 [2000]). Elevated amounts of phospholipase A2 is found in patients with acute bacterial diseases (J. O. Gronoos et al., J. Infect. Dis., 185: 1767-1772 [2002]). The enzyme appears to effective in controlling *E coli.* infections when expressed in transgenic mice (See e.g., V. J. Laine et al., Infect. Immun., 68(1):87-92 [2000]). While the present invention is not limited to any mechanisms, PLA2 appears to hydrolyze membrane phospholipids, thus destroying the membranes of invading microbes. PLA2 serves as a critical component of the innate immune system, functioning in combination with lysozyme and the defensins to provide an effective barrier to invasion by a diverse range of organisms.

Mammalian cells are generally highly resistant to sPLA(2) IIA (R. S. Koduri et al., J. Biol. Chem., 273:32142-32153 [1998]). The substrate specificity of the different members of the PLA2 family may be related to the differences in interfacial binding characteristics to charge-neutral phosphotidyl choline (PC) versus anionic phospholipids. Indeed, sPLA(2) family members sPLA2-V and -X bind efficiently and hydrolyze PC vesicles in vitro whereas the vesicles are a poor binding substrate for-IIA. Plasma membranes with a high PC content would therefore be stable in the presence of sPLA(2)-IIA. The composition of the phospholipids on the surface of the organism therefore contributes to the susceptibility of the organism to the action of sPLA2. Some parasitic eukaryotic organisms may evade the innate immune system by not stimulating the cells of the immune system to release biocidal enzymes and defensins (e.g., *G. lamblia* and *C. albicans* appear not to stimulate Paneth cells). However, one recent report suggests that *Plasmodium* is susceptible to sPLA2 (Type III, from bee venom). Type III sPLA2 has an activity that is similar to the type IIA enzyme, but is a slightly larger molecule having N- and C-terminal extensions. Systemically, sPLA(2)-IIA has a role in generalized inflammatory responses. In acute inflammation, the levels of the enzyme are elevated many hundreds of fold, however, it appears to have no adverse effect at epithelial surfaces. In vitro, sPLA(2) apparently has no deleterious effect on various types of cultured mammalian cells. Healthy transgenic mice chronically over-expressing sPLA(2)-IIA have been produced and exhibit an elevated resistance to infection by gram positive organisms (V. J. Laine et al., J. Immunol., 162:7402-7408 [1999]; and V. J. Laine et al., Infect, Immun., 68:87-92 [2000]).

A number of inhibitors have been identified that have activity against *C. parvum* by targeting the parasite's metabolic pathways. These include, but are not limited to, metalloprotease inhibitors (P. C. Okhuysen et al., Antimicrob. Agents Chemother., 40:2781-2784 [1996]) and serine protease antagonists (J. R. Forney et al., J. Parasitol., 82:638-640 [1996]). Other enzymes essential to *C. parvum* infectivity provide useful inhibitor targets. These include, for example, phosphoinositide 3-kinase (J. R. Forney et al., Infect. Immun., 67:844-852 [1999]) and cysteine proteinase (M. V. Nesterenko et al., Microbios., 83:77-88 [1995]).

Other naturally occurring bactericidal molecules (e.g., enzymes) contemplated for use in certain embodiments of the present invention, include, but are not limited to, lactoferrin, lactoperoxidase, bacterial permeability increasing protein (BPI), and Aprotinin. (See e.g., B. A. Mannion et al., J. Clin. Invest., 85(3):853-860 [1990]; A. Pellegrini et al., Biochem. Biophys. Res. Commun., 222(2):559-565 [1996]; and P. Prohinar et al., Mol. Microbiol., 43(6):1493-1504 [2002]).

In some embodiments of the present invention, the biocide component of the fusion protein comprises an antimicrobial polypeptide (See e.g., *Antimicrobial Peptide Protocols*, ed. W. M. Shafer, Humana Press, Totowa, N.J. [1997]) or a pore forming agent. In some embodiments, the antimicrobial peptide or pore forming agent is a compound or peptide selected from the following: magainin (e.g., magainin I, magainin II, xenopsin, xenopsin precursor fragment, caerulein precursor fragment), magainin I and II analogs (PGLa, magainin A, magainin G, pexiganin, Z-12, pexigainin acetate, D35, MSI-78A, MG0 [K10E, K11E, F12W-magainin 2], MG2+[K10E, F12W-magainin-2], MG4+[F12W-magainin 2], MG6+ [f12W, E19Q-magainin 2 amide], MSI-238, reversed magainin II analogs [e.g., 53D, 87-ISM, and A87-ISM], Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME (1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 [(+/−)1-(4-aminobutyl)-6-benzylindane], PM2c [(+/−)-6-benzyl-1-(3-carboxypropyl)indane], PM3 [(+/−)1-benzyl-6-(4-aminobutyl)indane], tachyplesin, buforin I or II, misgurin, melittin, PR-39, PR-26, 9-phenylnonylamine, (KLAKKLA)n, (KLAKLAK)n, where n=1, 2, or 3, (KALKALK)3, KLGKKLG)n, and KAAKKAA)n, wherein N=1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG 1, 1 bAMP, snakin, lipid transfer proteins, and plant defensins. Exemplary sequences for the above compounds are provided in Table 1. In some embodiments, the antimicrobial peptides are synthesized from L-amino acids, while in other embodiments, the peptides are synthesized from or comprise D-amino acids.

TABLE 1

Antimicrobial Peptides

| SEQ ID NO: | Name | Organism | Sequence |
|---|---|---|---|
| 1 | lingual antimicrobial peptide precursor (Magainin) | Bos taurus | MRLHHLLLALLFLVLSAGSGFTQGVR NSQSCRRNKGICVP IRCPGSMRQIGTCLGAQVKCCRRK |
| 2 | antimicrobial peptide PGQ | Xenopus laevis | GVLSNVIGYLKKLGTGALNAVLKQ |
| 3 | Xenopsin | Xenopus laevis | MYKGIFLCVLLAVICANSLATPSSDA DEDNDEVERYVRGW ASKIGQTLGKIAKVGLKELIQPKREA MLRSAEAQGKIRPWIL |

TABLE 1-continued

Antimicrobial Peptides

| SEQ ID NO: | Name | Organism | Sequence |
|---|---|---|---|
| 4 | magainin precursor | Xenopus laevis | MFKGLFICSLIAVICANALPQPEASAD EDMDEREVRGIGKFLHSAGKFGKAF VGEIMKSKRDAEAVGPEAFADEDLD EREVRGIGKFLHSAKKFGKAFVGEIM NSKRDAEAVGPEAFADEDLDEREVR GIGKFLHSAKKFGKAFVGEIMNSKRD AEAVGPEAFADEDLDEREVRGIGKFL HSAKKFGKAFVGEIMNSKRDAEAVG PEAFADEDFDEREVRGIGKFLHSAKK FGKAFVGEIMNSKRDAEAVGPEAFA DEDLDEREVRGIGKFLHSAKKFGK AFVGEIMNSKRDAEAVDDRRWVE |
| 5 | tachyplesin I | Tachypleus gigas | KWCFRVCYRGICYRRCR |
| 6 | tachyplesin II | Tachypleus gigas | RWCFRVCYRGICYRKCR |
| 7 | buforin I | Bufo bufo gagarizans | MSGRGKQGGKVRAKAKTRSSRAGL QFPVGRVHRLLRKGNYAQRVGAGA PVYLAAVLEYLTAEILELAGNAARD NKKTRIIPRHLQLAVRNDEELNKLLG GVTIAQGGVLPNIQAVLLPKT ESSKPAKSK |
| 8 | buforin II | Bufo bufo gagarizans | TRSSRAGLQFPVGRVHRLLRK |
| 9 | cecropin A | Bombyx mori | MNFVRILSFVFALVLALGAVSAAPEP RWKLFKKIEKVGRNVRDGLIKAGPAI AVIGQAKSLGK |
| 10 | cecropin B | Bombyx mori | MNFAKILSFVFALVLALSMTSAAPEP RWKIFKKIEKMGRN IRDGIVKAGPAIEVLGSAKAIGK |
| 11 | cecropin C | Drosophila melanogaster | MNFYKIFVFVALILAISIGQSEAGWLK KLGKRIERIGQHT RDATIQGLGIAQQAANVAATARG |
| 12 | cecropin P1 | Sus scrofa | SWLSKTAKKLENSAKKRISEGIAIAIQ GGPR |
| 13 | indolicidin | Bos taurus | ILPWKWPWWPWRR |
| 14 | nisin | Lactococcus lactis | ITSISLCTPGCKTGALMGCNMKTATC HCSIHVSK |
| 15 | ranalexin | Rana catesbeiana | FLGGLIKIVPAMICAVTKKC |
| 16 | lactoferricin B | Bos taurus | FKCRRWQWRMKKLGAPSITCVRRAF |
| 17 | protegrin-1 | Sus scrofa | RGGRLCYCRRRFCVCVGRX |
| 18 | protegrin-2 | Sus scrofa | GGRLCYCRRRFCICVG |
| 19 | histatin precursor | Homo sapiens | MKFFVFALILALMLSMTGADSHAKR HHGYKRKFHEKHHSHRGYRSNYLY DN |
| 20 | histatin 1 | Macaca fascicularis | DSHEERHHGRHGHHKYGRKFHEKH HSHRGYRSNYLYDN |
| 21 | dermaseptin | Phyllomedusa sauvagei | ALWKTMLKKLGTMALHAGKAALGA AADTISQTQ |
| 22 | dermaseptin 2 | Phyllomedusa sauvagei | ALWFTMLKKLGTMALHAGKAALGA AANTISQTQ |

TABLE 1-continued

Antimicrobial Peptides

| SEQ ID NO: | Name | Organism | Sequence |
|---|---|---|---|
| 23 | dermaseptin 3 | Phyllomedusa sauvagei | ALWKNMLKGIGKLAGKAALGAVKKLVGAES |
| 24 | misgurin | Misgurnus anguillicaudatus | RQRVEELSKFSKKGAAARRRK |
| 25 | melittin | Apis mellifera | GIGAVLKVLTTGLPALISWISRKKRQQ |
| 26 | pardaxin-1 | Pardachirus pavoninus | GFFALIPKIISSPLFKTLLSAVGSALSSSGEQE |
| 27 | pardaxin-2 | Pardachirus pavoninus | GFFALIPKIISSPIFKTLLSAVGSALSSSGGQE |
| 28 | bactenecin 5 precursor | Bos taurus | METQRASLSLGRCSLWLLLLGLVLPSASAQALSYREAVLRAVDQFNERSSEANLYRLLELDPTPNDDLDPGTRKPVSFRVKETDCPRTSQQPLEQCDFKENGLVKQCVGTVTLDPSNDQFDINCNELQSVRFRPPIRRPPIRPPFYPPFRPPIRPPIFPPIRPPFRPPLGPFPGRR |
| 29 | bactenecin precursor | Bos taurus | METPRASLSLGRWSLWLLLLGLALPSASAQALSYREAVLRAVDQLNEQSSEPNIYRLLELDQPPQDDEDPDSPKRVSFRVKETVCSRTTQQPPEQCDFKENGLLKRCEGTVTLDQVRGNFDITCNNHQSIRITKQPWAPPQAARLCRIVVIRVCR |
| 30 | ceratotoxin A | Ceratitis capitata | SIGSALKKALPVAKKIGKIALPIAKAALP |
| 31 | ceratotoxin B | Ceratitis capitata | SIGSAFKKALPVAKKIGKAALPIAKAALP |
| 32 | cathelicidin antimicrobial peptide | Homo sapiens | MKTQRNGHSLGRWSLVLLLLGLVMPLAIIAQVLSYKEAVLRAIDGINQRSSDANLYRLLDLDPRPTMDGDPDTPKPVSFTVKETVCPRTTQQSPEDCDFKKDGLVKRCMGTVTLNQARGSFDISCDKDNKRFALLGDFFRKSKEKIGKEFKRIVQRIKDFLRNLVPRTES |
| 33 | myeloid cathelicidin 3 | Equus caballus | METQRNTRCLGRWSPLLLLLGLVIPPATTQALSYKEAVLRAVDGLNQRSSDENLYRLLELDPLPKGDKDSDTPKPVSFMVKETVCPRIMKQTPEQCDFKENGLVKQCVGTVILDPVKDYFDASCDEPQRVKRFHSVGSLIQRHQQMIRDKSEATRHGIRIITRPKLLLAS |
| 34 | myeloid antimicrobial peptide BMAP-28 | Bos taurus | METQRASLSLGRWSLWLLLLGLALPSASAQALSYREAVLRAVDQLNEKSSEANLYRLLELDPPPKEDDENPNIPKPVSFRVKETVCPRTSQQSPEQCDFKENGLLKECVGTVTLDQVGSNFDITCAVPQSVGGLRSLGRKILRAWKKYGPIIVPIIRIG |
| 35 | myeloid cathelicidin 1 | Equus caballus | METQRNTRCLGRWSPLLLLLGLVIPPATTQALSYKEAVLRAVDGLNQRSSDENLYRLLELDPLPKGDKDSDTPKPVSFMVKETVCPRIMKQTPEQCDFKENGLVKQCVGTVILGPVKDHFDVSCGEPQRVKRFGRLAKSFLRMRILLPRRKILLAS |

TABLE 1-continued

Antimicrobial Peptides

| SEQ ID NO: | Name | Organism | Sequence |
|---|---|---|---|
| 36 | SMAP 29 | Ovis aries | METQRASLSLGRCSLWLLLLGLALPS ASAQVLSYREAVLRAADQLNEKSSE ANLYRLLELDPPPKQDDENSNIPKPV SFRVKETVCPRTSQQPAEQCDFKENG LLKECVGTVTLDQVRNNFDITCAEPQ SVRGLRRLGRKIAHGVKKYGPTVLRI IRIAG |
| 37 | BNP-1 | Bos taurus | RLCRIVVIRVCR |
| 38 | HNP-1 | Homo sapiens | ACYCRIPACIAGERRYGTCIYQGRLW AFCC |
| 39 | HNP-2 | Homo sapiens | CYCRIPACIAGERRYGTCIYQGRLWA FCC |
| 40 | HNP-3 | Homo sapiens | DCYCRIPACIAGERRYGTCIYQGRLW AFCC |
| 41 | HNP-4 | Homo sapiens | VCSCRLVFCRRTELRVGNCLIGGVSF TYCCTRV |
| 42 | NP-1 | Oryctolagus cuniculus | VVCACRRALCLPRERRAGFCRIRGRI HPLCCRR |
| 43 | NP-2 | Oryctolagus cuniculus | VVCACRRALCLPLERRAGFCRIRGRI HPLCCRR |
| 44 | NP-3A | Oryctolagus cuniculus | GICACRRRFCPNSERFSGYCRVNGAR YVRCCSRR |
| 45 | NP-3B | Oryctolagus cuniculus | GRCVCRKQLLCSYRERRIGDCKIRGV RFPFCCPR |
| 46 | NP-4 | Oryctolagus cuniculus | VSCTCRRFSCGFGERASGSCTVNGG VRHTLCCRR |
| 47 | NP-5 | Oryctolagus cuniculus | VFCTCRGFLCGSGERASGSCTINGVR HTLCCRR |
| 48 | RatNP-1 | Rattus norvegicus | VTCYCRRTRCGFRERLSGACGYRGRI YRLCCR |
| 49 | Rat-NP-3 | Rattus norvegicus | CSCRYSSCRFGERLLSGACRLNGRIY RLCC |
| 50 | Rat-NP-4 | Rattus norvegicus | ACTCRIGACVSGERLTGACGLNGRIY RLCCR |
| 51 | GPNP | Guinea pig | RRCICTTRTCRFPYRRLGTCIFQNRVY TFCC |
| 52 | beta defensin-3 | Homo sapiens | MRIHYLLFALLFLFLVPVPGHGGIINT LQKYYCRVRGGRC AVLSCLPKEEQIGKCSTRGRKCCRRK K |
| 53 | theta defensin-1 | Macaca mulatta | RCICTRGFCRCLCRRGVC |
| 54 | defensin CUA1 | Helianthus annuus | MKSSMKMFAALLLVVMCLLANEMG GPLVVEARTCESQSHKFKGTCLSDTN CANVCHSERFSGGKCRGFRRRCFCT THC |
| 55 | defensin SD2 | Helianthus annuus | MKSSMKMFAALLLVVMCLLANEMG GPLVVEARTCESQSHKLFKGTCLSDTN CANVCHSERFSGGKCRGFRRRCFCT THC |
| 56 | neutrophil defensin 2 | Macaca mulatta | ACYCRIPACLAGERRYGTCFYMGRV WAFCC |

TABLE 1-continued

Antimicrobial Peptides

| SEQ ID NO: | Name | Organism | Sequence |
|---|---|---|---|
| 57 | 4 KDA defensin | Androctonus australis hector | GFGCPFNQGACHRHCRSIRRRGGYC AGLFKQTCTCYR |
| 58 | defensin | Mytilus galloprovincialis | GFGCPNNYQCHRHCKSIPGRCGGYC GGXHRLRCTCYRC |
| 59 | defensin AMP1 | Heuchera sanguinea | DGVKLCDVPSGTWSGHCGSSSKCSQ QCKDREHFAYGGACH YQFPSVKCFCKRQC |
| 60 | defensin AMP1 | Clitoria ternatea | NLCERASLTWTGNCGNTGHCDTQCR NWESAKHGACHKRGN WKCFCYFNC |
| 61 | cysteine-rich cryptdin-1 homolog | Mus musculus | MKKLVLLFALVLLAFQVQADSIQNT DEETKTEEQPGEKDQAVSVSFGDPQ GSALQDAALGWRRCPQCPRCPSCP SCPRC PRCPRCKCNPK |
| 62 | beta-defensin-9 | Bos taurus | QGVRNFVTCRINRGFCVPIRCPGHRR QIGTCLGPQIKCCR |
| 63 | beta-defensin-7 | Bos taurus | QGVRNFVTCRINRGFCVPIRCPGHRR QIGTCLGPRIKCCR |
| 64 | beta-defensin-6 | Bos taurus | QGVRNHVTCRIYGGFCVPIRCPGRTR QIGTCFGRPVKCCRRW |
| 65 | beta-defensin-5 | Bos taurus | QVVRNPQSCRWNMGVCIPISCPGNM RQIGTCFGPRVPCCR |
| 66 | beta-defensin-4 | Bos taurus | QRVRNPQSCRWNMGVCIPFLCRVG MRQIGTCFGPRVPCCRR |
| 67 | beta-defensin-3 | Bos taurus | QGVRNHVTCRINRGFCVPIRCPGRTR QIGTCFGPRIKCCRSW |
| 68 | beta-defensin-10 | Bos taurus | QGVRSYLSCWGNRGICLLNRCPGRM RQIGTCLAPRVKCCR |
| 69 | beta-defensin-13 | Bos taurus | SGISGPLSCGRNGGVCIPIRCPVPMRQ IGTCFGRPVKCCRSW |
| 70 | beta-defensin-1 | Bos taurus | DFASCHTNGGICLPNRCPGHMIQIGIC FRPRVKCCRSW |
| 71 | coleoptericin | Zophobas atratus | SLQGGAPNFPQPSQQNGGWQVSPDL GRDDKGNTRGQIEIQNKGKDHDFNA GWGKVIRGPNKAKPTWHVGGTYRR |
| 72 | beta defensin-3 | Homo sapiens | MRIHYLLFALLFLFLVPVPGHGGIINT LQKYYCRVRGGRCAVLSCLPKEEQI GKCSTRGRKCCRRKK |
| 73 | defensin C | Aedes aegypti | ATCDLLSGFGVGDSACAAHCIARGN RGGYCNSKKVCVCRN |
| 74 | defensin B | Mytilus edulis | GFGCPNDYPCHRHCKSIPGRYGGYC GGXHRLRCTC |
| 75 | sapecin C | Sarcophaga peregrina | ATCDLLSGIGVQHSACALHCVFRGN RGGYCTGKGICVCRN |
| 76 | macrophage antibiotic peptide MCP-1 | Oryctolagus cuniculus | MRTLALLAAILLVALQAQAEHVSVSI DEVVDQQPPQAEDQDVAIYVKEHES SALEALGVKAGVVCACRRALCLPRE RRAG FCRIRGRIHPLCCRR |

TABLE 1-continued

Antimicrobial Peptides

| SEQ ID NO: | Name | Organism | Sequence |
|---|---|---|---|
| 77 | cryptdin-2 | Mus musculus | MKPLVLLSALVLLSFQVQADPIQNTD EETKTEEQSGEEDQAVSVSFGDREG ASLQEESLRDLVCYCRTRGCKRRER MNGT CRKGHLMYTLCC |
| 78 | cryptdin-5 | Mus musculus | MKTFVLLSALVLLAFQVQADPIHKTD EETNTEEQPGEEDQ AVSISFGGQEGSALHEELSKKLICYCR IRGCKRRERVFGT CRNLFLTFVFCCS |
| 79 | cryptdin 12 | Mus musculus | LRDLVCYCRARGCKGRERMNGTCR KGHLLYMLCCR |
| 80 | defensin | Pyrrhocoris apterus | ATCDILSFQSQWVTPNHAGCALHCVI KGYKGGQCKITVCHCRR |
| 81 | defensin R-5 | Rattus norvegicus | VTCYCRSTRCGFRERLSGACGYRGRI YRLCCR |
| 82 | defensin R-2 | Rattus norvegicus | VTCSCRTSSCRFGERLSGACRLNGRI YRLCC |
| 83 | defensin NP-6 | Oryctolagus cuniculus | GICACRRRFCLNFEQFSGYCRVNGAR YVRCCSRR |
| 84 | beta-defensin-2 | Pan troglodytes | MRVLYLLFSFLFIFLMPLPGVFGGISD PVTCLKSGAICHP VFCPRRYKQIGTCGLPGTKCCKKP |
| 85 | beta-defensin-2 | Homo sapiens | MRVLYLLFSFLFIFLMPLPGVFGGIGD PVTCLKSGAICHP VFCPRRYKQIGTCGLPGTKCCKKP |
| 86 | beta-defensin-1 | Homo sapiens | MRTSYLLLFTLCLLLSEMASGGNFLT GLGHRSDHYNCVSS GGQCLYSACPIFTKIQGTCYRGKAKC CK |
| 87 | beta-defensin-1 | Capra hircus | MRLHHLLLVLFFLVLSAGSGFTQGIR SRRSCHRNKGVCAL TRCPRNMRQIGTCFGPPVKCCRKK |
| 88 | beta defensin-2 | Capra hircus | MRLHHLLLALFFLVLSAGSGFTQGIIN HRSCYRNKGVCAP ARCPRNMRQIGTCHGPPVKCCRKK |
| 89 | defensin-3 | Macaca mulatta | MRTLVILAAILLVALQAQAEPLQART DEATAAQEQIPTDNPEVVVSLAWDE SLAPKDSVPGLRKNMACYCRIPACL AGER RYGTCFYRRRVWAFCC |
| 90 | defensin-1 | Macaca mulatta | MRTLVILAAILLVALQAQAEPLQART DEATAAQEQIPTDNPEVVVSLAWDE SLAPKDSVPGLRKNMACYCRIPACL AGER RYGTCFYLGRVWAFCC |
| 91 | neutrophil defensin 1 | Mesocricetus auratus | VTCFCRRRGCASRERHIGYCRFGNTI YRLCCRR |
| 92 | neutrophil defensin 1 | Mesocricetus auratus | CFCKRPVCDSGETQIGYCRLGNTFYR LCCRQ |
| 93 | Gallinacin 1-alpha | Gallus gallus | GRKSDCFRKNGFCAFLKCPYLTLISG KCSRFHLCCKRIW |
| 94 | defensin | Allomyrina dichotoma | VTCDLLSFEAKGFAANHSLCAAHCL AIGRRGGSCERGVCICRR |
| 95 | neutrophil cationic peptide 1 | Cavia porcellus | RRCICTTRTCRFPYRRLGTCIFQNRVY TFCC |

In some embodiments of the present invention, the antimicrobial polypeptide is a defensin. In preferred embodiments, the compositions of the present invention comprise one or more defensins. In some of these embodiments, the antimicrobial polypeptide defensin is BNP1 (also known as bactanecin and bovine dodecapeptide). IN certain embodiments, the defensin comprises the following consensus sequence: (SEQ. ID NO:96-$X_1CN_1CRN_2CN_3ERN_4CN_5GN_6CCX_2$, wherein N and X represent conservatively or nonconservatively substituted amino acids and $N_1=1$, $N_2=3$ or 4, $N_3=3$ or 4, $N_4=1$, 2, or 3, $N_6=5$-9, $X_1$ and $X_2$ may be present, absent, or equal from 1-2. The present invention is not limited to any particular defensin. Representative defensins are provided in Tables 1 and 2.

TABLE 2

Defensins

| SEQ ID NO | Name | Organism | Sequence |
|---|---|---|---|
| 38 | HNP-1 | Human | ACYCRIPACIAGERRYGTCIYQGRLWAFCC |
| 39 | HNP-2 | Human | CYCRIPACIAGERRYGTCIYQGRLWAFCC |
| 40 | HNP-3 | Human | DCYCRIPACIAGERRYGTCIYQGRLWAFCC |
| 41 | HNP-4 | Human | VCSCRLVFCRRTELRVGNCLIGGVSFTYCCTRV |
| 42 | NP-1 | Rabbit | VVCACRRALCLPRERRAGFCRIRGRIHPLCCRR |
| 43 | NP-2 | Rabbit | VVCACRRALCLPLERRAGFCRIRGRIHPLCCRR |
| 44 | NP-3A | Rabbit | GICACRRRFCPNSERFSGYCRVNGARYVRCCSRR |
| 45 | NP-3B | Rabbit | GRCVCRKQLLCSYRERRIGDCKIRGVRFPFCCPR |
| 46 | NP-4 | Rabbit | VSCTCRRFSCGFGERASGSCTVNGVRHTLCCRR |
| 47 | NP-5 | Rabbit | VFCTCRGFLCGSGERASGSCTINGVRHTLCCRR |
| 48 | RatNP-1 | Rat | VTCYCRRTRCGFRERLSGACGYRGRIYRLCCR |
| 49 | Rat-NP-3 | Rat | CSCRYSSCRFGERLLSGACRLNGRIYRLCC |
| 50 | Rat-NP-4 | Rat | ACTCRIGACVSGERLTGACGLNGRIYRLCCR |
| 51 | GPNP | Guinea pig | RRCICTTRTCRFPYRRLGTCIFQNRVYTFCC |

In general, defensins are a family of highly cross-linked, structurally homologous antimicrobial peptides found in the azurophil granules of polymorphonuclear leukocytes (PMN's) with homologous peptides being present in macrophages. (See e.g., Selsted et al., Infect. Immun., 45:150-154 [1984]). Originally described as "Lysosomal Cationic Peptides" in rabbit and guinea pig PMN (Zeya et al., Science, 154:1049-1051 [1966]; Zeya et al., J. Exp. Med., 127:927-941 [1968]; Zeya et al., Lab. Invest., 24:229-236 [1971]; Selsted et al., [1984], supra.), this mixture was found to account for most of the microbicidal activity of the crude rabbit PMN extract against various microorganisms (Zeya et al., [1966], supra; Lehrer et al., J. Infect. Dis., 136:96-99 [1977]; Lehrer et al., Infect. Immun., 11:1226-1234 [1975]). Six rabbit neutrophil defensins have been individually purified and are designated NP-1, NP-2, NP-3A, NP-3B, NP-4, and NP-5. Their amino acid sequences were determined, and their broad spectra of activity were demonstrated against a number of bacteria (Selsted et al., Infect. Immun., 45:150-154 [1984]), viruses (Lehrer et al., J. Virol. 54:467 [1985]), and fungi (Selsted et al., Infect. Immun., 49:202-206 [1985]; Segal et al., 151:890-894 [1985]). Defensins have also been shown to possess mitogenic activity (e.g., Murphy et al., J. Cell. Physiol., 155:408-13 [1993]).

Four peptides of the defensin family have been isolated from human PMN's and are designated HNP-1, HNP-2, HNP-3, and HNP-4 (Ganz et al., J. Clin. Invest., 76:1427-1435 [1985]; Wilde et al., J. Biol. Chem., 264:11200-11203 [1989]). The amino acid sequences of HNP-1, HNP-2, and HNP-3 differ from each other only in their amino terminal residues, while each of the human defensins are identical to the six rabbit peptides in 10 or 11 of their 29 to 30 residues. These are the same 10 or 11 residues that are shared by all six rabbit peptides. Human defensin peptides have been shown to share with the rabbit defensins a broad spectrum of antimicrobial activity against bacteria, fungi, and enveloped viruses (Ganz et al., [1985], supra).

Three defensins designated RatNP-1, RatNP-2, and RatNP-4, have been isolated from rat. (Eisenhauer et al., Infection and Immunity, 57:2021-2027 [1989]). A guinea pig defensin (GPNP) has also been isolated, purified, sequenced and its broad spectrum antimicrobial properties verified (Selsted et al., Infect. Immun., 55:2281-2286 [1987]). Eight of its 31 residues were among those invariant in six rabbit and three human defensin peptides. The sequence of GPNP also included three nonconservative substitutions in positions otherwise invariant in the human and rabbit peptides. Of the defensins tested in a quantitative assay HNP-1, RatNP-1, and rabbit NP-1 possess the most potent antimicrobial properties, while NP-5 possesses the least amount of antimicrobial activity when tested against a panel of organisms in stationary growth phase. (Selsted et al., Infect. Immun., 45:150-154 [1984]; Ganz et al., J. Clin. Invest. 76:1427-1435 [1985]). Defensin peptides are further described in U.S. Pat. Nos. 4,543,252; 4,659,692; and 4,705,777 (each of which is incorporated herein by reference).

Accordingly, in some embodiments, the compositions of the present invention comprise one or more defensins selected from the group consisting of SEQ ID NOs: 37-95.

In preferred embodiments, suitable antimicrobial peptides comprise all or part of the amino acid sequence of a known peptide, more preferably incorporating at least some of the conserved regions identified in Table 2. In particularly preferred embodiments, the antimicrobial peptides incorporate at least one of the conserved regions, more usually incorporating two of the conserved regions, preferably conserving at least three of the conserved regions, and more preferably conserving four or more of the conserved regions. In preferred embodiments, the antimicrobial peptides comprise fifty amino acids or fewer, although there may be advantages in increasing the size of the peptide above that of the natural peptides in certain instances. In certain embodiments, the peptides have a length in the range from about 10 to 50 amino acids, preferably being in the range from about 10 to 40 amino acids, and most preferably being in the range from about 30 to 35 amino acids which corresponds generally to the length of the natural defensin peptides.

In some embodiments, the present invention provides antibodies (or portions thereof) fused to biocidal molecules (e.g., lysozyme) (or portions thereof) suitable for use with processed food products as a whey based coating applied to food packaging and/or as a food additive. In still other embodiments, the compositions of the present invention are formulated for use as disinfectants for use in food processing facilities. Additional embodiments of the present invention provide human and animal therapeutics.

V. Applications

The methods and compositions of the present invention find use in a variety of applications, including, but not limited to, those described below.

A. Exemplary Target Pathogens i) *Escherichia Coli* O157:H7

Preferred embodiments of the present invention provide effective therapeutic treatments and prophylactic methods for combating the foodborne pathogen *E. coli* O157:H7. *E. coli* O157:H7 is a common component of the normal flora of the bovine gastrointestinal tract. Surveys of clinically normal cattle detect *E. coli* O157:H7 shedding in the feces of about 1-25% of animals. (D. D. Hancock DD et al., Epidemiol. Infect., 113(2):199-207 [1994]; MMWR Morb. Mortal. Wkly. Rep., 48(36):803-805 [1999]; and National Dairy Heifer Evaluation Project, USDA APHIS NAHMS [1994]). Human infection by *E. coli* O157:H7 most often occurs through the fecal-oral route, either directly through handling of infected cattle, or more commonly as a result consuming contaminated meat products. Small-scale outbreaks of *E. coli* O157:H7 disease have been associated with petting zoos and agricultural fairs. (See e.g., G. C. Pritchard et al., Vet. Rec., 147:259-264 [2000]). Larger outbreaks of *E. coli* O157:H7 disease have been traced to the widespread dissemination and consumption of contaminated meat products such as ground beef. (J. Tuttle et al., Epidemiol. Infect., 122:185-192 [1999]).

Contamination of meat products with fecal matter harboring *E. coli* O157:H7 appears to occur primarily during slaughterhouse dehiding, evisceration, splitting, chilling, and fabrication operations. Further dissemination of *E. coli* O157:H7 to otherwise uncontaminated meat products also occurs during grinding, processing, and transportation of meat products. Because of the severity of *E. coli* O157:H7 disease and the potential for the contamination of large quantities of otherwise wholesome meat by a relatively small amount of contaminated meat, the recalls issued for potentially contaminated meat products are often very large.

Recent *E. coli* O157:H7 contaminated meat recalls, include the recall of 24 million pounds of ground beef by the Hudson Beef in 1997, and most recently the recall of 19 million pounds of ground beef by the ConAgra Beef Company in July 2002. Recalls of this magnitude are obviously very costly; not only for actual value of the beef being destroyed, but also the logistical effort required to collect and dispose of the contaminated beef. More importantly, immeasurable costs arise from decreased consumer confidence in the meat packing industry and in the wholesomeness of food supply generally.

*E. coli* O157:H7 is particularly pathogenic because it produces a multi-unit verotoxin (or a shiga-like toxin) protein that binds receptors in the kidney and gastrointestinal tract of man. This toxin produces a hemolytic uremic syndrome in children and the elderly, and a hemorrhagic colitis in adults. The Center for Disease Control reported over 70,000 cases of *E. coli* O157:H7 disease each year and 60 deaths annually. The symptoms of hemorrhagic colitis last an average of 8 days. This implies that over half a million work days are lost per year due to *E. coli* O157:H7 infection.

*E. coli* O157:H7 disease is a costly and frustrating zoonosis, in part because its epidemiology is well understood yet very difficulty to prevent. The recent massive dissemination of the organism I contaminated meat products is a function of the industrialization processes that are essential to providing affordable food.

Preferred embodiments of the present invention combat *E. coli* O157:H7, by providing chimeric murine-bovine monoclonal antibodies to provide passive immunity in host animals (e.g., bovines), to induce specific immunity in host animals due to the bovine portion of the antibody, to topically control *E. coli* O157:H7 post harvest. Additional preferred embodiments provide chimeric murine-bovine monoclonal antibody fusion proteins that directly reduce *E. coli* O157:H7 in host animals by providing highly controlled and targeted bactericidal microenvironments that destroy the pathogens without affecting normal microbiological flora.

ii) *Listeria Monocytogenes*

Ingestion of the bacterium *Listeria monocytogenes* probably occurs quite often, as the bacteria has been isolated in food products worldwide. (B. Lorber, Clin. Infect. Dis., 24:1-11 [1997]; and J. M. Farber and P. I. Peterkin, Microbiol. Rev., 55:476-511 [1991]). Development of Listeriosis, the invasive disease caused by *L. monocytogenes* ingestion, is determined primarily by the integrity of the host's immune system (predominantly cell-mediated immune defects) and possibly also by inoculum size. (See e.g., P. Aureli et al., New Engl. J. Med., 342:1236-1241 [2000]). *L. monocytogenes* crosses the mucosal barrier of the intestines and invades the bloodstream. The bacterium may disseminate to any organ, but has a clear predilection for the placenta and central nervous system (CNS), thus determining the main clinical syndromes caused by infection. Listeriosis is life-threatening zoonosis, especially in human fetuses and neonates, the elderly, and patients with certain predisposing conditions. Many cases of Listeriosis probably go unreported especially in perinates and newborns.

*L. monocytogenes* is a difficult bacterium to control because it thrives in vacuum packed food products and at temperatures typically used in food refrigeration. (S. Liu et al., Appl. Environ. Microbiol., 68(4):1697-1705 [2002]). Thus, *L. monocytogenes* is a particular problem in ready to eat foods that consumers expect are safe to eat with no further cooking. Typical food products contaminated with *L. monocytogenes* include unpasteurized or low acid dairy products and ready-to-eat (RTE) meat products such as luncheon meat and pates.

Many of the larger listeriosis outbreaks have been associated with fresh dairy products, especially Mexican soft cheeses and other non-aged or fermented cheese products. (M. J. Linnan et al., New Eng. J. Med., 319:823-828 [1988]). In specialty cheese production, *L. monocytogenes* has been found to accumulate in ripening rooms. (S. I. Pak et al., supra). Outbreaks have also been linked to processed and deli meat products, including turkey hot dogs, pate, and jellied tongue. (See e.g., C. Jacquet et al., Appl. Env. Microbiol., 61:2242-2246 [1995]; J. McLaughlin et al., Brit Med. J., 303:773-775 [1991]; and Morbidity and Mortality Weekly Reports, 47:1085-1086 [1998]). *L. monocytogenes* is however, easily destroyed by cooking. As *Listeria* is heat labile, food products that cooked prior to eating and served hot have a lower risk profile.

The bacterium often contaminants food processing equipment, where it is typically found as a biofilm on steel and glass parts. *L. monocytogenes* tends to form biofilms on containers used to store food products. (A. C. Wong, J. Dairy Sci., 81(10):2765-2770 [1998]). It is also a common environmental contaminant of food storage facilities. (See e.g., M. S. Chae and H. Schraft, Int. J. Food. Microbiol., 62:103-111 [2000]). Thus, a pathogen originally considered an "environmental" organism on farms has invaded industrial food preparation facilities. Strains of *L. monocytogenes* have emerged with progressive resistance to antimicrobial agents. (C. Arizcun et al., J. Food Prot., 61:731-734 [1988]). Contamination of food processing equipment and storage often seed small amounts of bacteria onto food products which multiply during refrigeration. The length of time food is kept refrigerated, both at the retail outlet and in home, and the actual storage temperatures influence the risk that even low levels of initial *L. monocytogenes* contamination will grow to become problematic. Outbreaks of listeriosis have been associated with breakdowns in the environmental controls at food processing facilities (e.g., during plant renovation). Given the capacity of *L. monocytogenes* to grow under refrigeration, even very low levels of *L. monocytogenes* contamination in food products as they leave the processor can ultimately result in inoculums large enough to cause lethal infections in the consumer. Consequently, the present invention contemplates controlling foodborne listeriosis requires focusing on post-processing food handling and storage.

*L. monocytogenes* is recognized as an apparent and inapparent infection of livestock and is widespread in agricultural environments. (See e.g., L. Hassan et al., J. Dairy Sci., 83(11): 2441-2447 [2000]). *L. monocytogenes* is widespread in the environment and shed in the feces and milk of inapparently infected cattle. (L. Hassan et al., supra). Even low levels of *L. monocytogenes* contamination are enough to support the continued growth of the organism and are the primary source of human listeriosis.

Listeriosis is a serious disease. In milder its forms, listeriosis is a febrile illness with gastrointestinal signs but often progresses to bacteremia and meningitis with nervous system clinical manifestations including headache, loss of balance, and convulsions. Incubation periods can be several weeks making epidemiologic investigation more difficult. Listeriosis is particularly serious for pregnant women, infants, and individuals with compromised immune systems. (See e.g., A. Schuchat et al., Clinical Microbiol. Rev., 4:169-183 [1991]). Individuals with Acquired Immune Deficiency Syndrome (AIDS) are almost 300 times more likely to contract listeriosis than people with normally functioning immune systems. (J. G. Morris and M. Potter, Emerging Infectious Diseases, 3:435-441 [1997]). Diabetics and those affected by cancer and kidney disease are also at greater risk of contracting Listeriosis and are more prone to serious nervous system manifestations of the disease. Listeriosis in pregnant women can result in premature birth, still births, or birth of a critically infected child. Perinates and newborns are particularly at risk as the relative immaturity of their immune systems has been shown to contribute to the severity of disease (See e.g., L. Slutzker and A. Schuchat, Listeriosis in humans. In: *Listeria*, Listeriosis and Food Safety, E. T. Ryser and E. M. Marth eds. Marcel Dekker Inc., New York, N.Y. pp. 75-95 [1999]. Human foodborne listeriosis tends to result in either sporadic cases or epidemics depending on whether a common food source infects a group of people (H. R. Ibrahim et al., FEBS Lett., 506(1):27-32 [2001]). Contaminated meats, seafood, vegetables, fruits, and dairy products have all been the source of sporadic cases of listeriosis (S. I. Pak et al., Prev. Vet. Med., 53(1-2):55-65 [2002]).

iii) *Cryptosporidium Parvum*

*Cryptosporidium parvum* is a zoonotic apicomplexan parasite recognized as the cause of large outbreaks of acute diarrheal disease. The disease caused by *Cryptosporidium* infection is called cryptosporidiosis. Cryptosporidiosis has emerged as an important opportunistic infection in patients infected with HIV. With the advent of more effective HIV therapies, the association between *Cryptosporidium* infection and HIV has lessened in the US, however opportunistic *Cryptosporidiousis* following infection by HIV continues to be a major problem in developing countries.

*Cryptosporidium* is also recognized as a leading cause of traveler's diarrhea. An acutely debilitating diarrheal disease, accompanied by stomach cramps, cryptosporidiosis typically lasts 2-10 days. In the otherwise healthy host, cryptosporidiosis is rarely fatal, but deaths occur among the immunocompromised including AIDS patients, chemotherapy patients, malnourished individuals, and the elderly, who may become chronically diarrheic and in whom the parasite may establish hard-to-eliminate hepatobiliary and pancreatic infections.

*C. parvum* infects cattle and other livestock usually within the first few hours or days of life. Infected animals can become long-term shedders of *C. parvum* oocysts. *C. parvum* is an economically important cause of diarrheal disease and mortality among calves which provide a significant reservoir for human infection. In swine, clinical disease cryptosporidiosis is less common, but *C. parvum* has been recognized as a highly prevalent contaminant of swine manure holding facilities.

*C. parvum* oocysts can survive for extended periods of time in water and soil contaminated from human or animal fecal shedding. The oocysts are not inactivated by chlorination, nor removed by many water filtration systems. Drinking water, recreational water contact, and fecally contaminated foodstuffs are the principal sources of infection for humans. Type 1 and 2 *C. parvum* genotypes are epidemiologically and genetically distinct, although overlap occurs and heterogeneous infections can occur. Type 1 is transmitted from human to human, while type 2 is zoonotic and transmitted between cattle and other livestock, and humans. While genetic polymorphisms occur in both type 1 and 2 isolates, the extent of epitope homology between the genotypes and cross-protection is not fully understood. Dual infections may occur, but with no reproductive mixing of the genotypes. Nevertheless, the present invention shows that three functionally defined antigens are conserved at the protein level between several type 1 and type 2 isolates. These antigens, CSL, P23 and GP25-200, were originally defined on type 2 isolates and previously shown to be the targets of neutralizing antibodies. The apparent conservation of antigens indicates that the compositions of the present invention using monoclonals antibodies to these antigens as neutralizing agents, either alone or to target a biocide to the parasite surface, will have application to both Type 1 and 2 infections. The present invention further contemplates compositions comprising polyvalent antibody passive immunotherapies to treat epidemics of unknown origin.

Large outbreaks of human cryptosporidiosis demonstrate the potential for *Cryptosporidium* to be used as a bioterrorism agent. A 1993 outbreak of cryptosporidiosis in Milwaukee resulted in over 400,000 cases of clinical disease and several dozen deaths, following dissemination of *C. parvum* through the public water supply. The Milwaukee experience suggests that large waterborne or food borne outbreaks of cryptosporidiosis could be brought about by deliberate contamination. With the ratio of infective oocysts per gram of feces shed by an individual to the infective dose approximating one million to one (shedding $10^6$ or $10^7$ oocysts per gram, compared to an infective dose 10-100), the potential for producing major urban outbreaks is real.

*C. parvum* has several attributes that lend it for use as a potential bioterrorism agent: infectious oocysts are very hardy and easily transported; infective oocysts are shed in very large numbers but have a low infective dose; cryptosporidiosis is unlikely to be fatal to the terrorist handler; oocysts are readily available without access to reference collections or high security laboratories and can be easily propagated in neonatal ruminants (up to ~$10^{10}$ oocysts from a single calf); and widespread dissemination can be achieved in food or water. Given a high background incidence of *C. parvum* infections, an acute epidemic would be harder to trace back to a point source. Nevertheless, clinical signs are dramatic enough to cause panic, and to allow terrorist claims of responsibility to ring true. *C. parvum* thus fits the profile of an organism which might be deployed by a "low tech" terrorist group without access to a well-developed laboratory infrastructure.

The recent British detection of "ricin laboratories" indicate that low tech bioterrorism is today's reality. If the intent of bioterrorism is to produce mass hysteria rather than mass disease and fatalities, a few cases of cryptosporidiosis implicating contamination of a major food or water supplies could have a dramatic psychological effect.

Water distribution systems across the country are relatively difficult to secure. Security of water supply is also of concern in assuring a safe food supply. In an urban society dependent on complex food distribution chains, a point source contamination could affect people across a wide geographic area. For example, the recent nationwide recall of 28 million pounds of processed turkey due to *Listeria* contamination in a single processing plant illustrates that point source food contamination can have a very wide ripple effect. With only a moderate increment in microbiologic expertise, the effects of food bioterrorism could be devastating.

Dairy effluent is considered an important source of natural *C. parvum* infection, likewise, swine effluent is suspected as being reservoir for infection. Controlling infection in animal populations would help reduce the environmental risk of natural infections. Accordingly, certain embodiments of the present invention provide compositions to control zoonotic pathogens in animal reservoirs and agricultural environments.

Prior to the present, there were no effective parasite-specific drug therapies to control or curtail cryptosporidiosis in man or animals. Existing treatments are palliative and directed avoiding onset of dehydration. (S. Tzipori and H. Ward, Microbes Infect., 4:1047 [2002]). Naturally occurring cases of cryptosporidiosis in human and animal hosts with normal immunological systems can be severe, but are typically self limiting. (C. L. Chappell et al., Amer. J. Trop. Med. Hyg., 60:157-164 [1999]). In certain embodiments, colostral antibodies fed to calves limit infection and prevent clinical disease. In some other embodiments, polyclonal hyperimmune antibodies raised against *C. parvum* effectively limit clinical cases of the disease while allowing some active immunity to develop.

The present invention provides antibody-based immunoprophylaxis and immunotherapy that effectively control acute *C. parvum* infections. The present invention contemplate that the efficacy of compositions and methods of passive immunotherapy comprising administering antibodies specifically developed against neutralization-sensitive epitopes is distinguishable from the host-produced antibodies in protection against natural infection, which depends on competent cell mediated immune responses (M. Riggs, Microbes Infect., 4:1067 [2002]).

Preferred embodiments provide compositions and methods for administering passive immunotherapies against pathogens (e.g., *C. parvum* infections). Faced with a population exposed to deliberately contaminated food or water, or in a battle theater setting, a rapidly deployable, rapidly effective, passive immunotherapies are strategically and clinically very valuable. In some of these embodiments, the present invention provides orally administered monoclonal antibody compositions that specifically target pathogens (e.g., parasites) and either prevent infection, or reduce an existing infection to subclinical levels and abbreviate existing clinical effects.

In some embodiments, the present invention provides monoclonal antibodies against defined apical complex and surface-exposed antigens to specifically neutralize infective stages of *C. parvum* in vitro and in vivo. The present invention also provides Previously unavailable recombinant antibodies to *C. parvum*. Prior to the present invention, high cost and inefficient production systems for recombinant and hybridoma monoclonals alike have generally removed widespread immunoprophylaxis and/or immunotherapies for cryptosporidiosis form serious clinical consideration.

Some preferred embodiments of the present invention make use of an extensive bank of hybridoma lines directed to *cryptosporidial* antigens. A large number of *C. parvum* antigens of distinct function have been identified and characterized. (M. W. Riggs, Microbes. Infect., 4:1067 [2002]). Several antigens in particular have shown potential for independent targeting to neutralize sporozoite and merozoite infectivity, including, but not limited to, CSL, P23, and GP25-200. Briefly, CSL (~1300 kDa) is an apical complex-derived glycoprotein expressed on the surface of sporozoite and merozoite infective stages. After antibody binding to CSL, sporozoites release the antigen in membranous antibody-CSL complexes and are rendered non-infective. (M. W. Riggs et al., J. Immunol., 158:1787-1795 [1997]). Since CSL has been shown to contain a ligand for a surface receptor on human intestinal epithelial cells (See, R. C. Langer and M. W. Riggs, Infect. Immun., 67:5282-5291 [1999]; and R. C. Langer et al., Infect. Immun., 69:1661-1670 [2001]), blocking of CSL is contemplated to account for the efficacy of anti-CSL antibodies in inhibiting sporozoite attachment. P23 (~23 kDa) is a surface protein of sporozoites and merozoites believed to be involved in motility and invasion processes (See, L. E. Perryman et al., Vaccine, 17:2142-2149 [1999]). Monospecific antibodies to P23 have been shown to curtail disease in neonatal calves. (L. E. Perryman et al., supra). GP25-200 is a glycoprotein complex of variable size, found in the apical complex and on the surface of sporozoites and merozoites. (M. W. Riggs et al., supra). Schaefer et al. demonstrated that when hybridoma derived monoclonal antibodies to CSL, P23, and GP25-200 were applied singly, or in combination, significant sporozoite neutralization could be obtained. (D. A. Schaefer et al., Infect. Immun., 68:2608-2616 [2000]).

In some embodiments, optimal protection in neonatal mice is achieved by combining three antibodies: 3E2 (IgM) to target CSL; 3H2 (IgM) to target GP25-200; and IE10 (IgG1) to target P23. When these three antibodies are orally administered, individually, in the neonatal mouse infection model, they are able to reduce intestinal infection by 50-60%. When these antibodies are administered as a polyvalent "cocktail" the three monoclonal antibodies reduced intestinal infection by 86-93%. Preferred embodiments of the present invention provide recombinant analogues of 3E2, 3H2, and 1E10 antibodies. Additional preferred embodiments provide fusion proteins comprising cryptosporocidal enzymes and antibodies (e.g., IgG), or portions thereof, including, but not limited to, 3E2, 3H2, 1E10, and 4H9. 4H9 is a second antibody directed to GP25-200. It is an IgG1 antibody that is though to recognize a different epitope on GP25-200 than does 3H2. In some embodiments, 4H9 is able to reduce infection in neonatal mice by ~50% when administered orally. Thus, ion stil other embodiments, compositions comprising 1E10 and 4H9 provide vehicles for delivering biocides to two different neutralization-sensitive molecules on the surface of sporozoites and merozoites.

The present invention contemplates that using a monoclonal antibody fusion protein to direct otherwise naturally occurring biocides to specific pathogenic organisms (e.g., *E. coli* O157:H7, *L. monocytogenes*, *Cryptosporidium parvum* and the like) has wide applicability in human and animal health. The present invention further contemplates compositions to control other pathogenic feedlot organisms including, but not limited to, *E. coli* K99 in calves and *E. coli* K88 in piglets.

In still further embodiments, the present invention provides embodiments to control other pathogens responsible for foodborne illnesses and other emerging infectious diseases as a component of the Nation's food security and bioterrorism response. For example, some embodiments of the present invention are focused on controlling potential foodborne bioterrorism agents such as, *Clostridium botulinum*, *Clostridium perfringens*, *Staphylococcus aureus*, *Staphylococcus epidermidis*, *Staphylococcus pneumoniae*, *Staphylococcus saprophyticus*, *Shigella dysenteriae*, *Salmonella typhi*, *Salmonella paratyphi*, *Salmonella enteritidis*, fungal agents and the like.

iii). Other Exemplary Target Pathogens

In some other embodiments, the present methods and compositions are directed to specifically controlling (e.g., therapeutic treatments or prophylactic measures) diseases caused by the following pathogens: *Bartonella henselae*, *Borrelia burgdorferi*, *Campylobacter jejuni*, *Campylobacter fetus*, *Chlamydia trachomatis*, *Chlamydia pneumoniae*, *Chylamydia psittaci*, *Simkania negevensis*, *Escherichia coli* (e.g., O157:H7 and K88), *Ehrlichia chafeensis*, *Clostridium botulinum*, *Clostridium perfringens*, *Clostridium tetani*, *Enterococcus faecalis*, *Haemophilius influenzae*, *Haemophilius ducreyi*, *Coccidioides immitis*, *Bordetella pertussis*, *Coxiella burnetii*, *Ureaplasma urealyticum*, *Mycoplasma genitalium*, *Trichomatis vaginalis*, *Helicobacter pylori*, *Helicobacter hepaticus*, *Legionella pneumophila*, *Mycobacterium tuberculosis*, *Mycobacterium bovis*, *Mycobacterium africanum*, *Mycobacterium leprae*, *Mycobacterium asiaticum*, *Mycobacterium avium*, *Mycobacterium celatum*, *Mycobacterium celonae*, *Mycobacterium fortuitum*, *Mycobacterium genavense*, *Mycobacterium haemophilum*, *Mycobacterium intracellulare*, *Mycobacterium kansasii*, *Mycobacterium malmoense*, *Mycobacterium marinum*, *Mycobacterium scrofulaceum*, *Mycobacterium simiae*, *Mycobacterium szulgai*, *Mycobacterium ulcerans*, *Mycobacterium xenopi*, *Corynebacterium diptheriae*, *Rhodococcus equi*, *Rickettsia aeschlimannii*, *Rickettsia africae*, *Rickettsia conorii*, *Arcanobacterium haemolyticum*, *Bacillus anthracis*, *Bacillus cereus*, *Lysteria monocytogenes*, *Yersinia pestis*, *Yersinia enterocolitica*, *Shigella dysenteriae*, *Neisseria meningitides*, *Neisseria gonorrhoeae*, *Streptococcus bovis*, *Streptococcus hemolyticus*, *Streptococcus mutans*, *Streptococcus pyogenes*, *Streptococcus pneumoniae*, *Staphylococcus aureus*, *Staphylococcus epidermidis*, *Staphylococcus pneumoniae*, *Staphylococcus saprophyticus*, *Vibrio cholerae*, *Vibrio parahaemolyticus*, *Salmonella typhi*, *Salmonella paratyphi*, *Salmonella enteritidis*, *Treponema pallidum*, Human rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida*, *Cryptcooccus*, *Cryptosporidium*, *Giardia lamblia*, *Microsporidia*, *Plasmodium vivax*, *Pneumocystis carinii*, *Toxoplasma gondii*, *Trichophyton mentagrophytes*, *Enterocytozoon bieneusi*, *Cyclospora cayetanensis*, *Encephalitozoon hellem*, *Encephalitozoon cuniculi*, among other viruses, bacteria, archaea, protozoa, fungi, and the like).

The present invention is not limited to the exemplary microorganisms described herein. One skilled in the art understands that the methods and compositions of the present invention are suitable for the targeting of any microorganism or group or class of microorganism.

B. Biofilms

In some embodiments, the methods and compositions of the present invention target bacteria present as a biofilm. *Listeria monocytogenes* can form biofilms on a variety of materials used in food processing equipment and other food and non-food contact surfaces (Blackman, J Food Prot 1996; 59:827-31; Frank, J Food Prot 1990; 53:550-4; Krysinski, J Food Prot 1992; 55:246-51; Ronner, J Food Prot 1993; 56:750-8). Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990:195-231; Costerton et al., Annu Rev Microbiol 1995; 49:711-45).

Biofilm formation is a serious concern in the food processing industry because of the potential for contamination of food products, leading to decreased food product quality and safety (Kumar C G and Anand S K, Int J Food Microbiol 1998; 42:9-27; Wong, J Dairy Sci 1998; 81:2765-70; Zottola and Sasahara, Int J Food Microbiol 1994; 23:125-48). The surfaces of equipment used for food handling or processing are recognized as major sources of microbial contamination. (Dunsmore et al., J Food Prot 1981; 44:220-40; Flint et al., Biofouling 1997; 11:81-97; Grau, In: Smulders FJM ed. Amsterdam: Elsevier, 1987:221-234; Thomas et al., In: Smulders FJM ed. Amsterdam: Elsevier, 1987:163-180). Biofilm bacteria are generally hardier than their planktonic (free-living) counterparts, and exhibit increased resistance to antimicrobial agents such as antibiotics and disinfectants. It has been shown that even with routine cleaning and sanitizing procedures consistent with good manufacturing practices, bacteria can remain on equipment, food and non-food contact surfaces and can develop into biofilms. In addition, *L. monocytogenes* attached to surfaces such as stainless steel and rubber, materials commonly used in food processing environments, can survive for prolonged periods (Helke and Wong, J Food Prot 1994; 57:963-8). This would partially explain their ability to persist in the processing plant. Common sources of *L. monocytogenes* in processing facilities include equipment, conveyors, product contact surfaces, hand tools, cleaning utensils, floors, drains, walls, and condensate (Tomkin et al., Dairy, Food Environ Sanit 1999; 19:551-62; Welbourn and Williams, Dairy, Food Environ Sanit 1999; 19:399-401).

C. Plant Pathogens

In still further embodiments, the present invention provides methods and compositions targeted towards plant pathogens. Plant fungi have caused major epidemics with huge societal impacts. The Irish potato famine, with its consequent economic disaster and human population displacement, was the result of the sudden introduction of the fungus *Phytophthora infestans*.

South American cocoa crops are under threat of two major fungal diseases: witches broom caused by *Crinipellis perniciosa* and frosty pod (*Moniliophthora roreri*), which together threaten the viability of the chocolate production industry in the western hemisphere.

*Phytophthora* blight, caused by the oomycete *Phytophthora capsici*, has become one of the most serious threats to production of cucurbits (cucumbers, squash, pumpkins) and peppers, both in the United States and worldwide (Erwin, D. C., and Ribeiro, O. K. 1996. *Phytophthora* Diseases Worldwide. American Phytopathological Society, St. Paul, Minn.).

Banana crops worldwide are affected by Black Sigatoka is caused by the ascomycete, *Mycosphaerella fijiensis*. *Fusarium* scab affects small grain crops (wheat and barley). *Ganoderma* spp fungi have produced deaths of ornamental palms, as do several species of *Phytophthora* (Elliott and Broschat, T. K. 2001. Palms 45:62-72; Nagata and Aragaki, M. 1989. Plant Dis. 73:661-663).

Plants are also affected by bacteria and viruses. *Burkholderia cepacia* is a bacterium which produces economic losses to onion crops (Burkholder 1950. Phytopathology 40:115-118). Numerous plant viruses cause significant crop losses worldwide. Exemplary of such plant viruses are soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus.

D. Sanitation

In yet other embodiments, the methods and compositions of the present invention find use in the sanitation of household and other areas. *Listeria* spp are common contaminants of the domestic environment. As many as 47% of households sampled were contaminated, with dishcloths, and drain areas being common sites of contamination. (Beumer et al., Epidemiol Infect. 1996 December; 117(3):437-42).

*Pseudomonas aeruginosa* is frequently isolated from showers and baths and hot tubs (Zichichi et al., Int J Dermatol. 2000 April; 39(4):270-3; Silverman and Nieland, J Am Acad Dermatol. 1983 February; 8(2):153-6).

Where a family member has an infectious disease, transmission may occur through contamination of domestic objects (Barker et al., J Appl Microbiol. 2000 July; 89(1):137-44).

Domestic food preparation and storage areas are also a source of bacterial food contaminants. The public is showing increasing awareness of the need to control domestic microbial contamination (Mattick et al., Int J Food Microbiol. Aug. 25, 2003; 85(3):213-26; Kusumaningrum et al., Int J Food Microbiol. Aug. 25, 2003; 85(3):227-36).

E. Building Structures

In other embodiments, the present invention provides methods of targeting building structures. There has been increasing public attention to the potential health risks of mold exposure, particularly in wet buildings. A variety of molds have been isolated from both damaged homes and businesses, including agents that secrete toxigenic materials. *Stachybotrys chartarum* is a fungus that has become notorious as a mycotoxin producer that can cause animal and human mycotoxicosis. Indeed, over the past 15 years in North America, evidence has accumulated implicating this fungus as a serious problem in homes and buildings and one of the causes of the "sick building syndrome." (Mahmoudi et al., J Asthma. 2000 April; 37(2):191-8).

*Legionella* spp. bacteria replicate in manmade water containing structures, especially when these are heated, such as industrial cooling towers, heating and air conditioning systems. Legionnaires disease pneumonia is contracted by susceptible individuals that breathe water droplets from such sources. Preventive and remedial treatment of water containing structures is needed to eliminate the source of infection to building inhabitants (Shelton et al., AIHAJ. 2000 September-October; 61(5):738-42).

F. Military and Bioterrorism Applications

The methods and compositions of the present invention further find use in military and bioterrorism applications. For example, in some embodiments, the methods and compositions of the present invention are used in the decontamination of surfaces exposed to unknown bacteria and potentially other microorganisms (e.g., military equipment and personal protective gear).

In yet other embodiments, microorganisms engineered for use in combatting bioterror agents (e.g., *B. Anthracis*, smallpox, etc.) are targeted by the methods and compositions of the present invention.

The methods and compositions of the present invention further find use in combating unknown and drug resistant organisms. The prevalence of bacteria that resist standard antibiotic therapy is increasing rapidly. Furthermore, the ability to engineer organisms with multiple drug resistance to standard antibiotics creates a significant threat in bioweapons development. Because the broad spectrum antimicrobials of the present invention are suitable for use against broad classes of pathogens, they can respond to unknown bacteria and their bactericidal effect is independent of antibiotic resistance mechanisms.

G. Medical Applications

The methods and compositions of the present invention additionally find use in the treatment of subjects (e.g., humans) infected with a microorganism (e.g., food borne pathogens). The methods and compositions of the present invention are particularly well suited for use against antibiotic resistant organisms are targeted by the methods and compositions of the present invention.

VI. Cryptosporidium Biocides

The present invention is not limited to the use of fusion protein biocides. As described above, *Cryptosporidium parvum* is a common cause of gastrointestinal infection for which there is presently no parasite-specific curative therapy. In some embodiments, the present invention provides isolated biocides for use against *Cryptosporidium parvum* (e.g., sporozoites). Experiments conducted during the course of development of the present invention demonstrated that several biocides had *Cryptosporidium parvum* sporozoite killing activity, as well as the ability to reduce *Cryptosporidium parvum* infectivity. The biocides evaluated have the further advantage of showing minimal toxicity against human cells. The biocides of the present invention thus find use in the treatment of objects (e.g., swimming pools) and food products (e.g., drinking water) contaminated with *Cryptosporidium*.

The present invention is not limited to a particular biocide. Any biocide that is effective against *Cryptosporidium parvum* (e.g., killing of spores or reduction in infectivity) may be utilized. Preferred biocides are those that are non-toxic to animal (e.g., human) cells. Exemplary biocides include, but are not limited to, lactoferrin hydrolysate, lactoferrin b, cathelicidin, indolicidin, beta-defensin-2, deta-defensin-1, phopholipase A2, and phospho-inositol specific phospholipase C.

DETAILED DESCRIPTION OF THE INVENTION

The present invention relates to constructs that encode novel microorganism targeting molecules (e.g., innate immune receptors ligands or monoclonal antibodies), novel fusion proteins, and chimeric monoclonal antibodies and to methods of using and producing the same. In particular, the present invention relates to methods of producing novel monoclonal antibody biocide (e.g., bactericidal enzymes) fusion proteins in transgenic animals (e.g., bovines) and in cell cultures. The present invention also relates to therapeutic and prophylactic methods of using monoclonal antibody biocide fusion proteins in health care (e.g., human and veterinary), agriculture (e.g., animal and plant production), and food processing (e.g., beef carcass processing). The present invention also relates to methods of using monoclonal antibody biocide fusion proteins in various diagnostic applications in number of diverse fields such as agriculture, medicine, and national defense.

Certain embodiments of the present invention relate to the production of novel monoclonal antibodies and chimeric monoclonal antibody fusion proteins in host cells containing multiple integrated copies of an integrating vector. Preferred embodiments of the present invention utilize integrating vectors (i.e., vectors that integrate via an integrase or transposase or have the capability to code for these enzymes) to create cell lines containing a high copy number of a nucleic acid encoding a gene of interest. The transfected genomes of the high copy number cells are stable through repeated passages (e.g., at least 10 passages, preferably at least 50 passages, and most preferably at least 100 passages). Furthermore, in preferred embodiments, the host cells of the present invention are capable of producing high levels of protein (e.g., more than 1 pg/cell/day, preferably more than 10 pg/cell/day, more preferably more than 50 pg/cell/day, and most preferably more than 100 pg/cell/day).

Additional embodiments provide methods for the production of transgenic non-human animals that express novel proteins in their tissues (e.g., mammary glands). In preferred embodiments, the transgenic animals are non-human ruminant (*Ruminantia*) mammals. In other preferred embodiments, the transgenic animals are ungulates. In particularly preferred embodiments, the mammals are female ruminants (e.g., bovines) that preferentially express the novel proteins in their mammary glands. In some additional embodiments, the novel protein compositions produced in the transgenic animals are collected, purified, and subsequently incorporated into a variety of additional compositions (e.g., food additives, pharmaceuticals, disinfecting agents, etc.) and/or used in a variety of therapeutic or prophylactic methods. In some embodiments, the proteins of interest (the novel fusion proteins disclosed herein) are mixed with colostrum (or colostrum substitute(s)) and subsequently feed to nursing feedlot animals (e.g., beef calves, piglets, lambs, kids, and the like). In other embodiments, the proteins of interest are formulated with one or more carriers (e.g., whey) and used in the meat processing industry either a topical disinfecting agent applied to animal carcasses or as an edible supplement mixed into finished meat products. In still further embodiments, the proteins of interest (e.g., novel monoclonal antibodies and chimeric monoclonal antibody fusion proteins disclosed herein) are purified from the lactation of transgenic non-human animals and subsequently processed and formulated for administration to subjects (e.g., humans and non-human animals) as therapeutic or prophylactic medicaments.

Further embodiments of the present invention provide methods for producing transgenic non-human animals by the introduction of exogenous DNA into pre-maturation oocytes and mature, unfertilized oocytes (i.e., pre-fertilization oocytes) using retroviral vectors that transduce dividing cells (e.g., vectors derived from murine leukemia virus [MLV], Moloney murine leukemia virus [MMLV], and the like). In addition, the present invention provides methods and compositions for cytomegalovirus promoter-driven, as well as, mouse mammary tumor LTR expression of various recombinant proteins. The present invention is not limited however to the aforementioned constructs, promoters, and other genetic elements. Indeed, the present invention provides numerous examples of contemplated genetic constructs (e.g., retroviral vectors) and methods of producing stably transfected cell lines (e.g., mammalian, amphibian, insect, and plant) and transgenic non-human animals (e.g., bovines).

In some preferred embodiments, retrovector transgenic technologies (described in greater detail herein) are used to overcome problems inherent in earlier methods for creating transgenic mammals. In preferred embodiments, unlike earlier transgenic methods, genes of interest (e.g., genes encoding at least a portion of a recombinant antibody) are introduced into unfertilized oocytes (e.g., bovine oocytes). After entry of the retroviral RNA into the cell, and reverse transcription into DNA, the integration of the DNA provirus into the host cell genome is mediated by the retroviral integrase and specific nucleotide sequences at the ends of the retroviral genome. By introducing genes to the oocyte (e.g., a bovine oocyte) at metaphase II arrest, the vector has access to the oocyte DNA when there is no nuclear membrane in place. The present invention contemplates this technology negates the need for dividing cells for retroviral integration to occur. Depending on the conditions, such integrations can occur at one or several independent sites in the genome and are transmitted in standard Mendelian patterns upon subsequent animal (e.g., bovine) breeding. The integrated gene is transcribed like other indigenous cell genes, and the proteins it encodes are expressed at high levels. In still other preferred embodiments, the retrovector backbone used lacks the genes essential for viral structure and enzyme functions, therefore the retroviral constructs are replication defective. In yet other embodiments, the present invention uses constructs that preclude the need for a selectable marker. Importantly, preferred embodiments contemplate that the removal of selectable markers (e.g., antibiotic-dependent selection markers) provides a significant advantage, especially upon consideration of regulatory requirements for transgenic livestock.

In some of preferred embodiments directed to producing transgenic animals, the contemplated approach has major advantages. For example, the efficiency of transgenic live births using the contemplated transgenic methods is high e.g., from about 25% -75% of animals (cattle) born when genes without a selection marker are used. Additionally, in preferred embodiments, retroviral genes insert as single copies, thus decreasing the risk of genetic instability upon subsequent cell replication, which tends to splice out tandem repeats of genes typical in pronuclear injection and nuclear transfer technologies. The present invention further contemplates in some preferred embodiments, where transgenes are inserted prior to fertilization the risk of producing mosaic animals, which are only transgenic in some tissues but not all, is greatly reduced.

Exemplary compositions and methods of the present invention are described in more detail in the following sections: I. Production of recombinant antibodies; II. Production of recombinant chimeric antibodies; II. Production of pathogen specific monoclonal antibodies in a multigenic expression system; IV. Comparison of murine and chimeric murine-bovine antibodies; and V. Transgenic animal technologies; VI. Considerations for combating *Cryptosporidium* and other parasites; VII. Transgenic plant technologies; and VIII. Pharmaceutical compositions.

I. Production of Recombinant Antibodies

The present invention contemplates obtaining hybridoma cell lines that produce monoclonal antibodies against particular pathogens of interest (e.g., *E. coli* strain O157:H7) from one or more sources (e.g., ATCC). The cell lines are subsequently used to isolate the heavy and light chain genes that encode for pathogen (e.g., *E. coli* O157:H7 and *Listeria monocytogenes*) specific monoclonal antibodies according to standard molecular biology methods.

For example, in one embodiment, hybridoma cell line ATCC HB 10452, which makes monoclonal antibody 4E8C12 specific for *E. coli* O157: H7 and O26:H11, are grown according to the depositors instructions. The cells are maintained in cRPMI at 37° C. and 5% $CO_2$ atmosphere and split biweekly at a 1:10 ratio. In another example, monoclonal antibody hybridomas to the pathogen *L. monocytogenes* from the cell line ATCC 4689-4708 are likewise grown according to the depositors instructions. In some embodiments, candidate monoclonal antibodies are chosen based upon their binding affinity to the pathogen of interest (e.g., *L. monocytogenes*) as well as their binding specificity that in certain instances includes as many different pathogen serotypes as possible. In some other embodiments, candidate monoclonals preferably show no or only weak cross-reaction with other species of bacteria and mammalian cells.

These cultures are expanded and grown in roller bottles under the described conditions to allow production of approximately milligram amounts of purified monoclonal antibodies. In preferred embodiments, the antibodies are purified using any suitable protocol such as ammonium sulfate precipitation. In some embodiments, the purified monoclonal antibodies are used to perform various in vitro functionality tests. For example, the present invention contemplates using purified monoclonal antibodies to perform affinity and specificity tests in order to select for the antibodies that have the best binding properties to the surface of the pathogen of interest (e.g., *L. monocytogenes*) and/or that include binding to a broad range of serotypes. Contemplated functionality tests include, but are not limited to, enzyme-linked immunosorbent assays (ELISA) and competitive ELISA assays. In one embodiment, varying concentrations of different monoclonal antibodies are allowed to bind to immobilized heat killed pathogens (e.g., *L. monocytogenes*). In another embodiment using a competitive assay, various concentrations of competing antigen are added to the wells of test plate and the binding of the monoclonal antibodies is measured. In yet another embodiment, quantitative immunofluorescence assays are used to allow the determination of binding affinity based on fluorescence intensity per cell. The present invention contemplates that by determining the affinity of the monoclonal antibodies based on their binding capacity to the pathogen of interest (e.g., *L. monocytogenes*), the present invention allows the selection of the one monoclonal antibody that is best for topical applications against viable pathogens.

Cells from the highest affinity hybridoma clone will be used to extract total RNA with the purpose of isolating the monoclonal antibody-specific heavy and light chain gene transcripts. Upon total RNA extraction, the RNA is reverse transcribed using standard molecular biology kits and protocols, such as the RIBOCLONE cDNA synthesis system from Promega (Promega Corp., Madison, Wis.). Preferably, the procedures used create double stranded cDNA of all RNA transcripts in a cell, including the transcripts from the murine heavy and light chain genes. The total cDNA is used as a template to specifically amplify the mouse IgG2a heavy chain and the Igk light chain. Site-directed mutagenesis primers are used to amplify these sequences. The present invention contemplates that the use of these primers adds short sequences of DNA, and introduces suitable restriction sites thus allowing direct cloning of the product into the retrovector backbone.

In preferred embodiments, once the genes for the murine heavy and light chain have been isolated, they are separated by an IRES element and inserted into the retrovector expression system under the control of the simian cytomegalovirus and the bovine alpha-lactalbumin promoter. In particularly preferred embodiments, the genes for the murine heavy and light antibody chains are cloned into the GPEX gene product expression system under the control of the simian cytomegalovirus (sCMV) promoter (Gala Design, Inc., Middleton, Wis.) or other suitable multigenic gene expression systems. This process allows for the production of cell lines that secrete high levels of the monoclonal antibodies.

In particular, the heavy chain followed by an internal ribosome entry site (IRES) element are cloned into the retrovector backbone at the same site. Similarly, the light chain is then cloned into the retrovector backbone. Once the retroviral construct is complete, quality control sequencing will confirm that all the elements are present. The present invention contemplates that the use of the IRES element in between heavy and light chain genes yields fully functional antibodies expressed and secreted into the medium at exceptionally high levels (e.g., >100 pg/cell/day in CHO cells). In some preferred embodiments, after the retroviral constructs are complete, quality control sequencing is used to confirm that all the elements are present. The retrovector construct are then used to transform host cells along with the plasmid that encodes the vesicular stomatitis virus glycoprotein (VSV-G) used for pseudotyping the retrovirus. This procedure creates intermediate level viral titer that is used to infect production cell lines (e.g., 293H or CHO cells). The population of transduced cells are subjected to clonal selection based on the antibody levels present in the medium supernatant. The clone with the highest level of antibodies secreted into the supernatant is selected to produce milligram amounts of murine monoclonal antibody 4E8C12. In preferred embodiments, the recombinant antibodies are purified from cell supernatants using standard techniques well known to those in the art.

FIG. 1 shows one contemplated retroviral construct for expression of murine and chimeric bovine murine antibodies with lysozyme. In some cell culture expression embodiments, the alpha-lactalbumin promoter is replaced with simian cytomegalovirus promoter.

II. Production of Recombinant Chimeric Antibodies

In some embodiments, the bovine IgG1 and IgG2 heavy chain genes are used to modify the constructs made above to produce constructs encoding chimeric bovine-murine antibodies. For example, in one contemplated embodiment, the constant portion of the murine heavy chain gene is replaced with the constant portion of the bovine heavy chain gene to create a chimeric bovine-murine monoclonal antibodies. A suitable bovine heavy chain IgG 1 sequence may be selected from, but is not limited to, the following GenBank Accession Numbers: BD105809; S82409; U32264; U32263; U32262; U32261; U32260; U32259; U32258; U32257; U32256; U32255; U32254; U32253; U32252; U32251; U32250; U32249; U34749; U34748; U32852; U32851; U32850; U36824; U36823; S82407; X62917; X62916; and X16701. Likewise, a suitable bovine heavy chain IgG2 sequence may be selected from, but is not limited to, the following GenBank Accession Numbers: S82409; S82407; Z37506; and X16702. In preferred embodiments, GenBank Accession No. S282409 (SEQ ID NO:1) provides bovine IgG1/IgG2 sequences. (See, I. Kacskovics and J. E. Butler, Mol. Immunol., 33(2):189-195 [1996]). Preferably, the murine IgG2a heavy chain gene will be replaced by the bovine sequence for IgG1 or IgG2a. Thus, modified with bovine IgG1 /IgG2 sequences, the vectors described above are used in subsequent cloning steps.

In preferred embodiments, following sequence analysis of the construct, the constructs are used to create vectors for the transduction of production cell lines (e.g., 293H) and packaging cell lines (e.g., 293 gp). Standard clonal analysis techniques are used to select for clones that produce high levels of the bovine-murine chimeric antibody. Once a top clone has been selected, enough chimeric antibody will be produced from this clone to conduct functionality tests with the derived chimeric monoclonal antibody.

In preferred embodiments, production cell lines that secrete high levels of the monoclonal antibodies are made from the above-mentioned constructs. The retroviral construct containing the chimeric murine-bovine monoclonal antibody genes are used to transduce at least one production cell line (e.g., the 293H production cell line). Upon transduction and expansion, the cell pool is subjected to limited dilution cloning to select for clones that produce high levels of the chimeric monoclonal antibody as determined by standard assay techniques (e.g., ELISA assays). One of the top clones is used to produce chimeric murine-bovine monoclonal antibodies in milligram amounts that are subsequently used in the functionality tests described below.

The present invention further contemplates the production of retrovector packaging cell lines that produce high titers of retrovector containing the gene for the monoclonal antibodies in preparation for making transgenic animals, such as bovines. For example, the retrovector construct containing the chimeric murine-bovine monoclonal antibody genes are used to transduce a packaging cell line (e.g., 293 gp packaging cell line). The transduced packaging cell pool is then subjected to limiting dilution cloning and clones that produce the highest infectious viral titers are used for virus production. After a thorough quality control of the top virus titer producing clone, which ensures that the construct is complete, an appropriate amount of pseudotyped virus are purified and cryopreserved for use in oocyte injections.

III. Production of Pathogen Specific Monoclonal Antibodies in a Multigenic Expression System In certain preferred embodiments, the production of *L. monocytogenes*-specific monoclonal antibody in conducted in the GPEX gene product expression system (Gala Design, Inc., Middleton, Wis.). In an initial step, the transduced production cell pool is subjected to clonal analysis to select the top antibody producing clones. Preferably, the retrovector construct will be used to transform host cells along with the plasmid that encodes the vesicular stomatitis virus glycoprotein (VSV-G) used for pseudotyping the retrovirus. This procedure creates intermediate level viral titer used to infect production cell lines (e.g., 293H and CHO cells among others). The population of transduced cells is then subjected to a clonal selection, based on antibody levels present in the medium supernatant.

In additional embodiments, the selected clones are then expanded and used to produce sufficient quantities of monoclonal *L. monocytogenes*-specific antibodies to perform one or more functionality studies similar to those mentioned above.

The clone with the highest level of antibody secreted into the supernatant is then chosen to produce milligram amounts of recombinant murine monoclonal antibody against *L. monocytogenes*. Additional experiments with the purified monoclonal antibodies, similar to those mentioned above are contemplated. The objective of these experiments is to determine whether the production of the selected high-affinity monoclonal antibody affects the binding capacity when compared to the original hybridoma-derived antibody. Since the present invention contemplates using a mammalian expression system, no changes in affinity of the GPEX produced monoclonal antibody are expected.

IV. Comparison of Murine and Chimeric Murine-Bovine Antibodies

In preferred embodiments, the present invention contemplates additional functionality testing of the purified murine monoclonal antibody as compared to the hybridoma-derived product. For example, in one embodiment, a number of tests are conducted to demonstrate that the 4E8C12 monoclonal is highly specific for *E. coli* strain O157:H7 and strain O26:H11 and no other related strains or species. In some of these embodiments, the assays contemplated for determining the specific bactericidal activity are divided into two phases. First, the bactericidal activity of the monoclonal antibody and fusion proteins are tested in vitro for inactivation of the pathogenic strain (e.g., *E. coli* O157:H7). Second, the monoclonal antibody and fusion proteins are evaluated by adding to formulations in turkey slurries.

In particular, to assess in vitro inactivation, *E. coli* O157: H7 (five food and outbreak isolates) are grown in trypticase soy broth (TSB) until late log phase (~24 h). The cells are harvested by centrifugation, washed in 67 mM sodium phosphate buffer, pH 6.6 (PB), and strains mixed in approximately equal concentrations. The *E. coli* mixture is then added to a level of 105 per ml to PB. The monoclonal conjugates are added starting at concentrations that correspond to the bactericidal concentration of lysozyme and phospholipas A2 alone and down at least 3 logs. The suspensions are incubated at 4° and 10° C. and cell viability determined at 0, 1, 4, 8 and 24 h by direct plating on TSB and MacConkey sorbitol agars. The cell suspensions are examined microscopically for clumping. If clumping is observed, further experimental techniques are used to separate the cells (e.g., addition of surfactants, such as Tween 80, changing pH, and mild sonication). Controls without added monoclonal conjugates are also contemplated for testing. All conditions are tested in triplicate and standard deviations of viability are determined.

In some embodiments, cooked, uncured, and unsmoked turkey breast is obtained from a manufacturer. Slurries of this meat product are prepared as described by Schlyter et al., Int. J. Food Microbiol., 19(4):271-281 (1993) adjusted to the appropriate brine content, and pasteurized to 68° C. Two levels of filter-sterilized monoclonal conjugates, depending on in vitro results, are added to the slurries after pasteurization Flasks are cooled to 4° C. and subsequently inoculated with *E. coli* O157:H7 (five strain mixture of food and outbreak isolates) to yield about a 105 cfu/ml slurry, and dispensed 3 ml per sterile polystyrene tube for incubation at 4 and 10° C. for up to 4 weeks. In preferred embodiments, triplicate samples per variable are assayed weekly for changes in *E. coli* O157:1H7 populations using direct plating on MacConkey sorbitol agar techniques.

In addition to the bactericidal tests, the present invention further contemplates additional experiments to determine whether the chimeric bovine-murine antibodies contemplated are more effective than their murine counterparts in mediating pathogen ingestion by phagocytes. While there is a substantial amount of data available on the efficacy of humanizing therapeutic murine antibodies in order to improve beneficial reactions between immune cells and target cells (for example ADCC, phagocytosis, antigen presentation) in humans, however, the efficacy of a chimeric bovine-murine antibodies in mediating ingestion and killing of a pathogen in cattle has yet to be determined. Accordingly, the present invention provides functional assays of bovine monocyte/macrophage to measure killing/ingestion of *E. coli* O157: 1H7 in the presence of the murine monoclonal antibody, or the chimeric antibody, or no antibody. It is expected that the chimeric bovine-murine antibody of the present invention are superior in mediating phagocytosis compared to murine only versions.

In yet other embodiments, the present invention contemplates the purification of sufficient quantities of retrovectors containing genes for the chimeric monoclonal antibodies to conduct further functional assays and additional tests. In still other embodiments, based upon the results obtained in the above-mentioned assays and tests, further clonal analysis of packaging cell lines that express the chimeric antibody are contemplated. Briefly, a high viral titer producing clone is chosen and expanded. The expanded culture are subsequently induced to produce infective viral particles and viral preparations to enrich viral particles to a titer of approximately 1-5×108 cfu/ml. Such titers have proven effective in producing transgenic animals when used for oocyte injection in transgametic systems.

V. Transgenic Animal Technologies

The methods and compositions used in certain embodiments of the present invention for creating transgenic animals (e.g., bovines and other ungulates) for expression of the biocidal fusion proteins are described in greater detail below.

A. Retroviruses and Retroviral Vectors

Retroviruses (family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses that infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known in the art and this has allowed the adaptation of the retroviral genome to produce retroviral vectors. The production of a recombinant retroviral vector carrying a gene of interest is typically achieved in two stages. First, the gene of interest is inserted into a retroviral vector which contains the sequences necessary for the efficient expression of the gene of interest (including promoter and/or enhancer elements which may be provided by the viral long terminal repeats [LTRs] or by an internal promoter/enhancer and relevant splicing signals), sequences required for the efficient packaging of the viral RNA into infectious virions (e.g., the packaging signal [Psi], the tRNA primer binding site [−PBS], the 3' regulatory sequences required for reverse transcription [+PBS] and the viral LTRs). The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); the resulting virus is said to be replication defective.

Second, following the construction of the recombinant vector, the vector DNA is introduced into a packaging cell line. Packaging cell lines provide viral proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus [VSV]). The transfected packaging cell will then produce viral particles that contain the membrane-associated protein expressed by the transfected packaging cell line; these viral particles, which contain viral genomic RNA derived from one virus encapsidated by the envelope proteins of another virus are said to be pseudotyped virus particles.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) (Miller and Baltimore, Mol. Cell. Biol., 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (Markowitz et al., J. Virol., 62:1120 [1988]).

Despite these advantages, existing retroviral vectors based upon MoMLV are limited by several intrinsic problems: 1) they do not infect non-dividing cells (Miller et al., Mol. Cell. Biol., 10:4239 [1992]), 2) they produce low titers of the recombinant virus (Miller and Rosman, BioTechn., 7: 980 [1989]; and Miller, Nature 357: 455 [1992]) and 3) they infect certain cell types (e.g., human lymphocytes) with low efficiency (Adams et al., Proc. Natl. Acad. Sci. USA 89:8981 [1992]). The low titers associated with MoMLV-based vectors has been attributed, at least in part, to the instability of the virus-encoded envelope protein. Concentration of retrovirus stocks by physical means (e.g., ultracentrifugation and ultrafiltration) leads to a severe loss of infectious virus.

The low titer and inefficient infection of certain cell types by MoMLV-based vectors has been overcome by the use of pseudotyped retroviral vectors which contain the G protein of VSV as the membrane associated protein. Unlike retroviral envelope proteins which bind to a specific cell surface protein receptor to gain entry into a cell, the VSV G protein interacts with a phospholipid component of the plasma membrane (Mastromarino et al., J. Gen. Virol., 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentriftigation without significant loss of infectivity (Burns et al., Proc. Natl. Acad. Sci. USA,90:8033 [1993]).

The VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV.

The present invention is not limited to the use of the VSV G protein when a viral G protein is employed as the heterologous membrane-associated protein within a viral particle. The G proteins of viruses in the Vesiculovirus genera other than VSV, such as the Piry and Chandipura viruses, that are highly homologous to the VSV G protein and, like the VSV G protein, contain covalently linked palmitic acid (Brun et al., Intervirol., 38:274 [1995]; and Masters et al., Virol., 171:285 [1990]). Thus, the G protein of the Piry and Chandipura viruses can be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol., 69:1444 [1995]). Viral particles may be pseudotyped using either the Piry, Chandipura or Mokola G protein as described in the art with the exception that a plasmid containing sequences encoding either the Piry, Chandipura or Mokola G protein under the transcriptional control of a suitable promoter element (e.g., the CMV intermediate-early promoter; numerous expression vectors containing the CMV IE promoter are available, such as the pcDNA3.1 vectors [Invitrogen]) is used in place of pHCMV-G. Sequences encoding other G proteins derived from other members of the Rhabdoviridae family may be used; sequences encoding numerous rhabdoviral G proteins are available from the GenBank database.

B. Integration of Retroviral DNA

The majority of retroviruses can transfer or integrate a double-stranded linear form of the virus (the provirus) into the genome of the recipient cell only if the recipient cell is cycling (i.e., dividing) at the time of infection. Retroviruses that have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J., 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

C. Introduction of Retroviral Vectors into Gametes Before the Last Meiotic Division The nuclear envelope of a cell breaks down during meiosis as well as during mitosis. Meiosis occurs only during the final stages of gametogenesis. The methods of the present invention exploit the breakdown of the nuclear envelope during meiosis to permit the integration of recombinant retroviral DNA and permit for the first time the use of unfertilized oocytes (i.e., pre-fertilization and pre-maturation oocytes) as the recipient cell for retroviral gene transfer for the production of transgenic animals. Because infection of unfertilized oocytes permits the integration of the recombinant provirus prior to the division of the one cell embryo, all cells in the embryo will contain the proviral sequences.

Oocytes which have not undergone the final stages of gametogenesis are infected with the retroviral vector. The injected oocytes are then permitted to complete maturation with the accompanying meiotic divisions. The breakdown of the nuclear envelope during meiosis permits the integration of the proviral form of the retrovirus vector into the genome of the oocyte. When pre-maturation oocytes are used, the injected oocytes are then cultured in vitro under conditions that permit maturation of the oocyte prior to fertilization in vitro. Conditions for the maturation of oocytes from a number of mammalian species (e.g., bovine, ovine, porcine, murine, caprine) are well known to the art. In general, the base medium used herein for the in vitro maturation of bovine oocytes, TC-M199 medium, may be used for the in vitro maturation of other mammalian oocytes. TC-M199 medium is supplemented with hormones (e.g., luteinizing hormone and estradiol) from the appropriate mammalian species. The amount of time a pre-maturation oocyte must be exposed to maturation medium to permit maturation varies between mammalian species as is known to the art. For example, an exposure of about 24 hours is sufficient to permit maturation of bovine oocytes while porcine oocytes require about 44-48 hours.

Oocytes may be matured in vivo and employed in place of oocytes matured in vitro in the practice of the present invention. For example, when porcine oocytes are to be employed in the methods of the present invention, matured pre-fertilization oocytes may be harvested directly from pigs that are induced to superovulate as is known to the art. Briefly, on day 15 or 16 of estrus the female pig(s) is injected with about 1000 units of pregnant mare's serum (PMS; available from Sigma and Calbiochem). Approximately 48 hours later, the pig(s) is injected with about 1000 units of human chorionic gonadotropin) (hCG; Sigma) and 24-48 hours later matured oocytes are collected from oviduct. These in vivo matured pre-fertilization oocytes are then injected with the desired retroviral preparation as described herein. Methods for the superovulation and collection of in vivo matured (i.e., oocytes at the metaphase 2 stage) oocytes are known for a variety of mammals (e.g., for superovulation of mice, see Hogan et al., supra at pp. 130-133 [1994]; for superovulation of pigs and in vitro fertilization of pig oocytes see Cheng, Doctoral Dissertation, Cambridge University, Cambridge, United Kingdom [1995]).

Retroviral vectors capable of infecting the desired species of non-human animal, which can be grown and concentrated to very high titers (e.g., $ 1\times10^8$ cfu/ml) are preferentially employed. The use of high titer virus stocks allows the introduction of a defined number of viral particles into the perivitelline space of each injected oocyte. The perivitelline space of most mammalian oocytes can accommodate about 10 picoliters of injected fluid (those in the art know that the volume that can be injected into the perivitelline space of a mammalian oocyte or zygote varies somewhat between species as the volume of an oocyte is smaller than that of a zygote and thus, oocytes can accommodate somewhat less than can zygotes).

The vector used may contain one or more genes encoding a protein of interest; alternatively, the vector may contain sequences that produce anti-sense RNA sequences or ribozymes. The infectious virus is microinjected into the perivitelline space of oocytes (including pre-maturation oocytes) or one cell stage zygotes. Microinjection into the perivitelline space is much less invasive than the microinjection of nucleic acid into the pronucleus of an embryo. Pronuclear injection requires the mechanical puncture of the plasma membrane of the embryo and results in lower embryo viability. In addition, a higher level of operator skill is required to perform pronuclear injection as compared to perivitelline injection. Visualization of the pronucleus is not required when the virus is injected into the perivitelline space (in contrast to injection into the pronucleus); therefore injection into the perivitelline space obviates the difficulties associated with visualization of pronuclei in species such as cattle, sheep and pigs.

The virus stock may be titered and diluted prior to microinjection into the perivitelline space so that the number of proviruses integrated in the resulting transgenic animal is controlled. The use of a viral stock (or dilution thereof) having a titer of $1\times10^8$ cfu/ml allows the delivery of a single viral particle per oocyte. The use of pre-maturation oocytes or mature fertilized oocytes as the recipient of the virus minimizes the production of animals which are mosaic for the provirus as the virus integrates into the genome of the oocyte prior to the occurrence of cell cleavage.

In order to deliver, on average, a single infectious particle per oocyte, the micropipets used for the injection are calibrated as follows. Small volumes (e.g., about 5-10 pl) of the undiluted high titer viral stock (e.g., a titer of about $1\times10^8$ cfu/ml) are delivered to the wells of a microtiter plate by pulsing the micromanipulator. The titer of virus delivered per a given number of pulses is determined by diluting the viral stock in each well and determining the titer using a suitable cell line (e.g., the 208F cell line) as described in the art. The number of pulses which deliver, on average, a volume of virus stock containing one infectious viral particle (i.e., gives a MOI of 1 when titered on 208F cells) are used for injection of the viral stock into the oocytes.

Prior to microinjection of the titered and diluted (if required) virus stock, the cumulus cell layer is opened to provide access to the perivitelline space. The cumulus cell layer need not be completely removed from the oocyte and indeed for certain species of animals (e.g., cows, sheep, pigs, mice) a portion of the cumulus cell layer must remain in contact with the oocyte to permit proper development and fertilization post-injection. Injection of viral particles into the perivitelline space allows the vector RNA (i.e., the viral genome) to enter the cell through the plasma membrane thereby allowing proper reverse transcription of the viral RNA.

D. Detection of the Retrovirus Following Injection into Oocytes or Embryos

The presence of the retroviral genome in cells (e.g., oocytes or embryos) infected with pseudotyped retrovirus may be detected using a variety of means. The expression of the gene product(s) encoded by the retrovirus may be detected by detection of mRNA corresponding to the vector-encoded gene products using techniques well known to the art (e.g., Northern blot, dot blot, in situ hybridization and RT-PCR analysis). Direct detection of the vector-encoded gene product(s) is employed when the gene product is a protein which either has an enzymatic activity (e.g., α-galactosidase) or when an antibody capable of reacting with the vector-encoded protein is available.

Alternatively, the presence of the integrated viral genome may be detected using Southern blot or PCR analysis. For example, the presence of the LZRNL or LSRNL genomes may be detected following infection of oocytes or embryos using PCR as follows. Genomic DNA is extracted from the infected oocytes or embryos (the DNA may be extracted from the whole embryo or alternatively various tissues of the embryo may be examined) using techniques well known to the art. The LZRNL and LSRNL viruses contain the neo gene and the following primer pair can be used to amplify a 349-bp segment of the neo gene: upstream primer: 5'-GCATTGCAT-CAGCCATGATG-3' (SEQ ID NO: 103) and downstream primer: 5'-GATGGATTGCACGCAGGTTC-3' (SEQ ID NO: 104). The PCR is carried out using well known techniques (e.g., using a GeneAmp kit according to the manufacturer's instructions [Perkin-Elmer]). The DNA present in the reaction is denatured by incubation at 94EC for 3 min followed by 40 cycles of 94EC for 1 min, 60EC for 40 sec and 72EC for 40 sec followed by a final extension at 72EC for 5 min. The PCR products may be analyzed by electrophoresis of 10 to 20% of the total reaction on a 2% agarose gel; the 349-bp product may be visualized by staining of the gel with ethidium bromide and exposure of the stained gel to UV light. If the expected PCR product cannot be detected visually, the DNA can be transferred to a solid support (e.g., a nylon membrane) and hybridized with a $^{32}$P-labeled neo probe.

Southern blot analysis of genomic DNA extracted from infected oocytes and/or the resulting embryos, offspring and tissues derived therefrom is employed when information concerning the integration of the viral DNA into the host genome is desired. To examine the number of integration sites present in the host genome, the extracted genomic DNA is typically digested with a restriction enzyme, which cuts at least once within the vector sequences. If the enzyme chosen cuts twice within the vector sequences, a band of known (i.e., predictable) size is generated in addition to two fragments of novel length which can be detected using appropriate probes.

E. Detection of Foreign Protein Expression in Transgenic Animals

The present invention also provides transgenic animals that are capable of expressing foreign proteins in their milk, urine and blood. The transgene is stable, as and shown to be passed from a transgenic bull to his offspring. In addition, the transgenic animals produced according to the present invention express foreign proteins in their body fluids (e.g., milk, blood, and urine). Thus, the present invention further demonstrates the utility of using the MoMLV LTR as a promoter for driving the constitutive production of foreign proteins in transgenic cattle. It is also contemplated that such a promoter could be used to control expression of proteins that would prevent disease and/or infection in the transgenic animals and their offspring, or be of use in the production of a consistent level of protein expression in a number of different tissues and body fluids.

For example, it is contemplated that the MoMLV LTR of the present invention will find use in driving expression of antibody to pathogenic organisms, thereby preventing infection and/or disease in transgenic animals created using the methods of the present invention. For example, it is contemplated that antibodies directed against organisms such as *E. coli, Salmonella* ssp., *Streptococcus* ssp., *Staphylococcus* spp., *Mycobacterium* spp., produced by transgenic animals will find use preventing mastitis, scours, and other diseases that are common problems in young animals. It is also contemplated that proteins expressed by transgenic animals produced according to the present invention will find use as bacteriostatic, bactericidal, fungistatic, fungicidal, viricidal, and/or anti-parasitic compositions. Thus, it is contemplated that transgenic animals produced according to the present invention will be resistant to various pathogenic organisms. Furthermore, the milk produced by female transgenic animals would contain substantial antibody levels. The present invention contemplates that these antibodies are useful in the protection of other animals (e.g., through passive immunization methods).

VI. Considerations for Combating *Cryptosporidium* and Other Parasites

A. Production of Transgenic Expression System for Monoclonal 3E2 Antibodies Against *C. parvum*

In certain embodiments, the present invention uses an established hybridoma line (as described herein) as a source for the 3E2 genes for insertion into a replication defective retrovector. While the present invention is not limited to any mechanism, it is contemplated that 3E2 has especially potent neutralizing capabilities against sporozoites because it is of the IgM isotype. It is thought that through binding to repetitive epitopes of the CSL antigen the circumsporozoite precipitate (CSP)-like reaction is induced (M. W. Riggs et al., J. Immunol., 143:1340-1345 [1989]) that renders the sporozoite non-infective. IgM antibodies exist in several forms, one, in unstimulated B-lymphocytes they are membrane-bound and, two, upon stimulation of the B-lymphocyte, IgM is secreted as a pentamer joined by the J-chain. J-chain expression plays an important role in inducing the pentamerization process of IgM. In studies done by Niles et al., high expression of the J-chain resulted in a high percentage of pentameric IgM. (M. J. Niles et al., Proc. Natl. Acad. Sci. USA, 92:2884-2888 [1995]). A third possible configuration for IgM was shown to be a hexamer. (A. Cattaneo and M. S. Neuberger, EMBO J., 6:2753-2758; and T. D. Randall et al., Eur. J. Immunol., 20:1971-1979 [1990]). In one embodiment, the present invention specifically provides a cloning strategy that addresses the pentamer and hexamer configurations. In some embodiments, the hexamer configuration of IgM is contemplated to provide better efficacy against *Cryptosporidium* sporozoites than IgG.

In some embodiments, an IgM isotype control (of irrelevant specificity) is constructed in parallel following the cloning strategy described herein. Briefly, the retrovectors are pseudotyped with VSVg to give pantropic infectivity and used to achieve gene transfer to bovine oocytes and to CHO cells (component C). For transgenic expression in mammals (e.g., bovines), as opposed to expression in cell culture, the construct is designed to remove antibiotic-based selection markers (i.e., undesirable in an animal population), and to insert a promoter that links expression closely to lactation thus restricting expression to the mammary cells. In some embodiments, an alphalactalbumin promoter is used for this purpose. To assure high probability of infection and transgene integration into the oocyte genome, very high retrovector titer is needed for injection into the very small perivitelline space. It is contemplated that using pseudotyped VSVG vector envelope stabilizes the vector and increases the ability to concentrate vector sufficiently for injection in picoliter amounts. Preferably, transgenic embryos are produced by injection of unfertilized oocytes, in vitro fertilization, and transfer to recipient animals (e.g., surrogate bovine mothers). After transgenic offspring have been verified as transgenic and grown to 6-8 months, a hormone regimen is used to initiate lactation.

A consideration in using retrovectors is the need to provide assurances that no reversion, recombination, or mutation of replication defective retrovectors to viral competence has occurred. Thus, in preferred embodiments a testing protocol is followed for testing packaging cell lines and transgenic offspring.

In some embodiments, two different IRES elements are used to reduce the likelihood of recombination events that can be triggered by different identical sequences in a vector. The use of the IRES element in between heavy and light chain genes has been tested extensively and proven to yield fully functional antibodies, expressed and secreted into the medium at high levels (up to 100 pg/cell/day in CHO cells in serum free medium).

B. Selection and Testing of Biocidess, and Preparation of Vector for *Cryptosporidium* Neutralizing Monoclonal Antibodies and Fusion Proteins In some additional embodiments, additional antibodies are selected from a large previously reported test panel. (See, X. D. et al., Infect. Immun., 64:5161-5165 [1996]). For example, 1E10 is an IgG1 isotype, that targets the P23 antigen; 3H2 is an IgM, that targets the GP25-200 antigen. Because, in some embodiments, IgG may be preferred for biocide fusion proteins, The present invention also expresses the 4H9 antibody. 4H9 is an IgG that targets GP25-200, but a different epitope than 3H2.1 (D. A. Schaefer et al., Infect. Immun., 68:2608-2616 [2000]). In one embodiment, a 4 different antibody-biocide fusion types (FIG. 2) from each IgG antibody are constructed. These molecules are expressed in the GPEX cell culture system (Gala Design, Middleton, Wis.) and tested for their efficacy against sporozoites in vitro and in vivo. The considerations pertaining to production of tricistronic constructs for IgM, discussed above with respect to 3E2, are also relevant to 3H2.

To select appropriate biocides, the present invention contemplates expanding the preliminary testing of sporozoite neutralization by potential biocides to include additinoal candidates, and comparison of human PLA2 to bee venom PLA2.

In some preferred embodiments, molecular modeling is used to guide the structural assembly of the fusion molecules. The relative geometry of a monoclonal antibody molecule with a molecule of biocidal activity attached to the C-terminus is similar to that of complement binding to the Fc region of the MAb HC when bound to a pathogen, which results in destruction of the membrane. Thus, the present invention contemplates using the *C. parvum* binding site affinity of the MAb molecule to bring the biocidal activity into close apposition to its substrate by attachment of the biocide to the C-terminus of the monoclonal heavy chain.

Secretory PLA2 is a relatively small molecule (~14 kDa) and is comparable in size to one of the CH1 or CH2 domains of an antibody molecule. As an alternative, an N-terminal extension linker on the PLA2 portion of the molecule is created to move the phospholipase domains a short distance from the MAb molecule. One linker contemplated for use for constructing single chain monoclonal-cytokine fusion proteins is a -(Gly4-Ser)3-extension (~16-20 angstrom extension). (See e.g., C. R. Robinson and R. T. Sauer, Proc. Natl. Acad. Sci. USA, 95:5929-5934 [1998]). This is a relatively neutral sequence that is flexible and does not have a strong structure-forming propensity. In another exemplary embodiment, the present invention inserts a proline into the middle of the extension arm to provide a "kink", with freedom to rotate in the extension chain and thus allow different geometrical relationships between the biocide and the antibody molecule.

C. Expression of Monoclonal Antibodies and Monoclonal Antibody-Biocide Fusions in Cell Culture and Animal Models In some preferred embodiments, the present invention provides animal based expression systems for producing large quantities of present compositions, while, in other preferred embodiments, the present invention provides high yielding cell lines, prepared. In some embodiments, cell based production is more expensive and on a smaller scale than production in transgenic animals (e.g., bovines), significant quantities of antibodies and fusion products are rapidly obtainable as compared to the proposed transgenic-derived products.

After expression and testing in vitro the present invention, contemplates scale up production using roller bottles to make sufficient recombinant product to test in mice. Then the most promising compounds, based on their efficacy in mice, are tested in an animal model where clinical disease is observed. The neonatal mouse model provides an essential, cost-effective means for the initial in vivo evaluation of product efficacy in reducing intestinal infection levels and is widely accepted for this purpose. However, *C. parvum* infection in neonatal mice does not cause diarrhea or other signs of disease, hence the need for subsequent evaluation in a clinical model for compositions having demonstrated anti-cryptosporidial activity in mice.

In some embodiments, piglets are selected as the clinical model of choice because of their small size, availability in adequate numbers to permit comparative studies and statistical analysis, and development of intestinal lesions resulting in acute watery diarrhea, dehydration, malabsorption, and weight loss when infected with *C. parvum* (C. W. Kim, Cryptosporidiosis in Pigs and Horses. In: J. P. Dubey, C. A. Speer, and R. Fayer eds. Boca Raton, Fla.: CRC Press, pp. 105-111 [1990]). Importantly, as monogastrics, the pathogenesis and control of cryptosporidiosis in piglets is thought to closely model that of human infections and response to treatment. (S. Tzipori, Adv. Parasitol., 40:187-221 [1998]).

Criteria for determining efficacy in piglets include, but are not limited to, clinical signs, weight loss, fecal volume and dry matter, and fecal oocyst quantitation and duration of shedding. Following euthanasia at 10 days post infection, extensive histopathological examination complete the data set.

VII. Transgenic Plant Technologies

In some embodiments, the fusion proteins of the present invention are expressed in transgenic organisms such as transgenic plants having a transgene inserted into its nuclear or plastidic genome. Techniques of plant transformation are known as the art. (See e.g., Wu and Grossman, Methods in Enzymology, Vol. 153, Recombinant DNA Part D, Academic Press [1987], and EP 693554 (incorporated herein by reference in its entirety). Foreign nucleic acids can be introduced into plant cells or protoplasts by several methods. For example, nucleic acid can be mechanically transferred by microinjection directly into plant cells by use of micropipettes. In some embodiments, foreign nucleic acid can also be transferred into plant cells by using polyethylene glycol to form a precipitation complex with the genetic material that is taken up by the cell. (See e.g., Paszkowski et al., J. EMBO, 3:2712-2722 [1984]). In other embodiments, foreign nucleic acid are introduced into plant cells by electroporation. (See e.g., Fromm et al., Proc. Nat. Acad. Sci. USA, 82:5824 [1985]). Briefly, plant protoplasts are electroporated in the presence of plasmids or nucleic acids containing the relevant genetic construct. Electrical impulses of high field strength reversibly permeabilize the plant cell's biomembranes thus allowing the introduction of the plasmids. Electroporated plant protoplasts reform the cell wall, divide, and form a plant callus. Preferably, selection of the transformed plant cells with the transformed gene is accomplished using phenotypic markers.

In certain other embodiments, the cauliflower mosaic virus (CaMV) is used as a vector to introduce foreign nucleic acids into plant cells. (See e.g., Hohn et al., "Molecular Biology of Plant Tumors," Academic Press, New York, pp. 549-560 [1982]; and U.S. Pat. No. 4,407,956 (incorporated by reference herein in its entirety). CaMV viral DNA genome is inserted into a parent bacterial plasmid creating a recombinant DNA molecule which can be propagated in bacteria. The recombinant plasmid can be further modified by introduction of the desired DNA sequence. The modified viral portion of the recombinant plasmid is then excised from the parent bacterial plasmid, and used to inoculate the plant cells or plants.

High velocity ballistic penetration by small particles can be used to introduce foreign nucleic acid into plant cells. Nucleic acid is disposed within the matrix of small beads or particles, or on the surface. (See e.g., Klein et al., Nature, 327:70-73 [1987]). Although typically only a single introduction of a new nucleic acid segment is required, this method also provides for multiple introductions.

A nucleic acid can be introduced into a plant cell by infection of a plant cell, an explant, an ineristem or a seed with Agrobacterium tumefaciens transformed with the nucleic acid. Under appropriate conditions, the transformed plant cells are grown to form shoots, roots, and develop further into plants. The nucleic acids can be introduced into plant cells, for example, by means of the Ti plasmid of Agrobacterium tumefaciens. The Ti plasmid is transmitted to plant cells upon infection by Agrobacterium tumefaciens, and is stably integrated into the plant genome. (See e.g., Horsch et al., Science, 233:496-498 [1984]; and Fraley et al., Proc. Nat. Acad. Sci. USA, 80:4803 [1983]).

Plants from which protoplasts can be isolated and cultured to give whole regenerated plants can be transformed so that whole plants are recovered which contain the transferred foreign gene. All plants that can be produced by regeneration from protoplasts can also be transfected using the process according to the invention (e.g., cultivated plants of the genera *Fragaria, Lotus, Medicago, Onobrychis, Trifolium, Trigonella, Vigna, Citrus, Geranium, Manihot, Daucus, Arabidopsis, Brassica, Raphanus, Sinapis, Atropa, Capsicum, Hyoscyarnus, Lycopersicon, Nicotiana, Solarium, Petunia, Digitalis, Majorana, Ciohorium, Helianthus, Lactuca, Bromus, Asparagus, Antirrhinum, Hererocallis, Nemesia, Pelargoniwn, Panicum, Pennisetum, Ranunculus, Senecio, Salpiglossis, Cucumis, Browaalia, Glycine, Lolium, Zea, Triticum, Sorghum, Datura, Solanum, Beta, Pisum, Phaseolus, Allium, Avena, Hordeum, Oryzae, Setaria, Secale, Sorghum, Triticum, Musa, Cocos, Cydonia, Pyrus, Malus, Phoenix, Elaeis, Rubus, Fragaria, Prunus, Arachis, Saccharum, Coffea, Camellia, Ananas,* or *Vitis*). In general, protoplasts are produced in accordance with conventional methods. (See e.g., U.S. Pat. Nos. 4,743,548; 4,677,066, 5,149,645; and 5,508, 184 all of which are incorporated herein by reference). Plant tissue may be dispersed in an appropriate medium having an appropriate osmotic potential (e.g., 3 to 8 wt. % of a sugar polyol) and one or more polysaccharide hydrolases (e.g., pectinase, cellulase, etc.), and the cell wall degradation allowed to proceed for a sufficient time to provide protoplasts. After filtration the protoplasts may be isolated by centrifugation and may then be resuspended for subsequent treatment or use.

Plant regeneration from cultured protoplasts is described in Evans et al., "Protoplasts Isolation and Culture," Handbook of Plant Cell Cultures 1:124-176 (MacMillan Publishing Co. New York 1983); M. R. Davey, "Recent Developments in the Culture and Regeneration of Plant Protoplasts," Protoplasts (1983)-Lecture Proceedings, pp. 12-29, (Birkhauser, Basal 1983); P. J. Dale, "Protoplast Culture and Plant Regeneration of Cereals and Other Recalcitrant Crops," Protoplasts (1983)-Lecture Proceedings, pp. 31-41, (Birkhauser, Basel 1983); and H. Binding, "Regeneration of Plants," Plant Protoplasts, pp. 21-73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture media can contain various amino acids and hormones, such as auxins and cytokinins. It can also be advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In vegetatively propagated crops, the mature transgenic plants can be propagated by the taking of cuttings or by tissue culture techniques to produce multiple identical plants for trailing, such as testing for production characteristics. Selection of a desirable transgenic plant is made and new varieties are obtained thereby, and propagated vegetatively for commercial sale. In seed propagated crops, the mature transgenic plants can be self crossed to produce a homozygous inbred plant. The inbred plant produces seed containing the gene for the newly introduced foreign gene activity level. These seeds can be grown to produce plants that have the selected phenotype. The inbreds according to this invention can be used to develop new hybrids. In this method, a selected inbred line is crossed with another inbred line to produce the hybrid.

Parts obtained from a transgenic plant, such as flowers, seeds, leaves, branches, fruit, and the like are covered by the invention, provided that these parts include cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

Selection of transgenic plants or plant cells can be based upon a visual assay, such as observing color changes (e.g., a white flower, variable pigment production, and uniform color pattern on flowers or irregular patterns), but can also involve biochemical assays of either enzyme activity or product quantitation. Transgenic plants or plant cells are grown into plants bearing the plant part of interest and the gene activities are monitored, such as by visual appearance (for flavonoid genes) or biochemical assays (Northern blots); Western blots; enzyme assays and flavonoid compound assays, including spectroscopy. (See e.g., Harborne et al., (Eds.) "The Flavonoids, Vols: 1 and 2, Acad. Press 1975). Appropriate plants are selected and further evaluated. Methods for generation of genetically engineered plants are further described in U.S. Pat. Nos. 5,283,184; 5,482,852, and EPO Application EP 693,554 (each of which is herein incorporated by reference in its entirety).

VIII. Pharmaceutical Compositions

The present invention provides novel methods and compositions for treating diseases characterized by pathogenic infection comprising administering subjects (e.g., bovines, humans, and other mammals) a pharmaceutical and/or nutraceutical composition comprising chimeric recombinant antibodies either in food based (e.g., whey protein) carriers, or common pharmaceutical carriers, including any sterile, biocompatible pharmaceutical carrier (e.g., saline, buffered saline, dextrose, water, and the like) to subjects.

In some embodiments, the methods of the present invention comprise administering the compositions of the present invention in suitable pharmaceutical carriers. In some embodiments, these pharmaceutical compositions contain a mixture of at least two types of antibody-biocide compositions co-administered to a subject. In still further embodiments, the pharmaceutical compositions comprise a plurality of antibody-biocide compositions administered to a subject under one or more of the following conditions: at different periodicities, different durations, different concentrations, different administration routes, etc.

In some preferred embodiments, the compositions and methods of the present invention find use in treating diseases or altered physiological states characterized by pathogenic infection. However, the present invention is not limited to ameliorating (e.g., treating) only these types of conditions in a subject. Indeed, various embodiments of the present invention are directed to treating a range of physiological symptoms and disease etiologies in subjects generally characterized by infection with a pathogen (e.g., bacteria, archeae, viruses, mycoplasma, fungi, etc.).

Depending on the condition being treated, these pharmaceutical compositions are formulated and administered systemically or locally. Techniques for formulation and administration are found in the latest edition of "Remington's Pharmaceutical Sciences" (Mack Publishing Co, Easton Pa.). Accordingly, the present invention contemplates administering pharmaceutical compositions in accordance with acceptable pharmaceutical delivery methods and preparation techniques. For example, some compounds of the present invention are administered to a subject intravenously in a pharmaceutically acceptable carrier such as physiological saline. For injection, the pharmaceutical compositions of the invention are formulated in aqueous solutions, preferably in physiologically compatible buffers (e.g., Hanks' solution, Ringer's solution, or physiologically buffered saline). For tissue or cellular administration, penetrants appropriate to the particular barrier to be permeated are preferably used in the formulations. Such penetrants are generally known in the art. Standard methods for intracellular delivery of pharmaceutical agents are used in other embodiments (e.g., delivery via liposomes). Such methods are well known to those skilled in the art.

In some embodiments, present compositions are formulated for parenteral administration, including intravenous, subcutaneous, intramuscular, and intraperitoneal. In some embodiments, these compositions optionally include aqueous solutions (i.e., water-soluble forms). Additionally, suspensions of the active compounds may also be prepared as oily injection suspensions as appropriate. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Therapeutic co-administration of some contemplated compositions is also be accomplished using gene therapy techniques described herein and commonly known in the art.

In other embodiments, the present compositions are formulated using pharmaceutically acceptable carriers and in suitable dosages for oral administration. Such carriers enable the compositions to be formulated as tablets, pills, capsules, dragees, liquids, gels, syrups, slurries, suspensions and the like, for oral or nasal ingestion by a patient to be treated.

Pharmaceutical preparations for oral use can be obtained by combining the active compounds (e.g., chimeric antibody biocide fusion proteins) with a solid excipient, optionally grinding the resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc.; cellulose such as methyl cellulose, hydroxypropylmethyl-cellulose, or sodium carboxymethylcellulose; and gums including arabic and tragacanth; and proteins such as gelatin and collagen. If desired disintegrating or solubilizing agents may be added, such as the cross-linked polyvinyl pyrrolidone, agar, alginic acid or a salt thereof such as sodium alginate.

Ingestible formulations of the present compositions may further include any material approved by the United States Department of Agriculture for inclusion in foodstuffs and substances that are generally recognized as safe (GRAS), such as, food additives, flavorings, colorings, vitamins, minerals, and phytonutrients. The term "phytonutrients" as used herein, refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Compositions of the present invention that can be used orally include push-fit capsules made of gelatin, as well as soft, sealed capsules made of gelatin and a coating such as glycerol or sorbitol. The push-fit capsules can contain the active ingredients mixed with fillers or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

In some embodiments of the present invention, therapeutic agents are administered to a patient alone, or in combination with one or more other drugs or therapies (e.g., antibiotics and antiviral agents etc.) or in pharmaceutical compositions where it is mixed with excipient(s) or other pharmaceutically acceptable carriers. In one embodiment of the present invention, the pharmaceutically acceptable carrier is pharmaceutically inert.

Pharmaceutical compositions suitable for use in the present invention include compositions wherein the active ingredients are contained in an effective amount to achieve the intended purpose. For example, an effective amount of therapeutic compound(s) may be that amount that destroys or disables pathogens as compared to control pathogens.

In addition to the active ingredients, preferred pharmaceutical compositions optionally comprise pharmaceutically acceptable carriers, such as, excipients and auxiliaries that facilitate processing of the active compounds into preparations that can be used pharmaceutically.

In some embodiments, the pharmaceutical compositions used in the methods of the present invention are manufactured according to well-known and standard pharmaceutical manufacturing techniques (e.g., by means of conventional mixing, dissolving, granulating, dragee-making, levigating, emulsifying, encapsulating, entrapping or lyophilizing processes).

Dosing is dependent on severity and responsiveness of the disease state to be treated, with the course of treatment lasting from several days to several months, or until a cure is effected or a diminution of the disease state is achieved. Optimal dosing schedules are calculated from measurements of composition accumulation in the subject's body. The administering physician can easily determine optimum dosages, dosing methodologies and repetition rates. Optimum dosages may vary depending on the relative potency of compositions agents, and can generally be estimated based on the $EC_{50}s$ found to be effective in in vitro and in vivo animal models. Additional factors that may be taken into account, include the severity of the disease state; the age, weight, and gender of the subject; the subject's diet; the time and frequency of administration; composition combination(s); possible subject reaction sensitivities; and the subject's tolerance/response to treatments. In general, dosage is from 0.001 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the therapeutic agent is administered in maintenance doses, ranging from 0.001 μg to 100 g per kg of body weight, once or more daily, weekly, or other period.

For any compound used in the methods of the invention, the therapeutically effective dose can be estimated initially from cell culture assays. Then, preferably, dosage can be formulated in animal models (particularly murine or rat models) to achieve a desirable circulating concentration range that results in increased PKA activity in cells/tissues characterized by undesirable cell migration, angiogenesis, cell migration, cell adhesion, and/or cell survival. A therapeutically effective dose refers to that amount of compound(s) that ameliorate symptoms of the disease state (e.g., pathogenic infection). Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from cell culture assays and additional animal studies can be used in formulating a range of dosage, for example, mammalian use (e.g., humans). The dosage of such compounds lies preferably, however the present invention is not limited to this range, within a range of circulating concentrations that include the $ED_{50}$ with little or no toxicity.

Guidance as to particular dosages and methods of delivery is provided in the literature (See, U.S. Pat. Nos. 4,657,760; 5,206,344; or 5,225,212, all of which are herein incorporated by reference in their entireties). Administration of some agents to a patient's bone marrow may necessitate delivery in a manner different from intravenous injections.

EXAMPLES

The present invention provides the following non-limiting examples to further describe certain contemplated embodiments of the present invention.

Example 1

Effects of PLA2 on Sporozoite Infectivity

This experiment describes the effects of PLA2 on sporozoite infectivity. Briefly, sporozoites were incubated in an isotonic saline solution (37° C., 30 min) with a range of concentrations of PLA2 isolated from honey bee venom (Sigma-Aldrich Corp., St. Louis, Mo., 1.5 U/μg protein). Control sporozoites were identically incubated in buffer containing concentration-matched BSA but no PLA2. Sporozoites were then washed in medium and inoculated onto replicate Caco-2 human intestinal epithelial cell monolayers. 24 h later, infection was quantified in test and control monolayers by immunofluorescence assay as described herein and the mean percent reduction of infection calculated. The results indicate that PLA2 achieved a highly significant reduction of sporozoite infectivity at a concentration as low as 0.014 U/ml (FIG. 3, $P<0.0005$). Percent viability of Caco-2 cells following exposure to PLA2-treated sporozoites (86%) was similar to that of uninoculated control cells (91 %) at 24 hrs, as determined by trypan blue dye exclusion. This finding suggests little if any toxic effect of residual PLA2 on host cells. The data suggests that PLA2 is a viable candidate for antibody fusion. Through fusion of PLA2 to a monoclonal antibody with a high affinity for sporozoites, such as 1E10 or 4H9, lethal concentrations of biocide are deliverable to the sporozoite surface with relatively low amounts of biocide being used.

Example 2

Target Antigens CSL, P23, and GP25-200 are Conserved in both Type 1 and Type 2 *C. Parvum* Isolates Western blotting of type 1 and type 2 *C. parvum* was performed to evaluate expression of the antigens and epitopes defined by the monoclonal antibodies proposed herein. For these studies, human *C. parvum* isolates were obtained from Peruvian patients and genotyped by nested PCR primers designed to amplify a region within the 18S rRNA gene, followed by RFLP analysis of the amplicons to differentiate Type 1 from Type 2 according to G. D. Sturbaum et al., Appl. Environ. Microbiol., 67:2665-2668 [2001]). Two human isolates determined to be of the Type 1 genotype were evaluated by Western blot for recognition by monoclonal antibodies 3E2 (anti-CSL), 1E10 (anti-P23), and 3H2 (anti-GP25-200) using previously described methods. (M. W. Riggs et al., Infect. Immun., 62:1927-1939 [1994]). The Iowa Type 2 isolate (J. Heine et al., J. Infect. Dis., 150:768-775 [1984]) was examined in parallel. Each monoclonal bound to both Type 1 isolates. In addition, the molecular weights and immunoreactivities of the Type 1 antigens recognized by each monoclonal were indistinguishable from those recognized in the Type 2 isolate in blots of antigen resolved by either 2-12% or 4-20% reducing SDS-PAGE. Importantly, these findings suggest conservation of the antigens and epitopes defined by 3E2, 1E10, and 3H2 between Type 1 and Type 2 *C. parvum*, and are consistent with the functional role ascribed to each antigen.

Example 3

Various Genetic Engineering Techniques

The present example describes the isolation of the genes for the heavy, light, and J-chains from the 3E2 murine hybridoma cell line, cloning into the retrovector backbone in two configurations (for cell culture expression and for transgenic production), and clonal analysis of the vector producing packaging lines to identify high titer lines maintaining the fidelity of the protein.

In one embodiment, cells from the 3E2 hybridoma are used to extract total RNA with the purpose of isolating the monoclonal antibody-specific heavy, light and J-chain transcripts. Upon total RNA extraction, the RNA is reverse transcribed to create cDNA using standard molecular biology protocols. The total cDNA is then used as a template to specifically amplify the mouse IgM-heavy and light chains as well as the J chain. Site-directed mutagenesis primers are used to amplify the sequences. The use of these primers adds short sequences of DNA that introduce suitable restriction sites that allow direct cloning of the product into the retrovector backbone.

As mentioned herein, in some embodiments, two retroviral constructs are made containing the hybridoma-derived antibody genes. Preferably, one is a bicistronic construct, aimed at producing hexameric IgM. This construct bears the genes for IgM heavy and light chain and upon expression in a cell, spontaneous hexamer formation of IgM takes place. The elements of this and other contemplated constructs are shown in FIGS. 4A-4D grant. The construct is FIG. 4A provides a bicistronic antibody. The construct provided in FIG. 4B is tricistronic and contains, in addition to the IgM heavy and light chain, the J-chain that for pentamer formation of IgM. (FIG. 4B).

To create the tricistronic vector the following cloning steps are performed. First, the heavy chain (HC) is cloned into the multiple cloning site (MCS) of the disclosed retrovector backbone. Second, the genes for genes for the encephalomyocarditis virus (EMCV) IRES (internal ribosome entry site) element, the signal peptide (SP) and the IgM light chain (LC) are combined. Preferably, the IRES is engineered to optimize the secondary initiation of protein synthesis, thus allowing consistent performance in obtaining equimolar expression of heavy and light chains. The genes for the foot-and-mouth disease virus (FMDV) IRES element, the SP and the J-chain gene are combined in parallel. (See e.g., M. Harries et al., J. Gene Med., 2:243-249 [2000]; and X. Y. Wen et al., Cancer Gene Ther., 8:361-370 [2001]). Third, the IRES-SP-LC element is cloned into the backbone after the HC. Fourth, the third element of the construct, the J-chain, preceded by the second IRES is cloned into the backbone. The present invention contemplates that using two different IRES elements reduces the likelihood of recombination events that are usually triggered by different identical sequences in a vector. The use of the IRES element in between heavy and light chain genes has been extensively tested and has proven to yield fully functional antibodies, expressed and secreted into the medium at exceptionally high levels (up to 100 pg/cell/day in CHO cells in serum free medium).

Once the retroviral constructs are complete, quality control sequencing is used to confirm that all the elements are present. The retrovector construct are then used to transfect production cell lines using the GPEX system (Gala Design, Inc., Middleton, Wis.). Following production in the GPEX system, purified product (either pentameric or hexameric IgM 3E2) is tested using standard in vitro inhibition tests described herein and/or of known technologies.

In some embodiments, for the r3E2 monoclonal antibody to be expressed in the milk of cows, lactation specific promoter based on the bovine alpha-lactalbumin promoter is used (G. T. Bleck and R. D. Bremel, Gene, 126:213-218 [1993]), and the neo-selectable marker is removed from the construct. (See, FIGS. 4C and 4D). In a standard cloning step, the sCMV promoter used in the GPEX system is replaced with the alpha-lactalbumin promoter. Clonal analysis performed on the packaging cell lines to identify the antibody-producing clones that give the highest expression. In additional embodiments, an IgM isotype control (of irrelevant specificity) is constructed in parallel following the same cloning strategy.

Example 4

Production of Vector and Injection into Bovine Oocytes to Make Transgenic Embryos for Transfer to Recipient Animals (Cattle)

After quality assurance, the alphalactalbumin-bearing construct is used to transfect the 293 gp packaging cell line along with the plasmid encoding for the VSVg surface glycoprotein for pseudotyping the viral particles. (See, A. W. Chan et al., Proc. Natl. Acad. Sci. USA, 95:14028-14033 [1998]). 293 gp packaging cells used in this process are derived from working stocks supplied by Gala Designs, Inc. (Middleton, Wis.) for cGMP production. The resulting viral supernatant is used to infect packaging cells at a low virus to cell ratio so as to achieve single insertions of the virus. The packaging cell pool are then subjected to a clonal analysis and supernatants of single clones are monitored for high titer viral particle production. One clone is chosen based on viral titer and quality assurance for use in the TRANSGAMETIC system (Gala Design, Inc., Middleton, Wis.). Bovine oocytes are harvested and grown in culture to metaphase 2 arrest (16 hrs). At this stage, which is prolonged in the bovine oocyte, the nuclear membrane has dispersed, allowing vector to gain access to the nucleus. Pseudotyped vector injected into the perivitelline space infects the oocyte and provirus is integrated into the oocyte's haploid DNA. Upon viral particle injection, the oocytes are fertilized using sexed semen, which allows for almost 100% female calves to be born. The transgenic frequency is expected to be between 25-75%. Preferably, embryos are biopsied and screened by PCR for presence of the transgene prior to transfer into recipients, to optimize the transfer of transgene positive embryos.

In vitro tests are done to confirm that the tricistronic expression of the 3E2 IgM antibody has no influence on specificity and affinity of this antibody. Following positive in vitro tests of the recombinant 3E2 monoclonal antibody and achievement of high numbers of transgenic embryos, the embryos are transferred into surrogate mothers. Accordingly, groups of young mature female cattle (heifers) are hormonally synchronized to receive embryos at seven days post fertilization. Cattle are observed throughout pregnancy and ultrasounds are conducted to confirm pregnancy and sex of the embryo at 70 days. After the 280 day gestation period, calves are delivered by cesarian section (a routine surgery performed under epidural anesthesia in a standing surviving cow) and tested for the transgene.

Example 5

Confirmation of Transgene Presence

Following birth of the offspring they are tested for presence of the transgene and raised to near puberty. Lactation is then hormonally induced to identify the best protein expression and to provide product for evaluation.

At the age of approximately 8 months, lactation is induced in transgenic heifers, using a hormonal regimen, and milk analyzed for expression of the r3E2 product. Product is collected, purified from whey, and quantified for efficacy studies in mice and piglets.

A progestin implant is used to simulate a short pseudopregnancy and then initiate milking in peripubertal (6-8 months old) heifers. Heifers should yield up to 250-1000 ml per day of milk, increasing rapidly to approximate a first lactation heifer yield of 15-20 liters a day. Subsequent fertility is not impaired. Milk product is tested for the presence of murine antibody using established Western blot and ELISA procedures. The animals are milked until enough product is obtained to conduct efficacy testing in mice and the neonatal pig model using assays described herein. For quantification to carry out efficacy testing in pigs, monoclonal antibody is purified after fat removal from milk by continuous flow centrifuge while the milk is at animal body temperature. A skim milk product is used for further processing. In some embodiments, size exclusion chromatography and tangential-flow ultrafiltration allow purification of sufficient amounts. MAbs are recovered from the milk serum with affinity chromatography or size exclusion chromatography with a similar efficiency as from cell culture fluids.

Example 6

Evaluation of Efficacy of Milk Production

In some embodiments, efficacy studies of milk production are preformed in neonatal mouse and piglet models respectively. In vivo efficacy assays for *C. parvum* neutralizing r3E2 are preformed in mice. Studies of the effect of milk expressed 3E2 on the infectivity of *C. parvum* sporozoites in mice are performed as described herein. In vivo efficacy assays for *C. parvum* neutralizing r3E2 are conducted in piglets. These studies are performed following the same protocol as described herein. Three groups of 8 piglets are assigned to treatment (milk derived r3E2), isotype rIgM control, and placebo control groups. Dosages, experimental regimens, and blinded evaluations are conducted as described herein.

Example 7

Founder Animals

Lines of founder animals are identified for propagation to develop production herds. Suitable high expressing transgenic founder animals (e.g., cattle) are identified and superovulated for propagation of a herd of production animals for large scale production of r3E2. Yields of r3E2 in milk are compared between founder animals and the best animal(s) selected for super ovulation and insemination. Embryos are harvested and stored in liquid nitrogen for future herd expansion.

Example 8

Identification of Candidate for Expression as Recombinant Antibody Biocide Fusion Proteins In some embodiments, various biocides are evaluated for potential neutralizing activity against *C. parvum* sporozoites using the in vitro assay described in herein. Candidate biocides include, but are not limited to: PLA2, both from human and bee venom; protease inhibitors such as leupeptin, aprotinin, antipain, amastatin, and soybean trypsin inhibitor; lysozyme; and phosphatidylinositol-specific phospholipase C. The preceding protease inhibitor candidates were selected based on their reported activity against *C. parvum*. (See e.g., J. R. Forney et al., J. Parasitol., 82:638-640 [1996]; J. R. Forney et al., J. Parasitol., 83:771-774 [1997]; and P. C. Okhuysen et al., Antimicrob. Agents Chemother., 40:2781-2784 [1996]).

For this assay, isolated sporozoites are incubated (15 min, 37° C.) with an individual biocide in isotonic buffer over a range of concentrations that would theoretically be achievable at the sporozoite surface by targeted delivery as a MAb-biocide fusion protein. PLA2 concentrations are based in part on preliminary data which showed that <0.02 units/ml was effective in neutralization. In parallel, viability of control sporozoites after incubation with the selected biocide concentrations is determined by fluorescein diacetate assay. (See, M. W. Riggs et al., Infect. Immun., 62:1927-1939 [1994]). Following incubation with biocide, sporozoites are washed, and then inoculated onto individual Caco-2 human intestinal epithelial cell monolayers grown in microscopy grade 96-well plates (10 replicates per treatment). For comparison, control monolayers are inoculated with sporozoites identically incubated with: 1) MEM; 2) murine hybridoma-derived neutralizing MAb 3E2 as a positive control; or 3) non-toxic control proteins such as BSA, each concentration-matched to the biocide being tested. Samples are then processed and evaluated as described herein. The mean numbers of intracellular parasite stages per host cell in test and control cultures is examined for significant differences using ANOVA. Each experiment is performed three times. In parallel experiments, to monitor potential host cell toxicity of residual biocide, control monolayers are inoculated with the final wash medium from biocide incubation tubes to which no sporozoites were added, but which otherwise have been processed identically to test samples. Cell viability in control and sporozoite inoculated monolayers is determined 24 hrs post-inoculation using an acridine orange-ethidium bromide viability assay and epifluorescence microscopy. (See, R. C. Duke and J. J. Cohen, Morphological and biochemical assays of apoptosis. John Wiley & Sons, New York, N.Y., [2002]).

Example 9

Isolation of Genes for Antibody Heavy, Light Chains, and J Chains

In some embodiments, the genes for antibody heavy, light chains, and J chains where applicable, are isolated from the 1E10, 3H2, and 4H9 hybridoma cell lines. The genes are cloned into the GPEX retrovector (Gala Design, Inc., Middleton, Wis.) as standalone antibody constructs for each antibody, and for the IgG1s 1E10 and 4H9, as fusions to a biocide gene. In some embodiments, 4 structurally different antibody-biocide fusion variants are considered for 1E10 and 4H9. At the same time, vectors with a promoter suitable for transgenic expression are prepared.

Figure 5:
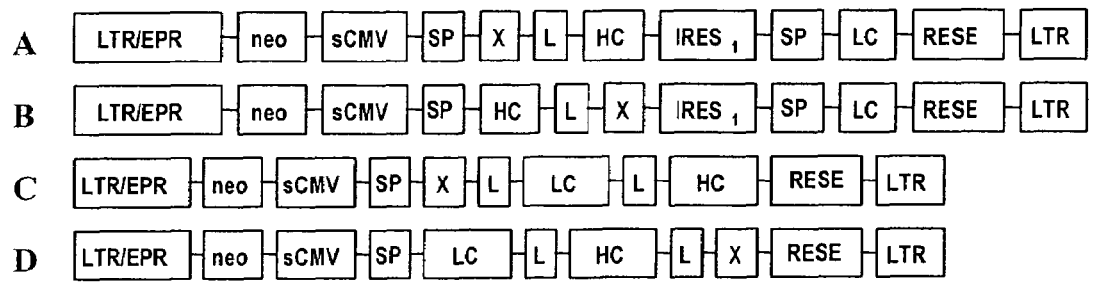
FIGS. 5A-5D show retrovector elements used for mammalian cell culture production of biocide fusion proteins in certain embodiments of the present invention.

The following hybridoma cell lines are used for antibody gene extraction: 3H2, which expresses an IgM against GP25-200; 4H9, which expresses an IgG1 against GP25-200; and IE10, which expresses an IgG1 against P23. An isotype control for IgG is constructed and prepared in parallel using a hybridoma of irrelevant specificity. Total RNA is extracted from cells with the purpose of isolating the monoclonal antibody-specific heavy and light chain genes as described herein. The immunoglobulin genes are be cloned into the GPEX retrovector backbone as bicistronic constructs; in the case of 3H2, the present invention contemplates apply a cloning strategy identical to the one applied for the 3E2 constructs described herein. (See, FIGS. 5A-5D). Standalone recombinant constructs of each antibody are produced. In addition, two IgG isotypes are engineered to contain a biocide attached to either the N-terminus or the C-terminus of the antibody. The cDNA for the biocide found to be most effective in neutralizing C. parvum sporozoites in vitro, and least toxic to host cells is acquired through either the NIH Mammalian Gene Collection (human PLA2) or synthesized (Blue Heron Biotechnology, Seattle). The PLA2, or other biocide, cDNA is expanded through standard amplification in E. coli laboratory strains. Plasmid are extracted and sequenced for quality control purposes. The biocide genes are then cloned into 4 different antibody fusion constructs using glycine-serine (G4S)3-4 linkers. When expressed in the GPEX system, these constructs produce: a full size antibody with a biocide fusion to either the N-terminus (FIG. 5A) or to the C-terminus (FIG. 5B) of the heavy chain; or a single chain antibody with a biocide fusion to the N-terminus of the light chain (FIG. 5C) or to the C-terminus of the heavy chain (FIG. 5D). The antibody-biocide fusions are tested for their efficacy in mediating neutralization and killing of sporozoites in vitro and reducing infection in vitro and in vivo.

Figure 4:
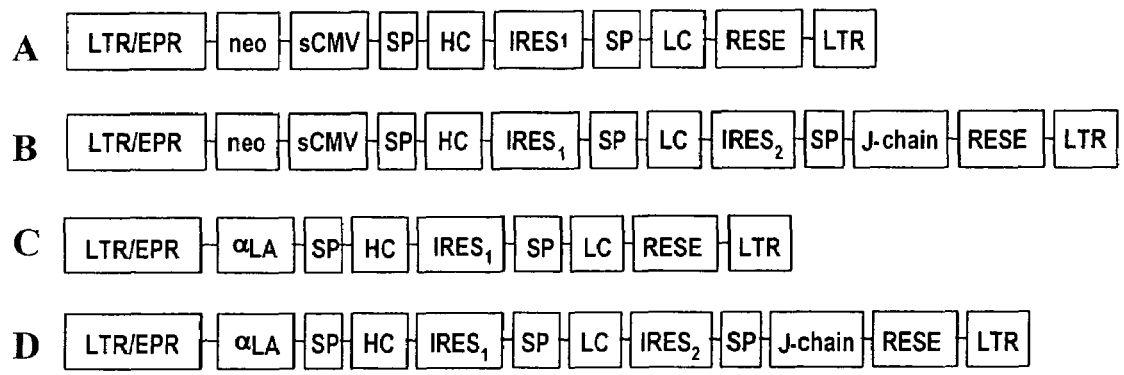
FIG. 4A shows retrovector elements used for mammalian cell culture production of recombinant 3E2 IgM antibody as a hexamer.
FIG. 4B shows retrovector gene construct used for GPEX production of recombinant 3E2 IgM antibody as a pentamer with J-chain.
FIG. 4C shows C a retrovector construct used for transgenic production of recombinant 3E2 IgM antibody as a hexamer.
FIG. 4D, shows a retrovector gene construct used for transgenic production of recombinant 3E2 IgM antibody as a pentamer with J-chain

Constructs are also prepared for the production of transgenic embryo monoclonal antibody to be expressed in the milk of cows, using a lactation specific promoter based on the bovine alpha-lactalbumin promoter (G. T. Bleck and R. D. Bremel, Gene, 126:213-218 [1993]), and the neo-selectable marker is removed from the construct (FIG. 4). In a standard cloning step, the sCMV promoter used in the GPEX system (Gala design, Inc., Middleton, Wis.) will be replaced with the alpha-lactalbumin promoter.

Retrovector constructs are used to transduce host cells and produce pseudotyped replication deficient retrovector. Pool populations of transduced cells are subjected to a clonal selection, based on antibody levels present in the medium supernatant determined by C. parvum ELISA. Clones with the highest level of antibody secreted into the supernatant are chosen to produce milligram amounts of recombinant murine monoclonal antibody and monoclonal antibody-biocide fusions against C. parvum.

Constructs needed for transgenic cattle production are also prepared. Constructs contain lactation specific promoter based on the bovine alpha-lactalbumin promoter (G. T. Bleck and R. D. Bremel, infra), and no neo-selectable marker (FIG. 4). In a standard cloning step, the sCMV promoter used in the GPEX system is replaced with the alpha-lactalbumin promoter.

Example 10

Cloning of Vector Constructs

In some embodiments, the above vector construct, and those for antibody 3E2 are clonally selected and expressed in the GPEX cell culture system (Gala Design, Inc., Middleton, Wis.) to obtain adequate quantities of assembled antibody or antibody-biocide fusion protein for testing in vitro and in vivo.

Briefly, the retrovector constructs prepared above are used to transform host cells along with the plasmid that encodes the vesicular stomatitis virus glycoprotein (VSV-G) used for pseudotyping the retrovirus. This procedure creates intermediate level viral titer that is used to infect production cell lines (CHO cells). CHO cells used in this process are derived from a working stock used to established a cGMP production. The population of transduced cells is subjected to a clonal selection, based on antibody levels present in the medium supernatant. Antibody levels are determined by standard ELISA methods using sporozoite lysate antigen prepared as described in Schaefer et al. (D. A. Schaefer et al., Infect. Immun., 68:2608-2616 [2000]). The clones with the highest level of antibody secreted into the supernatant are chosen to produce milligram amounts of recombinant monoclonal antibody. Using the GPEX cell culture in a roller bottle system, gram scale quantities of rMAbs 3E2, 3H2, 1E10, 4H9, and the rMAb-fusion parasiticides are expressed. Based on a 30 pg/cell/day average, one roller bottle produces approximately 20 mg product per week.

In some embodiments, complete product purification is unnecessary to formulate oral immunotherapies, especially when milk derived. However, in some embodiments, for the purposes of standardization of tests, purification of the monoclonals from tissue culture medium follows protocols established for other monoclonals. Briefly, harvested media is filtered through a 0.45 micron sterile filter to remove cells and the immunoglobulins (IgG1, IgG2, and IgG4) and are captured using a protein A affinity column, or in case of IgM, using HiTrap IgM Purification columns (Amersham Biosciences, Piscataway, N.J.) or for the purification of single chain antibodies Thiophilic Resin columns (BD Biosciences Clontech, Palo Alto, Calif.). After washing, the immunoglobulins are eluted by low pH and the pooled eluate fractions are neutralized to pH 7.5. In some embodiments, a second chromatography step is employed to remove contaminants, host cell DNA and to act as a viral clearance step. This typically utilizes anion exchange chromatography (e.g., Q-Sepharose). The final polishing step utilizes size exclusion chromatography (e.g., Sephadex 200), to separate aggregates from monomers. Antibody are further concentrated or formulated as required.

Example 11

Recombinant Monoclonal Antibodies and Monoclonal Antibody Biocide Fusion Products Efficacy in Neutralizing Sporozoites In vitro In some embodiments, recombinant monoclonal antibodies and monoclonal antibody biocide fusion products expressed herein are tested for their efficacy in neutralizing sporozoites in vitro.

Prior to testing in neutralization assays, the monoclonals are evaluated for retention of sporozoite and merozoite reactivity by IFA, and for antigen specificity by Western immunoblot. (See e.g., M. W. Riggs et al., Infect. Immun., 62:1927-1939 [1994]; M. W. Riggs et al., J. Immunol., 158:1787-1795 [1997]).

In vitro Neutralization Assay for C. parvum

To quantify specific neutralizing activity of each of the four MABs and the fusion biocides against the infective sporozoite stage, an in vitro neutralization assay is used. (See, R. C.

Langer et al., Infect. Immun., 67:5282-5291 [1999]). The antibody-biocide fusions based on the r1E10 and r4H9 antibodies in the four configurations depicted in FIG. 5, and full size versions of r1E10, r4H9, and r3H2 are each tested individually. For this assay, isolated sporozoites are incubated with the selected MAB (10 µg/ml final concentration), then inoculated onto individual Caco-2 human intestinal epithelial cell monolayers (ATCC HTB37) (M. Pinto et al., Biol. Cell, 47:323-330 [2002]). Prior to inoculation, monolayers of Caco-2 cells are grown to ~90% confluency in microscopy grade 96-well tissue culture plates. For comparison, control monolayers are inoculated with sporozoites which have been identically incubated with: 1) tissue culture medium (MEM); 2) murine hybridoma-derived neutralizing monoclonal; or 3) isotype- and concentration-matched recombinant control MAb of irrelevant specificity. Ten replicates are performed for each treatment. After incubation, inoculation medium is aspirated from monolayers and replaced with MEM. At 24 hrs post-inoculation, monolayers are washed, fixed, blocked, and processed for automated immunofluorescence assay (IFA) using MAb 4B10 and AlexaFluor488 affinity-purified goat anti-mouse IgM to detect intracellular stages. MAb 4B10, prepared against *C. parvum* as previously described (M. W. Riggs et al., J. Immunol. 158:1787-1795 [1997]), recognizes all parasite stages in Caco-2 cells through 72 hrs post-inoculation. (R. C. Langer and M. W. Riggs, Infect. Immun., 67:5282-5291 [1999]). Intestinal epithelial cell nuclei are counterstained with 300 nM 4,6-diamidino-2-phenylindole. Using an Olympus-IMT2 inverted microscope equipped for automated digital image capture, 50 standardized visual fields per well are read and stored on the program computer. Intracellular parasite stages and epithelial cell nuclei are then quantified using Compix SimplePCI software (Compix, Inc., Cranberry Township, Pa.). Mean numbers of intracellular parasite stages per host cell in test and control cultures are examined for significant differences using ANOVA. Each experiment is performed three times. BSL-2 precautions are observed to prevent accidental infection of project personnel with *C. parvum.*

*Cryptosporidium parvum* Propagation for Use in the Proposed Studies

The Iowa *C. parvum* isolate (J. Heine et al., J. Infect. Dis., 150:768-775 [1984]) (genotype 2, bovine origin) has been maintained since 1988 by propagation in newborn *Cryptosporidium*-free calves (M. W. Riggs et al., J. Immunol., 143:1340-1345 [1989]; and M. W. Riggs and L. E. Perryman, Infect. Immun., 55:2081-2087 [1987]). This well-characterized isolate is infectious for humans and animal models, including neonatal mice and pigs. (See e.g., J. Heine et al., J. Infect. Dis., 150:768-775 [1984]; R. C. Langer and M. W. Riggs, Infect. Immun., 67:5282-5291 [1999]; H. W. Moon and W. J. Bemrick, Vet. Pathol., 18:248-255 [1981]; and S. Tzipori H. and Ward, Microbes. Infect., 4:1047 [2002]). Parasites are obtained by propagation in newborn calves as previously described. (M. W. Riggs and L. E. Perryman, supra). Oocysts are isolated from the feces of experimentally infected calves as previously described, and stored in 2.5% $KCr_2O_7$ (4° C.) (M. J. Arrowood K. and Donaldson et al., J. Eukaryot. Microbiol., 43:895 [1996]; and M. W. Riggs and L. E. Perryman, supra). To obtain isolated sporozoites, oocysts are hypochlorite-treated prior to excystation, then passed through a sterile polycarbonate filter. For mouse and piglet experiments, oocysts are used within 30 days of isolation and disinfected with 1% peracetic acid prior to administration.

Example 12

In vivo Neutralizing Activity Assays

Each of the monoclonal antibody-biocide fusions based on the r1E10 and r4H9 antibodies and monoclonal antibodies r3E2, r1E10, r4H9, and r3H2 determined to have significant in vitro sporozoite neutralizing activity, is individually tested to quantify in vivo efficacy against infection. The neonatal mouse model is used. (See, M. W. Riggs M W and L. E. Perryman, Infect. Immun., 55:2081-2087 [1987]; and D. A. Schaefer et al., Infect. Immun., 68:2608-2616 [2000]). Groups of 15 six-day-old specific pathogen free ICR mice (Harlan Sprague Dawley) are administered $5\times10^4$ oocysts (50×mouse $ID_{50}$) by gastric intubation. After 48 hrs, culture-derived r3E2 (4 mg MAb/ml, 75 μl) are given by intubation. Every 12 hrs thereafter, mice are administered additional r3E2 (4 mg MAb/ml, 100 μl), for a total of eight treatments. Cimetidine (10 mg/kg) are included with all treatments. For comparison, groups of 15 six-day-old control mice are infected and treated identically with: 1) murine hybridoma-derived neutralizing 3E2, or 2) isotype- and concentration-matched recombinant control MAb of irrelevant specificity. After euthanasia at 140-142 hrs post-inoculation, the jejunum, ileum, cecum, and colon are collected from each mouse and processed for histopathology. Sections are coded and examined by the same investigator, without knowledge of treatment group, for *C. parvum* stages in mucosal epithelium. Scores are assigned to longitudinal sections representing the entire length of: i) terminal jejunum; ii) ileum; iii) cecum; and (iv) colon, then summed to an infection score for each mouse. (See, M. W. Riggs M W and L. E. Perryman, Infect. Immun., 55:2081-2087 [1987]; and D. A. Schaefer et al., Infect. Immun., 68:2608-2616 [2000]). Each experiment is performed twice. Mean infection scores within each experiment are analyzed by Student's one-tailed t test. Mean infection scores between experiments are analyzed by ANOVA. Additionally, all intestinal sections and sections of stomach, liver, and kidney from mice treated with antibody-biocide fusions are examined by an ACVP Board-Certified Veterinary Pathologist to determine if any lesions suggestive of biocide-host toxicity are present.

Example 13

In vivo Efficacy Assays of rMAbs and rMAb-Fusion Parasiticides in a Neonatal Piglet Model This example provides in vivo efficacy assays for *C. parvum* neutralizing rMAb. Newborn male piglets for the proposed studies are obtained by project personnel at the time of parturition from sows in which the perineum has been thoroughly cleaned using standard methods equivalent to presurgical preparation. Piglets, collected as born and colostrum-deprived, are immediately placed in disinfected isolation crates for transport to BSL-2 isolation facilities. Precautions are taken to prevent animal exposure to an exogenous source of *C. parvum* and other potential diarrheal agents. (See e.g., L. E. Perryman et al., Mol. Biochem. Parasitol., 80:137-147 [1996]; L. E. Perryman et al., Vaccine, 17:2142-2149 [1999]; and M. W. Riggs and L. E. Perryman, Infect. Immun., 55:2081-2087 [1987]). Following arrival at BSL-2 isolation facilities, piglets are assigned to either treatment (8 piglets) or control groups (8 piglets) by blind code. Group assignments and coding are made by an independent third party not be involved in conducting the experiments, data collection, or interpretation of results. All personnel involved with the experiments have no knowledge of piglet group assignments. Codes are revealed only at completion of the study. Testing of rMAbs and rMAb-biocide fusion proteins, individually and in combination to be selected, proceeds as follows.

Testing of Individual rMAbs

To allow accurate comparisons between activities of the six rMAb constructs being evaluated, the concentration of each is standardized on an equimolar basis. Using the experimental design for rMAb 3E2 as an example, each construct is evaluated, individually, as follows. One group of 8 piglets is administered $10^7$ oocysts by gastric intubation at 24 hrs of age. Forty-eight hours later, each piglet receives 250 mg culture-derived rMAb 3E2 by intubation. At 12 hrs and every 12 hrs thereafter, each piglet is administered 50 mg additional rMAb 3E2 for a total of 10 treatments (750 mg MAb r3E2 total/piglet). Omeprazole (PRILOSEC, Astra-Merck) [1 mg/kg] is administered 6-8 hrs prior to each rMAb treatment to block production of gastric acid according to a regimen previously shown to elevate gastric pH in pigs to ~7 (D. L. Foss and M. P. Murtaugh, Vaccine, 17:788-801 [1999]). As an additional precaution against gastric degradation, rMAb is formulated in $NaHCO_3$ buffer prior to administration. For comparison, a group of 8 control piglets is identically infected with $10^7$ oocysts and administered recombinant isotype control MAb construct according to the same treatment regimen as the principals. Piglets are confined, individually, in elevated metabolic isolation cages equipped with fecal collection pans, and maintained on ESBILAC (PetAg, Inc., Hampshire, Ill.) for the duration of the experiment. To prevent urine from contaminating feces for subsequent analyses, a diversion device is attached and sealed around the prepucial orifice of each piglet to divert urine into a drainage outlet. Piglets are examined twice daily by a veterinarian, without knowledge of treatment group, and assigned numerical scores based on clinical assessment for symptoms of depression, anorexia, and dehydration. Piglet weights at the time of infection and at the end of the experiment are also recorded. The total volume of feces excreted and percent dry matter for successive 24 hrs fecal collections is determined to provide an objective, quantitative index of diarrhea for each piglet. Fecal samples are examined for oocysts prior to challenge and daily thereafter by IFA using oocyst-specific MAb 4D3 to determine pre-patent and patent periods as previously described. (See, M. W. Riggs et al., Antimicrob. Agents Chemother., 46:275-282 [2002]). Total oocyst counts (number oocysts per ml of feces× total ml feces) for each piglet is determined from samples of well-mixed feces collected over successive 12 hrs periods (M. W. Riggs et al., supra). Feces from each piglet is examined for possible bacterial and viral enteropathogens by standard methods. Piglets are euthanized 10 days post-infection, or before if clinically indicated. Sections of duodenum, jejunum, ileum, cecum, and colon from identically sampled sites in each piglet are collected for histopathology. Sections are coded and examined histologically without knowledge of treatment group by an ACVP board-cerified veterinary pathologist. Villus length to crypt depth ratios and the density of organisms per unit length of mucosa is determined as previously described (See, M. W. Riggs et al., Infect. Immun., 62:1927-1939 [1994]; M. W. Riggs. and L. E. Perryman, Infect. Immun., 55:2081-2087 [1987]). Infection scores of 0, 1, 2 or 3 (0, no infection; 1, <33% of mucosa infected; 2, 33 to 66% of mucosa infected; and 3, >66% of mucosa infected) are assigned to longitudinal sections from the (i) terminal jejunum, (ii) ileum, (iii) cecum, and (iv) proximal colon, then summed to obtain an infection score (0 to 12) for each piglet. (M. W. Riggs. and L. E. Perryman, supra). Additionally, all intestinal sections, and sections of stomach, liver, and kidney from piglets treated with rMAb-biocide constructs are examined by an ACVP Board-Certified Veterinary Pathologist to determine if any lesions suggestive of biocide-host toxicity are present. Clinical, parasitologic, and histologic data is analyzed statistically by ANOVA using the General Linear Models Program of SAS.

Testing of Combined rMAbs

Following evaluation of the individual rMAbs above, the necessary data is available to decide which rMAbs are the best candidates for testing in combination for additive efficacy. Based on previous findings in mice, an optimal combination comprises up to three MAbs, one against each of the three target antigens (CSL, P23, GP25-200) (L. E. Perryman et al., Mol. Biochem. Parasitol., 80:137-147 [1996]). Because the neutralizing activity of anti-CSL MAb 3E2 is profoundly greater than that of all other Mabs against *C. parvum*, in some embodiments, this MAb is an important component in the selected combination. Either rMAb 1E10 or rMAb 1E10-biocide fusion, whichever demonstrates greater efficacy in the above experiments, is included in the combination to target P23. In other embodiments, to target GP25-200, rMAb 3H2, rMAb 4H9, or rMAb 4H9-biocide fusion, whichever demonstrates the greatest efficacy in the above experiments, is included. Thus, in one embodiment, the combination to be evaluated contains rMAbs 3E2+1E10 (standalone or biocide fusion)+3H2 or 4H9 (standalone or biocide fusion).

Previous studies on MAb combinations show that hybridoma-derived MAbs 3E2, 1E10, 3H2, and 4H9 recognize distinct epitopes and do not inhibit binding of each other to *C. parvum*. Nevertheless, it is useful to repeat binding inhibition experiments with the recombinant candidates selected for combination testing to confirm that they do not inhibit binding of each other due to steric hindrance or other influences introduced by recombinant expression. In brief, this is evaluated by ELISA using biotin-labeled (Sulfo-NHS-biotin, Pierce) and unlabeled rMAb candidates as previously described. (See, L. E. Perryman et al., supra). Immulon-4 96-well ELISA plates are coated with solubilized sporozoite antigen, washed, and blocked. Plates are incubated with an individual unlabeled rMAb, then biotinylated competitor rMAb, washed, and developed with peroxidase-labeled Streptavidin and substrate. Mean ODs of replicate wells for each treatment and control group are analyzed for significant differences.

After determining that the three rMAbs selected for combination testing in piglets do not significantly inhibit binding of each other, they are combined and the concentration of each standardized on an equimolar basis to match that previously evaluated individually. Efficacy testing of the combined rMAbs in piglets then proceeds as described for individual rMAbs above. In brief, one group of 8 piglets are infected with $10^7$ oocysts at 24 hrs of age and receive the combined rMAbs in NaHCO3 buffer 48 hrs later by intubation. At 12 hrs and every 12 hras thereafter, piglets receive additional combined rMAbs for a total of 10 treatments. For comparison, a group of 8 control piglets are identically infected and administered an appropriate isotype control rMAb combination according to the same treatment regimen. Clinical assessment scores, piglet weights, total volume of feces excreted and percent dry matter for successive 24 hr collections, pre-patent and patent periods, and total oocyst counts are determined as above. Ten days post-infection, sections of duodenum, jejunum, ileum, cecum, and colon from each piglet are collected, and examined histologically to assess lesions and assign infection scores. Tissues are also examined to determine if any lesions suggestive of biocide-host toxicity are present. Clinical, parasitologic, and histologic data is analyzed statistically as described above. Data from testing of the individual rMAbs is compared with data from testing of the rMAb combination by one-way ANOVA stratified by treatment group.

Example 14

Targeted Biocides Using Innate Receptor Recognition

This Example describes the construction and analysis of fusion proteins of an innate receptor and a biocide.

A. Genetic Engineering of sCD14, LBP, SP-D and MBL into Retrovirus Backbone for Secretion All the innate receptor molecules were previously cloned and produced in various cell lines as recombinant molecules. The gene for the human CD14 receptor is obtained from total RNA extracted from human PBMCs. Following reverse transcription of the RNA into cDNA, the specific gene for CD14 is cloned by PCR. Primers are designed to amplify the sequence starting with the signal peptide sequence down to the first codon of the GPI anchor. The GPI anchor is excluded to facilitate secretion. The GPI anchor sequence is replaced by a portion of the human immunoglobulin Fc region. Adding Ig domains to proteins does not interfere with proper folding; an added Fc portion can contribute to the stability of a fusion protein and extend its half-life (e.g., Chang et al., Surgery 2002; 132:149-56). The hinge region, CH2 and CH3 domains of human immunoglobulin are already part of a construct library and are transferred to the CD14 receptor construct. Constructs that contain the Fc portion with a biocide already connected are available from prior work.

LPS binding protein (LBP; accession number NM 004139) naturally occurs as a secreted protein. The amino acid sequence of the secreted protein is known (Schumann et al., Science 1990; 249:1429-31) and the secreted form has been produced as a recombinant protein (Han et al., J Biol Chem 1994; 269:8172-5; Theofan et al., J Immunol 1994; 152: 3623-9). The gene for LBP is cloned from the mammalian gene collection construct into the retroviral construct. As LBP is a secreted protein, it is not necessary to attach an immunoglobulin Fc portion to stabilize it. The linker-biocide portion is attached directly to the C-terminus of LBP.

SP-D and MBL are from the defense collectin family. These molecules form multimers, increasing their overall avidity to the pathogen surface. Surfactant protein D, SP-D has a glomerular structure at its c-terminal end. This structure is thought to interact with LPS either in solution or as part of a pathogen surface. If the linker-biocide portion is added to the c-terminal end it will most likely be very close to the binding site. An N-terminally attached biocide version of the fusion protein is also produced. SP-D can obtain a cross-like tetrameric conformation. Based on electron microscopy images (Holmskov et al., Annu Rev Immunol 2003; 21:547-78) bound SP-D adopts a fairly two-dimensional structure when bound to its specific surface, bringing the N-termini close to the surface as well. An N-terminally attached biocide is thus accessible enough to destroy a bacterial membrane.

The mannan-binding lectin (MBL) is also a collectin, forming multimeric complexes to achieve a highly efficient binding to microorganism surfaces. The gene for MBL is obtained from the human gene collection, accession number 67483. Like the other collectins MBL is a soluble secreted protein therefore not requiring modifications to make it soluble. The gene is used in its native confirmation and the biocide is added via the linker. The same cloning strategy as that described above for SP-D is used.

B. Expression of riR in vitro—Test Binding to Bacterial Components

The retroviral constructs containing the genes for the innate receptor (or the complete construct containing the Fc-portion plus biocide) are co-transfected with the VSV-G envelope plasmid into the packaging cell line and infectious retroviral particles are produced by transient expression. Packaging cells are grown to exponential phase and then exposed to a calcium chloride solution containing a mixture of the VSV-G encoding plasmid and the retroviral construct containing the immunoglobulin genes. Cells are then grown for 16-24 hours until pseudotyped retrovector is harvested from the supernatant over a period of several days. The titers resulting are typically in the range of $10^5$-$10^6$ infectious units per ml culture media. Media is concentrated to be used at high multiplicity of infection on the target production cell line (CHO or 293 cells). Once these production cells have been exposed to high titer retrovirus (transduction), they start to express product (monoclonal antibody or others) typically in the range of 10-25 µg/ml for well-expressed monoclonal antibody molecules in standard plastic tissue culture vessels. The pool population of transduced production cells are subjected to clonal analysis to obtain high-level producing clones.

The recombinant innate receptor molecules (riR) are tested for their interaction with target cells (bacteria), first by enzyme linked immunosorbent assay (ELISA). For this assay, the cell product is first quantified. The natural antigen (e.g., whole *E. coli* cells) is used as a capture agent to monitor specificity. A similar assay has been established to monitor *Listeria* surface antigens. Briefly, antigenic fractions or whole bacteria are used to coat 96-well plates. After washing, samples containing riR are incubated at serial dilutions with the antigen. Secondary conjugates are used to quantify binding. Flow cytometry analysis allows the measurement of the number of riR molecules interacting with whole microorganism cells. Assays are designed to compare all the different recombinant innate receptor candidates simultaneously against one or multiple different targets (e.g. different *E. coli* isolates). These assays identify which candidates (clonal lines) are suitable for the cloning procedures described below.

C. Reengineer riR Construct to Contain Biocide Fusion Portion

Figure 6:
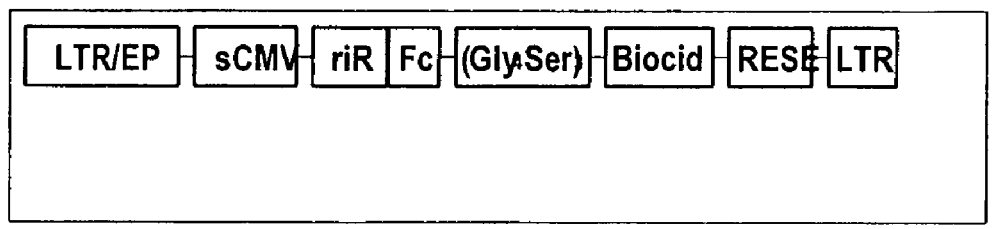
FIG. 6 shows the components of constructs of some embodiments of the present invention featuring a $(Gly_4Ser)_3$ linker.
Figure 7:
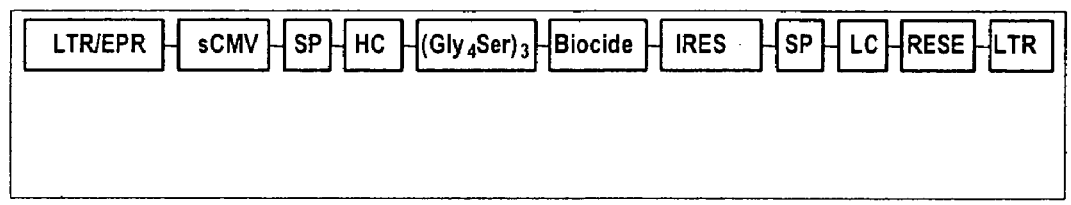
FIG. 7 shows the components of constructs of some embodiments of the present invention that contain an immunoglobulin and a biocide.

Upon determining which of the riR retain good binding capabilities when expressed in mammalian tissue culture, the corresponding genetic constructs are modified to contain the gene for one of the two biocides. Biocides are attached to the riRs at either the N-terminus or at the C-terminus of the riR. The CD14 riR is made with a C-terminal Fc-portion that helps stabilize it. Therefore CD14 is made as a C-terminal biocide only. The other candidates LBP, MBL and SP-D are made as both N-terminal and C-terminal fusions. FIG. 6 shows the components of these constructs featuring a $(Gly_4Ser)_3$ linker which has been used widely. The design of the linker is optimized for functionality of the fusion protein. In some embodiments, the linker is modified as described (George and Heringa, Protein Eng 2002; 15:871-9). Alternatively, the linker is designed with a symmetric sequence of $(Gly_4Ser)_2$-P-P-$(Gly_4Ser)_2$ placing the most favored amino acid pair (a structure breaking Pro-Pro) in the middle of the non-helical linkers. Phospholipase and lysozyme constructs are expressed in cell culture to use as controls.

D. Expression of riR-Biocide Fusions and Binding Tests

The constructs for the riR-biocide fusions are introduced into a mammalian tissue culture system as described above. Upon production of milligram amounts of riR-biocide fusions, binding tests including ELISA and flow cytometry are done. In addition precise affinity measurements are undertaken using surface plasmon resonace (SPR) on a Biacore 2000 machine. This allows for the determination of which riR-biocidebinds best to its target, and also if the linker and fusion elements change the original affinity. Multiple bacterial surface-binding innate immunity receptors are expressed in mammalian tissue culture. In addition, multiple riR-biocide fusion proteins are assembled.

Example 15

Targeted Biocides using Antibody Targeting PAMPs

This Example describes the construction and analysis of constructs comprising monoclonal antibodies and bicides.

A. Antigens for Immunization

Antigens that are not specific to one bacterial isolate but rather common to a broad group are identified (e.g., all Gram negatives or all Gram positives, or all of a major family), in order to obtain a broadly reactive monoclonal antibody. Such targets include structural components such as lipopolysaccharides, peptidoglycans, porins that are common in structure and function among the classes of bacteria (Feng et al., J Gen Microbiol 1990; 136 (Pt 2):337-42; Klebba et al., J Biol Chem 1990; 265:6800-10; Peters et al., Infect Immun 1985; 50:459-66). Preferred targets are genetically defined and can either be purified directly or over-expressed in an *E.coli* expression system. Both of these methods can be used to immunize mice (Feng et al., J Gen Microbiol 1990; 136 ( Pt 2):337-42; He et al., Appl Environ Microbiol 1996; 62:3325-32). For dominant structural components minimal purification is needed to arrive at an antigen preparation that has a strong probability of providing cross reactive antibodies. In some embodiments, *E. coli* O157:H7 and *L. monocytogenes* are utilized as PAMP “donors”.

B. Immunize Mice to Produce Monoclonal Broad Spectrum Antibody

An array of monoclonal antibodies is prepared by Neoclone (Madison, Wis.). The monoclonal antibodies are used to screen for reactivity with an array of target organisms.

C. Antibody Binding Tests Against Wide Variety of Microorganisms, Selection of Best Candidates Monoclonal antibodies are obtained as ascitic fluid containing high levels of monoclonal antibody plus the corresponding immortalized B-cells. The antibody contained in the ascitic fluid is used to perform specificity and affinity tests on various targets. Multiple strains of pathogenic *E. coli, Salmonella, Listeria*, and *Lactobacillus* are used for testing. Initial tests include ELISA assays to establish general binding patterns. The antigenic structures that were used for the immunization of the mice leading to these monoclonals are well defined and the distribution patterns over the surface of a bacterial cell are known. Based on this and what is known about other monoclonals to similar or the same antigenic structures, the quantity of interaction expected can be estimated. In addition, commercially available monoclonal antibodies to these structures are used as controls (e.g., those available from Inotek Pharmaceuticals, Beverly, Mass.). It is contemplated that some of the monoclonals will have a broad range of cross-reactions with other organisms. This has been described on various occasions, especially between *E. coli* and other *Enterobacteriacae* (Feng et al., supra; Klebba et al., J Biol Chem 1990; 265:6800-10), but also between *E. coli* and *Salmonella* (O-antigens) (Westerman et al., J Clin Microbiol 1997; 35:679-84). The cross reactivity increases the number of potential target organisms that can be treated with one single broad-reacting monoclonal antibody.

D. Clone Immunoglobulin Genes from Candidates into Retroviral Backbone—Express in vitro—Test Binding The heavy and light chain variable regions of the immunoglobulin genes are amplified out of the cDNA by PCR using a commercially available Ig-primer kit. These primers consist of degenerate upper primers specific to the signal-peptide sequence at the 5'-end of the immunoglobulin heavy- or light chain and lower primers to different sections in the constant region, depending on the section that is to be isolated. A lower primer to the joining region is chosen to amplify just the variable region. Alternativley, a lower primer to the 3' UTR of the heavy- or light chain gene is chosen to amplify the entire framework. Once the PCR products are obtained using high-fidelity polymerase that ensures that error-free amplicons are generated, they are cloned into blunt end PCR cloning kits that are commercially available. Upon cloning of these fragments, multiple clones are analyzed by sequencing and sequences aligned with each other for comparison. Once the complete constructs have been confirmed by sequencing they are used in the first round of transfections that result in high titer pseudotyped retrovector for the transduction of production cell lines.

E. Reengineer the Antibody Constructs to Contain Biocide Fusions

The heavy chain gene is removed from the construct and replaced with a fusion that consists of the heavy chain gene, a C-terminal linker element and the gene of either human lysozyme or human phospholipase A (FIG. 7). The heavy chain-linker-lysozyme element is separated from the light chain gene via the IRES (internal ribosome binding site) element that enables individual translation of both products. The C terminus is used as it is least likely to give rise to steric hindrance at the antibody binding site. The $(Gly_4Ser)_3$ linker is used.

F. Expression of Biocide Fusions and Binding Tests

The retrovector is used to transduce production cell lines (CHO or 293) and obtain cells that have stably integrated copies of the construct. Upon clonal analysis to select clones with the highest production of fusion protein, the products are again tested for affinity and specificity as described in the above examples. Surface plasmon resonance analysis is used to determine exactly what influence the linker and biocide fusion portion have on the binding affinity of the antibody portion.

Example 16

Targeted Biocides Using Secretory IgA and Pentameric IgM as Delivery Molecules The example describes the construction and analysis of constructs comprising IgA and IgMs and biocides.

A. Obtain Secretory Component (SC) Through Engineering of pIgR Gene and Clone into Retroviral Backbone The cloning strategy for the murine polymeric immunoglobulin receptor (pIgR) gene (accession U06431) is based on published information about the sequence, structure and interaction of murine pIgR with IgA (Piskurich et al., J Immunol 1995; 154:1735-47). As a source for the pIgR gene total RNA is isolated from murine liver cells, which have been shown to produce high levels of pIgR (Piskurich et al., supra). After reverse transcribing the RNA, PCR is used to obtain the gene for the pIgR. Primers specific to the 3' UTR region and to the region upstream of position 2020 of the transmembrane region are designed and used to amplify a truncated version of the pIgR. The downstream primer is designed to introduce a stop codon right after amino acid position 594. The sequence corresponds to the cleaved secretory component found in circulation. A similar procedure has been published to make human secretory IgA (Rindisbacher et al., J Biol Chem 1995; 270:14220-8).

B. Create Secretory Component-Producing Cell Line by Using Existing J-Chain-Biocide Producing Cell Line The truncated pIgR gene obtained as described above is cloned into the retroviral backbone behind the simian CMV promoter as described earlier. CHO cells that already produce J-chain linked to biocide are superinfected with the pIgR construct and ELISA and Western Blot-based clonal analysis are performed to find clones that produce similar amounts of J-chain and secretory component. The resulting SC and J-chain-biocide producing cell line is used as a recipient cell line for the IgA constructs.

C. Use this Cell Line as Recipient for IgA Constructs

The next step towards a secretory IgA-producing cell line is to transduce the SC+J-chain-biocide producing cell line with reengineered IgA that is made by genetic assembly as described below. This construct is the first "fully artificially" produced mouse secretory IgA that incorporates all three components, the secretory component, the J-chain and a rearranged IgA, in one single production cell line. In addition it is the first time that the J-chain is engineered into a fusion protein.

D. Express Secretory IgA-Biocide Fusion in vitro and Test Binding

Production cell populations producing sIgA-biocide are subjected to clonal analysis in order to choose the highest producers. The selection of these clones focuses on dimeric secretory IgA-biocide detection. In order to make sure that the reengineered sIgA-biocide maintains its binding capabilities to bacterial surfaces, supernatants containing sIgA-biocide are tested by ELISA and flow cytometry as described above. Once satisfactory binding characteristics have been confirmed, candidates are chosen to go into the extensive testing series described below.

E. Engineer Variable Regions from PAMP-Reactive Immunoglobulins onto Constant IgA or IgM Region The constant IgA regions are obtained through extraction from IgA producing hybridomas. The immortalized monoclonal antibody-producing cell lines generated as described above are the source for the variable region genes. To obtain the variable regions from these cells the same procedures as described above with the exception that lower primers that anneal to the hinge region so that only the variable portion of the gene is amplified are used. The products are then cloned in frame into the existing IgA and IgM constant region constructs. These constructs representing anti-PAMP IgA are used to make sIgA-biocide fusion in cells that make SC and J-chain-biocide. Since the IgM does not incorporate the secretory component, the constructs representing anti-PAMP on an IgM framework are used to transduce production cells that make only the J-chain-biocide.

F. Express Pentameric IgM-Biocide Fusion in vitro and Test Binding

The anti-PAMP IgM constructed above is used to transduce JC-biocide producing production cells in analogy to the procedures described in Example 14. Product is tested for the pentameric structure and binding capabilities to PAMPs as well as whole bacterial cells. Candidates that are chosen based on their good binding and structure are taken into the extensive testing series described below.

Example 17

Bactericidal Testing System

This example describes testing methods for the analysis of candidate fusion proteins identified as described above. Constructs developed as described above are evaluated under the same conditions. Three test systems are used, as described below:

A. Testing in Bacterial Cell Culture

The lowest stringency test evaluates the bactericidal effect on test organisms in culture. Cultures of the test organism are exposed to a range of concentrations of the test product and control media for times ranging from 1-24 hours at 4° C. and 10° C. Aliquots in triplicate are re-plated on a growth medium to quantify the residual bacteria. The cell suspensions are also examined microscopically for clumping; various techniques are used to separate cells for quantification.

B. Testing in Bioflims and Ground Meat

For *Listeria* and *Lactobacillus*, the efficacy of constructs is tested in a biofilm model system; for *Lactobacillus, E. coli* and *Salmonella* the efficacy of bacterial killing is tested in a ground meat suspension.

Protocols for biofilm development and antimicrobial testing are known (Somers et al., 88th Ann. Meet. International Association for Food Protection, Minneapolis, Minn. Abstract P055. 2001). Stainless steel is used as a prototype surface for initial evaluation of the anti-listerial activity. Biofilms comprising a cocktail of *L. monocytogenes* or *Lactobacillus* isolates are established on 1 $cm^2$ pre-sterilized steel chips. Biofilm chips are exposed to various concentrations of the fusion protein products for up to 2 hours at room temperature. Chips are retrieved and evaluated for the number of viable cells quantified; adherent cells are removed by vortexing with glass beads and appropriate dilutions of the detached cells plated on nutrient agar plates for enumeration.

Raw beef or turkey is harvested from the interior of a large muscle section under sterile conditions to keep the background contamination at a minimum. This meat is then comminuted under sterile conditions to a slurry and pH adjusted. Several concentrations of the test products are added to the slurries. Following inoculation with test organisms the samples are incubated at 4° and 10° C. for up to 4 weeks. Triplicate samples per variable are assayed weekly for changes in bacterial population.

C. Simulation of Packing Plant Conditions

Meat product suspensions or a range of surface presentations of bacteria are used to simulate plant equipment and facilities. SPR testing of affinity binding guides the range of conditions tested. SPR is used to measure the effect of low or high pH, high salt concentrations and high temperatures on the capability of a given fusion protein to 'hang on' to its epitope. Those conditions that still allow the fusion protein to bind to its target are then tested in separate in vitro experiments for bacterial killing. For biofilms factors to be evaluated are attachment surface (e.g., buna N and food grade silicone rubber, polyurethane, polyester, polyethylene, and polypropylene), presence of food residues, cleaning/sanitizing agents, temperature, pH, and mixed biofilms.

Test organisms include, but are not limited to, field isolates of E. coli O157:H7, Salmonella, Listeria monocytogenes and Lactobacillus plantarum. Multiple isolates of the relevant organisms are available.

Example 18

Anti-Cryptosporidium Biocides

This Example describes biocides directed towards Cryptosporidium.

A. Materials and Methods

Oocyst and Sporozoite Isolation.

The Iowa C. parvum isolate (Heine, 1984) used in all experiments was propagated in newborn Cryptosporidium-free Holstein bull calves to obtain parasite material for study (Riggs, 1987). Oocysts were isolated by sucrose density gradient centrifugation and stored in 2.5% (wt/vol) $K_2Cr_2O_7$ (4° C.) prior to use (Arrowood, 1987). Immediately prior to excystation, oocysts were treated with hypochlorite (Riggs, 1987). Sporozoites were isolated from excysted oocyst preparations by passage through a polycarbonate filter (2.0 mm, pore size; Poretics, Livermore, Calif.).

Biocides and Host Cell Toxicity Assay

Lactoferrin (LF; Sigma), lactoferrin hydrolysate (LFH) (Murdock, 2002), lactoferricin B (LFB; Sigma), cathelicidin (CAT; LL-37, Phoenix), indolicidin (IND; Sigma), b-defensin 1 (BD1; Peptides international), b-defensin 2 (BD2; Peptides international), lysozyme (LYZ; Sigma), bee-venom phospholipase A2 (PLA2; Sigma), phospho-inositol specific phospholipase C (PI-PLC; Sigma).

Host cell toxicity assay was performed by measuring the release of lactate dehydrogenase (LDH) in the medium using a CYTOTOX 96 Non-Radioactive Cytotoxicity Assay kit (Promega, Madison, Wis.). Toxicity was therefore classified as non toxic 0-5% LDH release and mild toxicity 5-10% LDH release (ref).

Sporozoites Viability

Sporozoites viability was assessed using an adapted fluorescein diacetate (FDA) and propidium iodide (PI) vital dye technique (Arrowood, 1991 AAC). In brief, freshly excysted sporozoites were incubated for 15 min at 37° C. in the presence of the biocides or in control medium. Heat killed sporozoites (20 sec at 100° C.) were used as positive controls. Aliquots were supplemented with FDA and PI (8 mg/ml and 3 mg/ml final concentration, respectively), incubated for 5 min at room temperature and stored at 4° C. until examined. Viability was determined by counting the relative number of green-fluorescing (viable) and red-fluorescing (dead) sporozoites at a magnification of 200× on an epifluorescence microscope (a minimum of 100 sporozoites were counted for each condition, all experiments were performed in triplicates).

Infection of Caco-2 Monolayers and Automated Counting System

Caco-2 cells were grown to 90% confluency in complete MEM (MEM containing 10% fetal bovine serum, 1% nonessential amino acids, 100 U of penicillin per ml, and 100 mg of streptomycin per ml) on glass coverslips or in black plastic bottom 96-well plates for the automated counting system and infected as described before (Langer, 1999). Briefly, purified sporozoites in 50 ml of minimum essential medium [MEM]) were incubated (15 min, 37° C., 10% $CO_2$) with MAb 3E2 or isotype-matched control MAb or with the biocide and then inoculated onto the monolayer (three replicates per treatment for manual counting and five replicates for the automated counting). At 24 h postinoculation, cultures were washed with PBS, methanol fixed (4 min, −20° C.), blocked (PBS containing 3.2% [wt/vol] fish gelatin and 1% [wt/vol] bovine serum albumin [BSA]), and processed for IFA by using MAb 3E2 and affinity-purified fluoresceinated goat anti-mouse IgG-IgM-IgA (Kirkegaard & Perry, Gaithersburg, Md.) to detect intracellular stages. MAb 3E2 were prepared against immunoaffinity chromatography-isolated GP25-200 as previously described (Riggs, 1997).

Results were evaluated manually or using an automated system. Manually: Each coverslip was then systematically examined by the same investigator by epifluorescence microscopy to directly quantitate the number of intracellular stages per monolayer. Automated: Each well was examined using an epifluorescence microscope with automated stage coupled to a computer using Simple PCI software, 24 images of each well were recorded and analyzed using breakpoints for fluorescence intensity, size (area and diameter), and roundness in order to quantify the number of intracellular stages per monolayer. Non-infected monolayers were also counted in order to measure background. The mean numbers of intracellular stages in test and control cultures were examined for significant differences by using Student's two-tailed t test.

B. Results

The results are shown in Table 3 and FIGS. 13-16. Table 3 shows the toxicity of biocides to host cells. FIG. 13 shows the parasticidal activity of different biocides against C. parvum spores. FIG. 14 shows the P-values for the data of FIG. 13 against a no-biocide control. FIG. 15 shows the effect of biocides on C. parvum sporozoite infectivity for Caco-2 human intestinal epithelial cells. FIG. 16 shows the P-values for the data in FIG. 15. The results indicate that several biocides have activity against C. parvum spores and infectivity without significant toxicity against human cells.

TABLE 3

Non-Specific Toxicity of Biocides to Caco-2 Host Cells Measured by LDH Release

| | % LDH release | |
|---|---|---|
| Compound | 10 µg/ml | 100 µg/ml |
| MAb3E2 | 0.7 ± 1.1 | Nd |
| LF | 5.9 ± 1.2* | 5.8 ± 3.1 |
| LFH | 2.6 ± 3.5 | 0.7 ± 2.1 |
| LFB | 3.7 ± 2.3 | 2.6 ± 2.0 |
| CAT | 1.6 ± 0.3* | 5.6 ± 0.9* |
| IND | 0.9 ± 0.7 | 8.3 ± 3.5* |
| βD1 | 0.8 ± 1.0 | 2.3 ± 2.1 |
| βD2 | −0.9 ± 0.5 | 5.3 ± 1.5* |
| LYZ | Nd | −1.9 ± 1.3 |
| PLA2 | Nd | 0.7 ± 0.7 |
| PI-PLC | Nd | −1.4 ± 0.9 |

Nd: not determined
*$P < 0.05$ to control (medium alone for 2 h)

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating a subject comprising:
    a) providing
        (i) a protein biocide active against *Cryptosporidium parvum*, wherein said protein biocide is phospholipase A2; and
        (ii) a subject infected with *Cryptosporidium parvum*; and
    b) orally administering said protein biocide to said subject under conditions such that said protein biocide reduces the growth or replication of said *Cryptosporidium parvum*.

2. The method of claim 1, wherein said subject is a mammal.

3. The method of claim 2, wherein said mammal is a ruminant.

4. The method of claim 3, wherein said ruminant is a bovine.

5. The method of claim 2, wherein said mammal is a human.

* * * * *

```
                            SEQUENCE LISTING

<160> NUMBER OF SEQ ID NOS: 104

<210> SEQ ID NO 1
<211> LENGTH: 64
<212> TYPE: PRT
<213> ORGANISM: Bos taurus

<400> SEQUENCE: 1

Met Arg Leu His His Leu Leu Ala Leu Leu Phe Leu Val Leu Ser
1               5                   10                  15

Ala Gly Ser Gly Phe Thr Gln Gly Val Arg Asn Ser Gln Ser Cys Arg
            20                  25                  30

Arg Asn Lys Gly Ile Cys Val Pro Ile Arg Cys Pro Gly Ser Met Arg
        35                  40                  45

Gln Ile Gly Thr Cys Leu Gly Ala Gln Val Lys Cys Cys Arg Arg Lys
    50                  55                  60

<210> SEQ ID NO 2
<211> LENGTH: 24
<212> TYPE: PRT
<213> ORGANISM: Xenopus laevis

<400> SEQUENCE: 2

Gly Val Leu Ser Asn Val Ile Gly Tyr Leu Lys Lys Leu Gly Thr Gly
1               5                   10                  15

Ala Leu Asn Ala Val Leu Lys Gln
            20

<210> SEQ ID NO 3
<211> LENGTH: 81
<212> TYPE: PRT
<213> ORGANISM: Xenopus laevis

<400> SEQUENCE: 3

Met Tyr Lys Gly Ile Phe Leu Cys Val Leu Leu Ala Val Ile Cys Ala
1               5                   10                  15

Asn Ser Leu Ala Thr Pro Ser Ser Asp Ala Asp Glu Asn Asp Glu
            20                  25                  30

Val Glu Arg Tyr Val Arg Gly Trp Ala Ser Lys Ile Gly Gln Thr Leu
        35                  40                  45

Gly Lys Ile Ala Lys Val Gly Leu Lys Glu Leu Ile Gln Pro Lys Arg
    50                  55                  60

Glu Ala Met Leu Arg Ser Ala Glu Ala Gln Gly Lys Arg Pro Trp Ile
65                  70                  75                  80

Leu

<210> SEQ ID NO 4
<211> LENGTH: 303
<212> TYPE: PRT
<213> ORGANISM: Xenopus laevis

<400> SEQUENCE: 4

Met Phe Lys Gly Leu Phe Ile Cys Ser Leu Ile Ala Val Ile Cys Ala
```

```
                1               5                   10                  15
Asn Ala Leu Pro Gln Pro Glu Ala Ser Ala Asp Glu Asp Met Asp Glu
                    20                  25                  30

Arg Glu Val Arg Gly Ile Gly Lys Phe Leu His Ser Ala Gly Lys Phe
            35                  40                  45

Gly Lys Ala Phe Val Gly Glu Ile Met Lys Ser Lys Arg Asp Ala Glu
        50                  55                  60

Ala Val Gly Pro Glu Ala Phe Ala Asp Glu Asp Leu Asp Glu Arg Glu
65                  70                  75                  80

Val Arg Gly Ile Gly Lys Phe Leu His Ser Ala Lys Lys Phe Gly Lys
                85                  90                  95

Ala Phe Val Gly Glu Ile Met Asn Ser Lys Arg Asp Ala Glu Ala Val
            100                 105                 110

Gly Pro Glu Ala Phe Ala Asp Glu Asp Leu Asp Glu Arg Glu Val Arg
        115                 120                 125

Gly Ile Gly Lys Phe Leu His Ser Ala Lys Lys Phe Gly Lys Ala Phe
    130                 135                 140

Val Gly Glu Ile Met Asn Ser Lys Arg Asp Ala Glu Ala Val Gly Pro
145                 150                 155                 160

Glu Ala Phe Ala Asp Glu Asp Leu Asp Glu Arg Glu Val Arg Gly Ile
                165                 170                 175

Gly Lys Phe Leu His Ser Ala Lys Lys Phe Gly Lys Ala Phe Val Gly
            180                 185                 190

Glu Ile Met Asn Ser Lys Arg Asp Ala Glu Ala Val Gly Pro Glu Ala
        195                 200                 205

Phe Ala Asp Glu Asp Phe Asp Glu Arg Glu Val Arg Gly Ile Gly Lys
    210                 215                 220

Phe Leu His Ser Ala Lys Lys Phe Gly Lys Ala Phe Val Gly Glu Ile
225                 230                 235                 240

Met Asn Ser Lys Arg Asp Ala Glu Ala Val Gly Pro Glu Ala Phe Ala
                245                 250                 255

Asp Glu Asp Leu Asp Glu Arg Glu Val Arg Gly Ile Gly Lys Phe Leu
            260                 265                 270

His Ser Ala Lys Lys Phe Gly Lys Ala Phe Val Gly Glu Ile Met Asn
        275                 280                 285

Ser Lys Arg Asp Ala Glu Ala Val Asp Asp Arg Arg Trp Val Glu
    290                 295                 300

<210> SEQ ID NO 5
<211> LENGTH: 17
<212> TYPE: PRT
<213> ORGANISM: Tachypleus gigas

<400> SEQUENCE: 5

Lys Trp Cys Phe Arg Val Cys Tyr Arg Gly Ile Cys Tyr Arg Arg Cys
1               5                   10                  15

Arg

<210> SEQ ID NO 6
<211> LENGTH: 17
<212> TYPE: PRT
<213> ORGANISM: Tachypleus gigas

<400> SEQUENCE: 6

Arg Trp Cys Phe Arg Val Cys Tyr Arg Gly Ile Cys Tyr Arg Lys Cys
1               5                   10                  15
```

Arg

<210> SEQ ID NO 7
<211> LENGTH: 129
<212> TYPE: PRT
<213> ORGANISM: Bufo gargarizans

<400> SEQUENCE: 7

Met Ser Gly Arg Gly Lys Gln Gly Gly Lys Val Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Gln Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Val Arg Asn Asp Glu Glu Leu Asn Lys
                85                  90                  95

Leu Leu Gly Gly Val Thr Ile Ala Gln Gly Gly Val Leu Pro Asn Ile
            100                 105                 110

Gln Ala Val Leu Leu Pro Lys Thr Glu Ser Ser Lys Pro Ala Lys Ser
        115                 120                 125

Lys

<210> SEQ ID NO 8
<211> LENGTH: 21
<212> TYPE: PRT
<213> ORGANISM: Bufo gargarizans

<400> SEQUENCE: 8

Thr Arg Ser Ser Arg Ala Gly Leu Gln Phe Pro Val Gly Arg Val His
1               5                   10                  15

Arg Leu Leu Arg Lys
            20

<210> SEQ ID NO 9
<211> LENGTH: 63
<212> TYPE: PRT
<213> ORGANISM: Bombyx mori

<400> SEQUENCE: 9

Met Asn Phe Val Arg Ile Leu Ser Phe Val Phe Ala Leu Val Leu Ala
1               5                   10                  15

Leu Gly Ala Val Ser Ala Ala Pro Glu Pro Arg Trp Lys Leu Phe Lys
            20                  25                  30

Lys Ile Glu Lys Val Gly Arg Asn Val Arg Asp Gly Leu Ile Lys Ala
        35                  40                  45

Gly Pro Ala Ile Ala Val Ile Gly Gln Ala Lys Ser Leu Gly Lys
    50                  55                  60

<210> SEQ ID NO 10
<211> LENGTH: 63
<212> TYPE: PRT
<213> ORGANISM: Bombyx mori

<400> SEQUENCE: 10

```
Met Asn Phe Ala Lys Ile Leu Ser Phe Val Phe Ala Leu Val Leu Ala
1               5                   10                  15

Leu Ser Met Thr Ser Ala Ala Pro Glu Pro Arg Trp Lys Ile Phe Lys
                20                  25                  30

Lys Ile Glu Lys Met Gly Arg Asn Ile Arg Asp Gly Ile Val Lys Ala
            35                  40                  45

Gly Pro Ala Ile Glu Val Leu Gly Ser Ala Lys Ala Ile Gly Lys
        50                  55                  60
```

<210> SEQ ID NO 11
<211> LENGTH: 63
<212> TYPE: PRT
<213> ORGANISM: Drosophila melanogaster

<400> SEQUENCE: 11

```
Met Asn Phe Tyr Lys Ile Phe Val Phe Val Ala Leu Ile Leu Ala Ile
1               5                   10                  15

Ser Ile Gly Gln Ser Glu Ala Gly Trp Leu Lys Lys Leu Gly Lys Arg
                20                  25                  30

Ile Glu Arg Ile Gly Gln His Thr Arg Asp Ala Thr Ile Gln Gly Leu
            35                  40                  45

Gly Ile Ala Gln Gln Ala Ala Asn Val Ala Ala Thr Ala Arg Gly
        50                  55                  60
```

<210> SEQ ID NO 12
<211> LENGTH: 31
<212> TYPE: PRT
<213> ORGANISM: Sus scrofa

<400> SEQUENCE: 12

```
Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30
```

<210> SEQ ID NO 13
<211> LENGTH: 13
<212> TYPE: PRT
<213> ORGANISM: Bos taurus

<400> SEQUENCE: 13

```
Ile Leu Pro Trp Lys Trp Pro Trp Trp Pro Trp Arg Arg
1               5                   10
```

<210> SEQ ID NO 14
<211> LENGTH: 34
<212> TYPE: PRT
<213> ORGANISM: Lactococcus lactis

<400> SEQUENCE: 14

```
Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
                20                  25                  30

Ser Lys
```

<210> SEQ ID NO 15
<211> LENGTH: 20
<212> TYPE: PRT
<213> ORGANISM: Rana catesbeiana

```
<400> SEQUENCE: 15

Phe Leu Gly Gly Leu Ile Lys Ile Val Pro Ala Met Ile Cys Ala Val
1               5                   10                  15

Thr Lys Lys Cys
            20

<210> SEQ ID NO 16
<211> LENGTH: 25
<212> TYPE: PRT
<213> ORGANISM: Bos taurus

<400> SEQUENCE: 16

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 17
<211> LENGTH: 19
<212> TYPE: PRT
<213> ORGANISM: Sus scrofa
<220> FEATURE:
<221> NAME/KEY: misc_feature
<222> LOCATION: (19)..(19)
<223> OTHER INFORMATION: Xaa can be any naturally occurring amino acid

<400> SEQUENCE: 17

Arg Gly Gly Arg Leu Cys Tyr Cys Arg Arg Arg Phe Cys Val Cys Val
1               5                   10                  15

Gly Arg Xaa

<210> SEQ ID NO 18
<211> LENGTH: 16
<212> TYPE: PRT
<213> ORGANISM: Sus scrofa

<400> SEQUENCE: 18

Gly Gly Arg Leu Cys Tyr Cys Arg Arg Arg Phe Cys Ile Cys Val Gly
1               5                   10                  15

<210> SEQ ID NO 19
<211> LENGTH: 51
<212> TYPE: PRT
<213> ORGANISM: Homo sapiens

<400> SEQUENCE: 19

Met Lys Phe Phe Val Phe Ala Leu Ile Leu Ala Leu Met Leu Ser Met
1               5                   10                  15

Thr Gly Ala Asp Ser His Ala Lys Arg His His Gly Tyr Lys Arg Lys
            20                  25                  30

Phe His Glu Lys His His Ser His Arg Gly Tyr Arg Ser Asn Tyr Leu
        35                  40                  45

Tyr Asp Asn
    50

<210> SEQ ID NO 20
<211> LENGTH: 38
<212> TYPE: PRT
<213> ORGANISM: Macaca fascicularis

<400> SEQUENCE: 20

Asp Ser His Glu Glu Arg His His Gly Arg His Gly His His Lys Tyr
```

```
                1               5                   10                  15
Gly Arg Lys Phe His Glu Lys His His Ser His Arg Gly Tyr Arg Ser
                20                  25                  30

Asn Tyr Leu Tyr Asp Asn
        35

<210> SEQ ID NO 21
<211> LENGTH: 33
<212> TYPE: PRT
<213> ORGANISM: Phyllomedusa sauvagei

<400> SEQUENCE: 21

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Thr
                20                  25                  30

Gln

<210> SEQ ID NO 22
<211> LENGTH: 34
<212> TYPE: PRT
<213> ORGANISM: Phyllomedusa sauvagei

<400> SEQUENCE: 22

Ala Leu Trp Phe Thr Met Leu Lys Lys Leu Gly Thr Met Ala Leu His
1               5                   10                  15

Ala Gly Lys Ala Ala Leu Gly Ala Ala Ala Asn Thr Ile Ser Gln Gly
                20                  25                  30

Thr Gln

<210> SEQ ID NO 23
<211> LENGTH: 30
<212> TYPE: PRT
<213> ORGANISM: Phyllomedusa sauvagei

<400> SEQUENCE: 23

Ala Leu Trp Lys Asn Met Leu Lys Gly Ile Gly Lys Leu Ala Gly Lys
1               5                   10                  15

Ala Ala Leu Gly Ala Val Lys Lys Leu Val Gly Ala Glu Ser
                20                  25                  30

<210> SEQ ID NO 24
<211> LENGTH: 21
<212> TYPE: PRT
<213> ORGANISM: Misgurnus anguillicaudatus

<400> SEQUENCE: 24

Arg Gln Arg Val Glu Glu Leu Ser Lys Phe Ser Lys Lys Gly Ala Ala
1               5                   10                  15

Ala Arg Arg Arg Lys
                20

<210> SEQ ID NO 25
<211> LENGTH: 27
<212> TYPE: PRT
<213> ORGANISM: Apis mellifera

<400> SEQUENCE: 25

Gly Ile Gly Ala Val Leu Lys Val Leu Thr Thr Gly Leu Pro Ala Leu
1               5                   10                  15
```

```
Ile Ser Trp Ile Ser Arg Lys Lys Arg Gln Gln
            20                  25

<210> SEQ ID NO 26
<211> LENGTH: 33
<212> TYPE: PRT
<213> ORGANISM: Pardachirus pavoninus

<400> SEQUENCE: 26

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Glu Gln
            20                  25                  30

Glu

<210> SEQ ID NO 27
<211> LENGTH: 33
<212> TYPE: PRT
<213> ORGANISM: Pardachirus pavoninus

<400> SEQUENCE: 27

Gly Phe Phe Ala Leu Ile Pro Lys Ile Ile Ser Ser Pro Ile Phe Lys
1               5                   10                  15

Thr Leu Leu Ser Ala Val Gly Ser Ala Leu Ser Ser Ser Gly Gly Gln
            20                  25                  30

Glu

<210> SEQ ID NO 28
<211> LENGTH: 176
<212> TYPE: PRT
<213> ORGANISM: Bos taurus

<400> SEQUENCE: 28

Met Glu Thr Gln Arg Ala Ser Leu Ser Leu Gly Arg Cys Ser Leu Trp
1               5                   10                  15

Leu Leu Leu Leu Gly Leu Val Leu Pro Ser Ala Ser Ala Gln Ala Leu
            20                  25                  30

Ser Tyr Arg Glu Ala Val Leu Arg Ala Val Asp Gln Phe Asn Glu Arg
        35                  40                  45

Ser Ser Glu Ala Asn Leu Tyr Arg Leu Leu Glu Leu Asp Pro Thr Pro
    50                  55                  60

Asn Asp Asp Leu Asp Pro Gly Thr Arg Lys Pro Val Ser Phe Arg Val
65                  70                  75                  80

Lys Glu Thr Asp Cys Pro Arg Thr Ser Gln Gln Pro Leu Glu Gln Cys
                85                  90                  95

Asp Phe Lys Glu Asn Gly Leu Val Lys Gln Cys Val Gly Thr Val Thr
            100                 105                 110

Leu Asp Pro Ser Asn Asp Gln Phe Asp Ile Asn Cys Asn Glu Leu Gln
        115                 120                 125

Ser Val Arg Phe Arg Pro Pro Ile Arg Arg Pro Pro Ile Arg Pro Pro
    130                 135                 140

Phe Tyr Pro Pro Phe Arg Pro Pro Ile Arg Pro Pro Ile Phe Pro Pro
145                 150                 155                 160

Ile Arg Pro Pro Phe Arg Pro Pro Leu Gly Pro Phe Pro Gly Arg Arg
                165                 170                 175

<210> SEQ ID NO 29
<211> LENGTH: 155
```

<212> TYPE: PRT
<213> ORGANISM: Bos taurus

<400> SEQUENCE: 29

Met Glu Thr Pro Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
                20                  25                  30

Ser Tyr Arg Glu Ala Val Leu Arg Ala Val Asp Gln Leu Asn Glu Gln
            35                  40                  45

Ser Ser Glu Pro Asn Ile Tyr Arg Leu Leu Glu Leu Asp Gln Pro Pro
        50                  55                  60

Gln Asp Asp Glu Asp Pro Asp Ser Pro Lys Arg Val Ser Phe Arg Val
65                  70                  75                  80

Lys Glu Thr Val Cys Ser Arg Thr Thr Gln Gln Pro Pro Glu Gln Cys
                85                  90                  95

Asp Phe Lys Glu Asn Gly Leu Leu Lys Arg Cys Glu Gly Thr Val Thr
            100                 105                 110

Leu Asp Gln Val Arg Gly Asn Phe Asp Ile Thr Cys Asn Asn His Gln
        115                 120                 125

Ser Ile Arg Ile Thr Lys Gln Pro Trp Ala Pro Pro Gln Ala Ala Arg
    130                 135                 140

Leu Cys Arg Ile Val Val Ile Arg Val Cys Arg
145                 150                 155

<210> SEQ ID NO 30
<211> LENGTH: 29
<212> TYPE: PRT
<213> ORGANISM: Ceratitis capitata

<400> SEQUENCE: 30

Ser Ile Gly Ser Ala Leu Lys Lys Ala Leu Pro Val Ala Lys Lys Ile
1               5                   10                  15

Gly Lys Ile Ala Leu Pro Ile Ala Lys Ala Ala Leu Pro
                20                  25

<210> SEQ ID NO 31
<211> LENGTH: 29
<212> TYPE: PRT
<213> ORGANISM: Ceratitis capitata

<400> SEQUENCE: 31

Ser Ile Gly Ser Ala Phe Lys Lys Ala Leu Pro Val Ala Lys Lys Ile
1               5                   10                  15

Gly Lys Ala Ala Leu Pro Ile Ala Lys Ala Ala Leu Pro
                20                  25

<210> SEQ ID NO 32
<211> LENGTH: 170
<212> TYPE: PRT
<213> ORGANISM: Homo sapiens

<400> SEQUENCE: 32

Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
            35                  40                  45

```
Arg Ser Ser Asp Ala Asn Leu Tyr Arg Leu Leu Asp Leu Asp Pro Arg
         50                  55                  60

Pro Thr Met Asp Gly Asp Pro Asp Thr Pro Lys Pro Val Ser Phe Thr
 65                  70                  75                  80

Val Lys Glu Thr Val Cys Pro Arg Thr Gln Gln Ser Pro Glu Asp
                 85                  90                  95

Cys Asp Phe Lys Lys Asp Gly Leu Val Lys Arg Cys Met Gly Thr Val
             100                 105                 110

Thr Leu Asn Gln Ala Arg Gly Ser Phe Asp Ile Ser Cys Asp Lys Asp
             115                 120                 125

Asn Lys Arg Phe Ala Leu Leu Gly Asp Phe Arg Lys Ser Lys Glu
         130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

<210> SEQ ID NO 33
<211> LENGTH: 170
<212> TYPE: PRT
<213> ORGANISM: Equus caballus

<400> SEQUENCE: 33

Met Glu Thr Gln Arg Asn Thr Arg Cys Leu Gly Arg Trp Ser Pro Leu
1               5                   10                  15

Leu Leu Leu Leu Gly Leu Val Ile Pro Pro Ala Thr Thr Gln Ala Leu
                20                  25                  30

Ser Tyr Lys Glu Ala Val Leu Arg Ala Val Asp Gly Leu Asn Gln Arg
             35                  40                  45

Ser Ser Asp Glu Asn Leu Tyr Arg Leu Leu Glu Leu Asp Pro Leu Pro
         50                  55                  60

Lys Gly Asp Lys Asp Ser Asp Thr Pro Lys Pro Val Ser Phe Met Val
 65                  70                  75                  80

Lys Glu Thr Val Cys Pro Arg Ile Met Lys Gln Thr Pro Glu Gln Cys
                 85                  90                  95

Asp Phe Lys Glu Asn Gly Leu Val Lys Gln Cys Val Gly Thr Val Ile
             100                 105                 110

Leu Asp Pro Val Lys Asp Tyr Phe Asp Ala Ser Cys Asp Glu Pro Gln
             115                 120                 125

Arg Val Lys Arg Phe His Ser Val Gly Ser Leu Ile Gln Arg His Gln
         130                 135                 140

Gln Met Ile Arg Asp Lys Ser Glu Ala Thr Arg His Gly Ile Arg Ile
145                 150                 155                 160

Ile Thr Arg Pro Lys Leu Leu Leu Ala Ser
                165                 170

<210> SEQ ID NO 34
<211> LENGTH: 159
<212> TYPE: PRT
<213> ORGANISM: Bos taurus

<400> SEQUENCE: 34

Met Glu Thr Gln Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
                20                  25                  30
```

```
Ser Tyr Arg Glu Ala Val Leu Arg Ala Val Asp Gln Leu Asn Glu Lys
        35                  40                  45

Ser Ser Glu Ala Asn Leu Tyr Arg Leu Leu Glu Leu Asp Pro Pro Pro
 50                  55                  60

Lys Glu Asp Asp Glu Asn Pro Asn Ile Pro Lys Pro Val Ser Phe Arg
 65                  70                  75                  80

Val Lys Glu Thr Val Cys Pro Arg Thr Ser Gln Gln Ser Pro Glu Gln
                85                  90                  95

Cys Asp Phe Lys Glu Asn Gly Leu Leu Lys Glu Cys Val Gly Thr Val
                100                 105                 110

Thr Leu Asp Gln Val Gly Ser Asn Phe Asp Ile Thr Cys Ala Val Pro
                115                 120                 125

Gln Ser Val Gly Gly Leu Arg Ser Leu Gly Arg Lys Ile Leu Arg Ala
        130                 135                 140

Trp Lys Lys Tyr Gly Pro Ile Ile Val Pro Ile Ile Arg Ile Gly
145                 150                 155

<210> SEQ ID NO 35
<211> LENGTH: 156
<212> TYPE: PRT
<213> ORGANISM: Equus caballus

<400> SEQUENCE: 35

Met Glu Thr Gln Arg Asn Thr Arg Cys Leu Gly Arg Trp Ser Pro Leu
 1               5                  10                  15

Leu Leu Leu Leu Gly Leu Val Ile Pro Pro Ala Thr Gln Ala Leu
        20                  25                  30

Ser Tyr Lys Glu Ala Val Leu Arg Ala Val Asp Gly Leu Asn Gln Arg
        35                  40                  45

Ser Ser Asp Glu Asn Leu Tyr Arg Leu Leu Glu Leu Asp Pro Leu Pro
 50                  55                  60

Lys Gly Asp Lys Asp Ser Asp Thr Pro Lys Pro Val Ser Phe Met Val
 65                  70                  75                  80

Lys Glu Thr Val Cys Pro Arg Ile Met Lys Gln Thr Pro Glu Gln Cys
                85                  90                  95

Asp Phe Lys Glu Asn Gly Leu Val Lys Gln Cys Val Gly Thr Val Ile
                100                 105                 110

Leu Gly Pro Val Lys Asp His Phe Asp Val Ser Cys Gly Glu Pro Gln
        115                 120                 125

Arg Val Lys Arg Phe Gly Arg Leu Ala Lys Ser Phe Leu Arg Met Arg
        130                 135                 140

Ile Leu Leu Pro Arg Arg Lys Ile Leu Leu Ala Ser
145                 150                 155

<210> SEQ ID NO 36
<211> LENGTH: 160
<212> TYPE: PRT
<213> ORGANISM: Ovis aries

<400> SEQUENCE: 36

Met Glu Thr Gln Arg Ala Ser Leu Ser Leu Gly Arg Cys Ser Leu Trp
 1               5                  10                  15

Leu Leu Leu Leu Gly Leu Ala Leu Pro Ser Ala Ser Ala Gln Val Leu
        20                  25                  30

Ser Tyr Arg Glu Ala Val Leu Arg Ala Ala Asp Gln Leu Asn Glu Lys
        35                  40                  45
```

```
Ser Ser Glu Ala Asn Leu Tyr Arg Leu Leu Glu Leu Asp Pro Pro
 50                  55                  60

Lys Gln Asp Asp Glu Asn Ser Asn Ile Pro Lys Pro Val Ser Phe Arg
 65                  70                  75                  80

Val Lys Glu Thr Val Cys Pro Arg Thr Ser Gln Gln Pro Ala Glu Gln
                 85                  90                  95

Cys Asp Phe Lys Glu Asn Gly Leu Leu Lys Glu Cys Val Gly Thr Val
                100                 105                 110

Thr Leu Asp Gln Val Arg Asn Asn Phe Asp Ile Thr Cys Ala Glu Pro
            115                 120                 125

Gln Ser Val Arg Gly Leu Arg Arg Leu Gly Arg Lys Ile Ala His Gly
        130                 135                 140

Val Lys Lys Tyr Gly Pro Thr Val Leu Arg Ile Ile Arg Ile Ala Gly
145                 150                 155                 160

<210> SEQ ID NO 37
<211> LENGTH: 12
<212> TYPE: PRT
<213> ORGANISM: Bos taurus

<400> SEQUENCE: 37

Arg Leu Cys Arg Ile Val Val Ile Arg Val Cys Arg
1               5                   10

<210> SEQ ID NO 38
<211> LENGTH: 30
<212> TYPE: PRT
<213> ORGANISM: Homo sapiens

<400> SEQUENCE: 38

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 39
<211> LENGTH: 29
<212> TYPE: PRT
<213> ORGANISM: Homo sapiens

<400> SEQUENCE: 39

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 40
<211> LENGTH: 30
<212> TYPE: PRT
<213> ORGANISM: Homo sapiens

<400> SEQUENCE: 40

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 41
<211> LENGTH: 33
<212> TYPE: PRT
```

-continued

```
<213> ORGANISM: Homo sapiens

<400> SEQUENCE: 41

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30
Val

<210> SEQ ID NO 42
<211> LENGTH: 33
<212> TYPE: PRT
<213> ORGANISM: Oryctolagus cuniculus

<400> SEQUENCE: 42

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
            20                  25                  30
Arg

<210> SEQ ID NO 43
<211> LENGTH: 33
<212> TYPE: PRT
<213> ORGANISM: Oryctolagus cuniculus

<400> SEQUENCE: 43

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30
Arg

<210> SEQ ID NO 44
<211> LENGTH: 34
<212> TYPE: PRT
<213> ORGANISM: Oryctolagus cuniculus

<400> SEQUENCE: 44

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30
Arg Arg

<210> SEQ ID NO 45
<211> LENGTH: 34
<212> TYPE: PRT
<213> ORGANISM: Oryctolagus cuniculus

<400> SEQUENCE: 45

Gly Arg Cys Val Cys Arg Lys Gln Leu Leu Cys Ser Tyr Arg Glu Arg
1               5                   10                  15

Arg Ile Gly Asp Cys Lys Ile Arg Gly Val Arg Phe Pro Phe Cys Cys
            20                  25                  30
Pro Arg

<210> SEQ ID NO 46
<211> LENGTH: 34
```

```
<212> TYPE: PRT
<213> ORGANISM: Oryctolagus cuniculus

<400> SEQUENCE: 46

Val Ser Cys Thr Cys Arg Arg Phe Ser Cys Gly Phe Gly Glu Arg Ala
1               5                   10                  15

Ser Gly Ser Cys Thr Val Asn Gly Gly Val Arg His Thr Leu Cys Cys
            20                  25                  30

Arg Arg

<210> SEQ ID NO 47
<211> LENGTH: 33
<212> TYPE: PRT
<213> ORGANISM: Oryctolagus cuniculus

<400> SEQUENCE: 47

Val Phe Cys Thr Cys Arg Gly Phe Leu Cys Gly Ser Gly Glu Arg Ala
1               5                   10                  15

Ser Gly Ser Cys Thr Ile Asn Gly Val Arg His Thr Leu Cys Cys Arg
            20                  25                  30

Arg

<210> SEQ ID NO 48
<211> LENGTH: 32
<212> TYPE: PRT
<213> ORGANISM: Rattus norvegicus

<400> SEQUENCE: 48

Val Thr Cys Tyr Cys Arg Arg Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 49
<211> LENGTH: 30
<212> TYPE: PRT
<213> ORGANISM: Rattus norvegicus

<400> SEQUENCE: 49

Cys Ser Cys Arg Tyr Ser Ser Cys Arg Phe Gly Glu Arg Leu Leu Ser
1               5                   10                  15

Gly Ala Cys Arg Leu Asn Gly Arg Ile Tyr Arg Leu Cys Cys
            20                  25                  30

<210> SEQ ID NO 50
<211> LENGTH: 31
<212> TYPE: PRT
<213> ORGANISM: Rattus norvegicus

<400> SEQUENCE: 50

Ala Cys Thr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30

<210> SEQ ID NO 51
<211> LENGTH: 31
<212> TYPE: PRT
<213> ORGANISM: Guinea pig

<400> SEQUENCE: 51
```

```
Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
                20                  25                  30
```

<210> SEQ ID NO 52
<211> LENGTH: 67
<212> TYPE: PRT
<213> ORGANISM: Homo sapiens

<400> SEQUENCE: 52

```
Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
                20                  25                  30

Cys Arg Val Arg Gly Gly Arg Cys Ala Val Leu Ser Cys Leu Pro Lys
                35                  40                  45

Glu Glu Gln Ile Gly Lys Cys Ser Thr Arg Gly Arg Lys Cys Cys Arg
            50                  55                  60

Arg Lys Lys
65
```

<210> SEQ ID NO 53
<211> LENGTH: 18
<212> TYPE: PRT
<213> ORGANISM: Macaca mulatta

<400> SEQUENCE: 53

```
Arg Cys Ile Cys Thr Arg Gly Phe Cys Arg Cys Leu Cys Arg Arg Gly
1               5                   10                  15

Val Cys
```

<210> SEQ ID NO 54
<211> LENGTH: 78
<212> TYPE: PRT
<213> ORGANISM: Helianthus annuus

<400> SEQUENCE: 54

```
Met Lys Ser Ser Met Lys Met Phe Ala Ala Leu Leu Leu Val Val Met
1               5                   10                  15

Cys Leu Leu Ala Asn Glu Met Gly Gly Pro Leu Val Val Glu Ala Arg
                20                  25                  30

Thr Cys Glu Ser Gln Ser His Lys Phe Lys Gly Thr Cys Leu Ser Asp
                35                  40                  45

Thr Asn Cys Ala Asn Val Cys His Ser Glu Arg Phe Ser Gly Gly Lys
            50                  55                  60

Cys Arg Gly Phe Arg Arg Arg Cys Phe Cys Thr Thr His Cys
65                  70                  75
```

<210> SEQ ID NO 55
<211> LENGTH: 78
<212> TYPE: PRT
<213> ORGANISM: Helianthus annuus

<400> SEQUENCE: 55

```
Met Lys Ser Ser Met Lys Met Phe Ala Ala Leu Leu Leu Val Val Met
1               5                   10                  15

Cys Leu Leu Ala Asn Glu Met Gly Gly Pro Leu Val Val Glu Ala Arg
                20                  25                  30
```

-continued

```
Thr Cys Glu Ser Gln Ser His Lys Phe Lys Gly Thr Cys Leu Ser Asp
        35                  40                  45

Thr Asn Cys Ala Asn Val Cys His Ser Glu Arg Phe Ser Gly Gly Lys
    50                  55                  60

Cys Arg Gly Phe Arg Arg Arg Cys Phe Cys Thr Thr His Cys
65                  70                  75
```

<210> SEQ ID NO 56
<211> LENGTH: 30
<212> TYPE: PRT
<213> ORGANISM: Macaca mulatta

<400> SEQUENCE: 56

```
Ala Cys Tyr Cys Arg Ile Pro Ala Cys Leu Ala Gly Glu Arg Arg Tyr
1               5                   10                  15

Gly Thr Cys Phe Tyr Met Gly Arg Val Trp Ala Phe Cys Cys
            20                  25                  30
```

<210> SEQ ID NO 57
<211> LENGTH: 37
<212> TYPE: PRT
<213> ORGANISM: Androctonus australis hector

<400> SEQUENCE: 57

```
Gly Phe Gly Cys Pro Phe Asn Gln Gly Ala Cys His Arg His Cys Arg
1               5                   10                  15

Ser Ile Arg Arg Arg Gly Gly Tyr Cys Ala Gly Leu Phe Lys Gln Thr
            20                  25                  30

Cys Thr Cys Tyr Arg
        35
```

<210> SEQ ID NO 58
<211> LENGTH: 38
<212> TYPE: PRT
<213> ORGANISM: Mytilus galloprovincialis
<220> FEATURE:
<221> NAME/KEY: misc_feature
<222> LOCATION: (28)..(28)
<223> OTHER INFORMATION: Xaa can be any naturally occurring amino acid

<400> SEQUENCE: 58

```
Gly Phe Gly Cys Pro Asn Asn Tyr Gln Cys His Arg His Cys Lys Ser
1               5                   10                  15

Ile Pro Gly Arg Cys Gly Gly Tyr Cys Gly Gly Xaa His Arg Leu Arg
            20                  25                  30

Cys Thr Cys Tyr Arg Cys
        35
```

<210> SEQ ID NO 59
<211> LENGTH: 54
<212> TYPE: PRT
<213> ORGANISM: Heuchera sanguinea

<400> SEQUENCE: 59

```
Asp Gly Val Lys Leu Cys Asp Val Pro Ser Gly Thr Trp Ser Gly His
1               5                   10                  15

Cys Gly Ser Ser Ser Lys Cys Ser Gln Gln Cys Lys Asp Arg Glu His
            20                  25                  30

Phe Ala Tyr Gly Gly Ala Cys His Tyr Gln Phe Pro Ser Val Lys Cys
        35                  40                  45

Phe Cys Lys Arg Gln Cys
```

```
<210> SEQ ID NO 60
<211> LENGTH: 49
<212> TYPE: PRT
<213> ORGANISM: Clitoria ternatea

<400> SEQUENCE: 60

Asn Leu Cys Glu Arg Ala Ser Leu Thr Trp Thr Gly Asn Cys Gly Asn
1               5                   10                  15

Thr Gly His Cys Asp Thr Gln Cys Arg Asn Trp Glu Ser Ala Lys His
            20                  25                  30

Gly Ala Cys His Lys Arg Gly Asn Trp Lys Cys Phe Cys Tyr Phe Asn
        35                  40                  45

Cys

<210> SEQ ID NO 61
<211> LENGTH: 91
<212> TYPE: PRT
<213> ORGANISM: Mus musculus

<400> SEQUENCE: 61

Met Lys Lys Leu Val Leu Leu Phe Ala Leu Val Leu Leu Ala Phe Gln
1               5                   10                  15

Val Gln Ala Asp Ser Ile Gln Asn Thr Asp Glu Glu Thr Lys Thr Glu
            20                  25                  30

Glu Gln Pro Gly Glu Lys Asp Gln Ala Val Ser Val Ser Phe Gly Asp
        35                  40                  45

Pro Gln Gly Ser Ala Leu Gln Asp Ala Ala Leu Gly Trp Gly Arg Arg
    50                  55                  60

Cys Pro Gln Cys Pro Arg Cys Pro Ser Cys Pro Ser Cys Pro Arg Cys
65                  70                  75                  80

Pro Arg Cys Pro Arg Cys Lys Cys Asn Pro Lys
                85                  90

<210> SEQ ID NO 62
<211> LENGTH: 40
<212> TYPE: PRT
<213> ORGANISM: Bos taurus

<400> SEQUENCE: 62

Gln Gly Val Arg Asn Phe Val Thr Cys Arg Ile Asn Arg Gly Phe Cys
1               5                   10                  15

Val Pro Ile Arg Cys Pro Gly His Arg Arg Gln Ile Gly Thr Cys Leu
            20                  25                  30

Gly Pro Gln Ile Lys Cys Cys Arg
        35                  40

<210> SEQ ID NO 63
<211> LENGTH: 40
<212> TYPE: PRT
<213> ORGANISM: Bos taurus

<400> SEQUENCE: 63

Gln Gly Val Arg Asn Phe Val Thr Cys Arg Ile Asn Arg Gly Phe Cys
1               5                   10                  15

Val Pro Ile Arg Cys Pro Gly His Arg Arg Gln Ile Gly Thr Cys Leu
            20                  25                  30

Gly Pro Arg Ile Lys Cys Cys Arg
```

<210> SEQ ID NO 64
<211> LENGTH: 42
<212> TYPE: PRT
<213> ORGANISM: Bos taurus

<400> SEQUENCE: 64

Gln Gly Val Arg Asn His Val Thr Cys Arg Ile Tyr Gly Gly Phe Cys
1               5                   10                  15

Val Pro Ile Arg Cys Pro Gly Arg Thr Arg Gln Ile Gly Thr Cys Phe
            20                  25                  30

Gly Arg Pro Val Lys Cys Cys Arg Arg Trp
        35                  40

<210> SEQ ID NO 65
<211> LENGTH: 40
<212> TYPE: PRT
<213> ORGANISM: Bos taurus

<400> SEQUENCE: 65

Gln Val Val Arg Asn Pro Gln Ser Cys Arg Trp Asn Met Gly Val Cys
1               5                   10                  15

Ile Pro Ile Ser Cys Pro Gly Asn Met Arg Gln Ile Gly Thr Cys Phe
            20                  25                  30

Gly Pro Arg Val Pro Cys Cys Arg
        35                  40

<210> SEQ ID NO 66
<211> LENGTH: 41
<212> TYPE: PRT
<213> ORGANISM: Bos taurus

<400> SEQUENCE: 66

Gln Arg Val Arg Asn Pro Gln Ser Cys Arg Trp Asn Met Gly Val Cys
1               5                   10                  15

Ile Pro Phe Leu Cys Arg Val Gly Met Arg Gln Ile Gly Thr Cys Phe
            20                  25                  30

Gly Pro Arg Val Pro Cys Cys Arg Arg
        35                  40

<210> SEQ ID NO 67
<211> LENGTH: 42
<212> TYPE: PRT
<213> ORGANISM: Bos taurus

<400> SEQUENCE: 67

Gln Gly Val Arg Asn His Val Thr Cys Arg Ile Asn Arg Gly Phe Cys
1               5                   10                  15

Val Pro Ile Arg Cys Pro Gly Arg Thr Arg Gln Ile Gly Thr Cys Phe
            20                  25                  30

Gly Pro Arg Ile Lys Cys Cys Arg Ser Trp
        35                  40

<210> SEQ ID NO 68
<211> LENGTH: 40
<212> TYPE: PRT
<213> ORGANISM: Bos taurus

<400> SEQUENCE: 68

Gln Gly Val Arg Ser Tyr Leu Ser Cys Trp Gly Asn Arg Gly Ile Cys

-continued

```
                1               5                  10                 15
Leu Leu Asn Arg Cys Pro Gly Arg Met Arg Gln Ile Gly Thr Cys Leu
                    20                 25                 30

Ala Pro Arg Val Lys Cys Cys Arg
            35                 40

<210> SEQ ID NO 69
<211> LENGTH: 42
<212> TYPE: PRT
<213> ORGANISM: Bos taurus

<400> SEQUENCE: 69

Ser Gly Ile Ser Gly Pro Leu Ser Cys Gly Arg Asn Gly Gly Val Cys
1               5                  10                 15

Ile Pro Ile Arg Cys Pro Val Pro Met Arg Gln Ile Gly Thr Cys Phe
                    20                 25                 30

Gly Arg Pro Val Lys Cys Cys Arg Ser Trp
            35                 40

<210> SEQ ID NO 70
<211> LENGTH: 38
<212> TYPE: PRT
<213> ORGANISM: Bos taurus

<400> SEQUENCE: 70

Asp Phe Ala Ser Cys His Thr Asn Gly Gly Ile Cys Leu Pro Asn Arg
1               5                  10                 15

Cys Pro Gly His Met Ile Gln Ile Gly Ile Cys Phe Arg Pro Arg Val
                    20                 25                 30

Lys Cys Cys Arg Ser Trp
            35

<210> SEQ ID NO 71
<211> LENGTH: 74
<212> TYPE: PRT
<213> ORGANISM: Zophobas atratus

<400> SEQUENCE: 71

Ser Leu Gln Gly Gly Ala Pro Asn Phe Pro Gln Pro Ser Gln Gln Asn
1               5                  10                 15

Gly Gly Trp Gln Val Ser Pro Asp Leu Gly Arg Asp Asp Lys Gly Asn
                    20                 25                 30

Thr Arg Gly Gln Ile Glu Ile Gln Asn Lys Gly Lys Asp His Asp Phe
            35                 40                 45

Asn Ala Gly Trp Gly Lys Val Ile Arg Gly Pro Asn Lys Ala Lys Pro
    50                 55                 60

Thr Trp His Val Gly Gly Thr Tyr Arg Arg
65                  70

<210> SEQ ID NO 72
<211> LENGTH: 67
<212> TYPE: PRT
<213> ORGANISM: Homo sapiens

<400> SEQUENCE: 72

Met Arg Ile His Tyr Leu Leu Phe Ala Leu Leu Phe Leu Phe Leu Val
1               5                  10                 15

Pro Val Pro Gly His Gly Gly Ile Ile Asn Thr Leu Gln Lys Tyr Tyr
                    20                 25                 30
```

```
Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 73
<211> LENGTH: 40
<212> TYPE: PRT
<213> ORGANISM: Aedes aegypti

<400> SEQUENCE: 73

Ala Thr Cys Asp Leu Leu Ser Gly Phe Gly Val Gly Asp Ser Ala Cys
1               5                   10                  15

Ala Ala His Cys Ile Ala Arg Gly Asn Arg Gly Gly Tyr Cys Asn Ser
            20                  25                  30

Lys Lys Val Cys Val Cys Arg Asn
        35                  40

<210> SEQ ID NO 74
<211> LENGTH: 35
<212> TYPE: PRT
<213> ORGANISM: Mytilus edulis
<220> FEATURE:
<221> NAME/KEY: misc_feature
<222> LOCATION: (28)..(28)
<223> OTHER INFORMATION: Xaa can be any naturally occurring amino acid

<400> SEQUENCE: 74

Gly Phe Gly Cys Pro Asn Asp Tyr Pro Cys His Arg His Cys Lys Ser
1               5                   10                  15

Ile Pro Gly Arg Tyr Gly Gly Tyr Cys Gly Gly Xaa His Arg Leu Arg
            20                  25                  30

Cys Thr Cys
        35

<210> SEQ ID NO 75
<211> LENGTH: 40
<212> TYPE: PRT
<213> ORGANISM: Sarcophaga peregrina

<400> SEQUENCE: 75

Ala Thr Cys Asp Leu Leu Ser Gly Ile Gly Val Gln His Ser Ala Cys
1               5                   10                  15

Ala Leu His Cys Val Phe Arg Gly Asn Arg Gly Gly Tyr Cys Thr Gly
            20                  25                  30

Lys Gly Ile Cys Val Cys Arg Asn
        35                  40

<210> SEQ ID NO 76
<211> LENGTH: 95
<212> TYPE: PRT
<213> ORGANISM: Oryctolagus cuniculus

<400> SEQUENCE: 76

Met Arg Thr Leu Ala Leu Leu Ala Ala Ile Leu Leu Val Ala Leu Gln
1               5                   10                  15

Ala Gln Ala Glu His Val Ser Val Ser Ile Asp Glu Val Val Asp Gln
            20                  25                  30

Gln Pro Pro Gln Ala Glu Asp Gln Asp Val Ala Ile Tyr Val Lys Glu
```

```
                35                  40                  45
His Glu Ser Ser Ala Leu Glu Ala Leu Gly Val Lys Ala Gly Val Val
        50                  55                  60
Cys Ala Cys Arg Arg Ala Leu Cys Leu Pro Arg Glu Arg Arg Ala Gly
65                  70                  75                  80
Phe Cys Arg Ile Arg Gly Arg Ile His Pro Leu Cys Cys Arg Arg
                85                  90                  95

<210> SEQ ID NO 77
<211> LENGTH: 92
<212> TYPE: PRT
<213> ORGANISM: Mus musculus

<400> SEQUENCE: 77

Met Lys Pro Leu Val Leu Leu Ser Ala Leu Val Leu Leu Ser Phe Gln
1               5                   10                  15
Val Gln Ala Asp Pro Ile Gln Asn Thr Asp Glu Glu Thr Lys Thr Glu
                20                  25                  30
Glu Gln Ser Gly Glu Glu Asp Gln Ala Val Ser Val Ser Phe Gly Asp
            35                  40                  45
Arg Glu Gly Ala Ser Leu Gln Glu Ser Leu Arg Asp Leu Val Cys
        50                  55                  60
Tyr Cys Arg Thr Arg Gly Cys Lys Arg Arg Glu Arg Met Asn Gly Thr
65                  70                  75                  80
Cys Arg Lys Gly His Leu Met Tyr Thr Leu Cys Cys
                85                  90

<210> SEQ ID NO 78
<211> LENGTH: 93
<212> TYPE: PRT
<213> ORGANISM: Mus musculus

<400> SEQUENCE: 78

Met Lys Thr Phe Val Leu Leu Ser Ala Leu Val Leu Leu Ala Phe Gln
1               5                   10                  15
Val Gln Ala Asp Pro Ile His Lys Thr Asp Glu Glu Thr Asn Thr Glu
                20                  25                  30
Glu Gln Pro Gly Glu Glu Asp Gln Ala Val Ser Ile Ser Phe Gly Gly
            35                  40                  45
Gln Glu Gly Ser Ala Leu His Glu Glu Leu Ser Lys Lys Leu Ile Cys
        50                  55                  60
Tyr Cys Arg Ile Arg Gly Cys Lys Arg Arg Glu Arg Val Phe Gly Thr
65                  70                  75                  80
Cys Arg Asn Leu Phe Leu Thr Phe Val Phe Cys Cys Ser
                85                  90

<210> SEQ ID NO 79
<211> LENGTH: 35
<212> TYPE: PRT
<213> ORGANISM: Mus musculus

<400> SEQUENCE: 79

Leu Arg Asp Leu Val Cys Tyr Cys Arg Ala Arg Gly Cys Lys Gly Arg
1               5                   10                  15
Glu Arg Met Asn Gly Thr Cys Arg Lys Gly His Leu Leu Tyr Met Leu
                20                  25                  30
Cys Cys Arg
        35
```

-continued

<210> SEQ ID NO 80
<211> LENGTH: 43
<212> TYPE: PRT
<213> ORGANISM: Pyrrhocoris apterus

<400> SEQUENCE: 80

Ala Thr Cys Asp Ile Leu Ser Phe Gln Ser Gln Trp Val Thr Pro Asn
1               5                   10                  15

His Ala Gly Cys Ala Leu His Cys Val Ile Lys Gly Tyr Lys Gly Gly
            20                  25                  30

Gln Cys Lys Ile Thr Val Cys His Cys Arg Arg
        35                  40

<210> SEQ ID NO 81
<211> LENGTH: 32
<212> TYPE: PRT
<213> ORGANISM: Rattus norvegicus

<400> SEQUENCE: 81

Val Thr Cys Tyr Cys Arg Ser Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 82
<211> LENGTH: 31
<212> TYPE: PRT
<213> ORGANISM: Rattus norvegicus

<400> SEQUENCE: 82

Val Thr Cys Ser Cys Arg Thr Ser Ser Cys Arg Phe Gly Glu Arg Leu
1               5                   10                  15

Ser Gly Ala Cys Arg Leu Asn Gly Arg Ile Tyr Arg Leu Cys Cys
            20                  25                  30

<210> SEQ ID NO 83
<211> LENGTH: 34
<212> TYPE: PRT
<213> ORGANISM: Oryctolagus cuniculus

<400> SEQUENCE: 83

Gly Ile Cys Ala Cys Arg Arg Arg Phe Cys Leu Asn Phe Glu Gln Phe
1               5                   10                  15

Ser Gly Tyr Cys Arg Val Asn Gly Ala Arg Tyr Val Arg Cys Cys Ser
            20                  25                  30

Arg Arg

<210> SEQ ID NO 84
<211> LENGTH: 64
<212> TYPE: PRT
<213> ORGANISM: Pan troglodytes

<400> SEQUENCE: 84

Met Arg Val Leu Tyr Leu Leu Phe Ser Phe Leu Phe Ile Phe Leu Met
1               5                   10                  15

Pro Leu Pro Gly Val Phe Gly Gly Ile Ser Asp Pro Val Thr Cys Leu
            20                  25                  30

Lys Ser Gly Ala Ile Cys His Pro Val Phe Cys Pro Arg Arg Tyr Lys
        35                  40                  45

```
Gln Ile Gly Thr Cys Gly Leu Pro Gly Thr Lys Cys Cys Lys Lys Pro
    50                  55                  60
```

<210> SEQ ID NO 85
<211> LENGTH: 64
<212> TYPE: PRT
<213> ORGANISM: Homo sapiens

<400> SEQUENCE: 85

```
Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60
```

<210> SEQ ID NO 86
<211> LENGTH: 68
<212> TYPE: PRT
<213> ORGANISM: Homo sapiens

<400> SEQUENCE: 86

```
Met Arg Thr Ser Tyr Leu Leu Phe Thr Leu Cys Leu Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65
```

<210> SEQ ID NO 87
<211> LENGTH: 64
<212> TYPE: PRT
<213> ORGANISM: Capra hircus

<400> SEQUENCE: 87

```
Met Arg Leu His His Leu Leu Leu Val Leu Phe Phe Leu Val Leu Ser
1               5                   10                  15

Ala Gly Ser Gly Phe Thr Gln Gly Ile Arg Ser Arg Arg Ser Cys His
            20                  25                  30

Arg Asn Lys Gly Val Cys Ala Leu Thr Arg Cys Pro Arg Asn Met Arg
        35                  40                  45

Gln Ile Gly Thr Cys Phe Gly Pro Pro Val Lys Cys Cys Arg Lys Lys
    50                  55                  60
```

<210> SEQ ID NO 88
<211> LENGTH: 64
<212> TYPE: PRT
<213> ORGANISM: Capra hircus

<400> SEQUENCE: 88

```
Met Arg Leu His His Leu Leu Leu Ala Leu Phe Phe Leu Val Leu Ser
1               5                   10                  15

Ala Gly Ser Gly Phe Thr Gln Gly Ile Ile Asn His Arg Ser Cys Tyr
            20                  25                  30
```

```
Arg Asn Lys Gly Val Cys Ala Pro Ala Arg Cys Pro Arg Asn Met Arg
            35                  40                  45

Gln Ile Gly Thr Cys His Gly Pro Pro Val Lys Cys Cys Arg Lys Lys
     50                  55                  60
```

<210> SEQ ID NO 89
<211> LENGTH: 96
<212> TYPE: PRT
<213> ORGANISM: Macaca mulatta

<400> SEQUENCE: 89

```
Met Arg Thr Leu Val Ile Leu Ala Ala Ile Leu Leu Val Ala Leu Gln
 1               5                  10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Val Ser Leu Ala
        35                  40                  45

Trp Asp Glu Ser Leu Ala Pro Lys Asp Ser Val Pro Gly Leu Arg Lys
    50                  55                  60

Asn Met Ala Cys Tyr Cys Arg Ile Pro Ala Cys Leu Ala Gly Glu Arg
65                  70                  75                  80

Arg Tyr Gly Thr Cys Phe Tyr Arg Arg Arg Val Trp Ala Phe Cys Cys
                85                  90                  95
```

<210> SEQ ID NO 90
<211> LENGTH: 96
<212> TYPE: PRT
<213> ORGANISM: Macaca mulatta

<400> SEQUENCE: 90

```
Met Arg Thr Leu Val Ile Leu Ala Ala Ile Leu Leu Val Ala Leu Gln
 1               5                  10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Val Ser Leu Ala
        35                  40                  45

Trp Asp Glu Ser Leu Ala Pro Lys Asp Ser Val Pro Gly Leu Arg Lys
    50                  55                  60

Asn Met Ala Cys Tyr Cys Arg Ile Pro Ala Cys Leu Ala Gly Glu Arg
65                  70                  75                  80

Arg Tyr Gly Thr Cys Phe Tyr Leu Gly Arg Val Trp Ala Phe Cys Cys
                85                  90                  95
```

<210> SEQ ID NO 91
<211> LENGTH: 33
<212> TYPE: PRT
<213> ORGANISM: Mesocricetus auratus

<400> SEQUENCE: 91

```
Val Thr Cys Phe Cys Arg Arg Arg Gly Cys Ala Ser Arg Glu Arg His
 1               5                  10                  15

Ile Gly Tyr Cys Arg Phe Gly Asn Thr Ile Tyr Arg Leu Cys Cys Arg
                20                  25                  30

Arg
```

<210> SEQ ID NO 92
<211> LENGTH: 31
<212> TYPE: PRT

<213> ORGANISM: Mesocricetus auratus

<400> SEQUENCE: 92

Cys Phe Cys Lys Arg Pro Val Cys Asp Ser Gly Glu Thr Gln Ile Gly
1               5                   10                  15

Tyr Cys Arg Leu Gly Asn Thr Phe Tyr Arg Leu Cys Cys Arg Gln
            20                  25                  30

<210> SEQ ID NO 93
<211> LENGTH: 39
<212> TYPE: PRT
<213> ORGANISM: Gallus gallus

<400> SEQUENCE: 93

Gly Arg Lys Ser Asp Cys Phe Arg Lys Asn Gly Phe Cys Ala Phe Leu
1               5                   10                  15

Lys Cys Pro Tyr Leu Thr Leu Ile Ser Gly Lys Cys Ser Arg Phe His
            20                  25                  30

Leu Cys Cys Lys Arg Ile Trp
        35

<210> SEQ ID NO 94
<211> LENGTH: 43
<212> TYPE: PRT
<213> ORGANISM: Allomyrina dichotoma

<400> SEQUENCE: 94

Val Thr Cys Asp Leu Leu Ser Phe Glu Ala Lys Gly Phe Ala Ala Asn
1               5                   10                  15

His Ser Leu Cys Ala Ala His Cys Leu Ala Ile Gly Arg Arg Gly Gly
            20                  25                  30

Ser Cys Glu Arg Gly Val Cys Ile Cys Arg Arg
        35                  40

<210> SEQ ID NO 95
<211> LENGTH: 31
<212> TYPE: PRT
<213> ORGANISM: Cavia porcellus

<400> SEQUENCE: 95

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 96
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The residue at this position may represent
      conservatively or nonconservatively substituted amino acids and
      may be present orabsent, or equal from 1-2.
<220> FEATURE:
<221> NAME/KEY: MISC_FEATURE
<222> LOCATION: (3)..(3)
<223> OTHER INFORMATION: The residue at this position may represent a
      conservatively or nonconservatively substituted amino acid.
<220> FEATURE:
<221> NAME/KEY: MISC_FEATURE
<222> LOCATION: (6)..(6)

```
<223> OTHER INFORMATION: The residue at this position may represent
      three or four conservatively or nonconservatively substituted
      amino acids.
<220> FEATURE:
<221> NAME/KEY: MISC_FEATURE
<222> LOCATION: (8)..(8)
<223> OTHER INFORMATION: The residue at this position may represent
      three or four conservatively or nonconservatively substituted
      amino acids.
<220> FEATURE:
<221> NAME/KEY: MISC_FEATURE
<222> LOCATION: (11)..(11)
<223> OTHER INFORMATION: The residue at this position may represent one,
      two, or three conservatively or nonconservatively substituted
      amino acids.
<220> FEATURE:
<221> NAME/KEY: MISC_FEATURE
<222> LOCATION: (13)..(13)
<220> FEATURE:
<221> NAME/KEY: MISC_FEATURE
<222> LOCATION: (15)..(15)
<223> OTHER INFORMATION: The residue at this position may represent five
      to nine consecutively or nonconservatively substituted amino acids.
<220> FEATURE:
<221> NAME/KEY: MISC_FEATURE
<222> LOCATION: (18)..(18)
<223> OTHER INFORMATION: The residue at this position may represent
      conservatively or nonconservatively substituted amino acids and
      may be present or absent, or equal from 1-2.

<400> SEQUENCE: 96

Xaa Cys Xaa Cys Arg Xaa Cys Xaa Glu Arg Xaa Cys Xaa Gly Xaa Cys
1               5                   10                  15

Cys Xaa

<210> SEQ ID NO 97
<211> LENGTH: 2540
<212> TYPE: DNA
<213> ORGANISM: Homo sapiens

<400> SEQUENCE: 97
tccggtcgac ctatggctat tggccaggtt caatactatg tattggccct atgccatata      60
gtattccata tatgggtttt cctattgacg tagatagccc ctcccaatgg gcggtcccat     120
ataccatata tggggcttcc taataccgcc catagccact cccccattga cgtcaatggt     180
ctctatatat ggtctttcct attgacgtca tatgggcggt cctattgacg tatatggcgc     240
ctcccccatt gacgtcaatt acggtaaatg gcccgcctgg ctcaatgccc attgacgtca     300
ataggaccac ccaccattga cgtcaatggg atggctcatt gcccattcat atccgttctc     360
acgcccccta ttgacgtcaa tgacggtaaa tgcccacctt ggcagtacat caatatctat     420
taatagtaac ttggcaagta cattactatt ggaagtacgc cagggtacat ggcagtact     480 cccattgacg tcaatggcgg taaatggccc gcgatggctg ccaagtacat ccccattgac     540
gtcaatgggg aggggcaatg acgcaaatgg gcgttccatt gacgtaaatg ggcggtaggc     600
gtgcctaatg ggaggtctat ataagcaatg ctcgtttagg aaccgccat tctgcctggg      660 gacgtcggag gagctcgaat ggagcgcgcg tcctgcttgt tgctgctgct gctgccgctg     720
gtgcacgtct ctgcgaccac gccagaacct tgtgagctgg acgatgaaga tttccgctgc     780
gtctgcaact ctccgaacc tcagcccgac tggtccgaag ccttccagtg tgtgtctgca     840
gtagaggtgg agatccatgc cggcggtctc aacctagagc cgtttctaaa gcgcgtcgat     900
gcggacgccg acccgcggca gtatgctgac acgtcaagg ctctccgcgt cggcggctc      960 acagtgggag ccgcacaggt tcctgctcag ctactggtag gcgccctgcg tgtgctagcg    1020
```

```
tactcccgcc tcaaggaact gacgctcgag gacctaaaga taaccggcac catgcctccg    1080
ctgcctctgg aagccacagg acttgcactt tccagcttgc gcctacgcaa cgtgtcgtgg    1140
gcgacagggc gttcttggct cgccgagctg cagcagtggc tcaagccagg cctcaaggta    1200
ctgagcattg cccaagcaca ctcgcctgcc ttttcctgcg aacaggttcg cgccttcccg    1260
gcccttacca gcctagacct gtctgacaat cctggactgg gcgaacgcgg actgatggcg    1320
gctctctgtc cccacaagtt cccggccatc agaatctag cgctgcgcaa cacaggaatg    1380
gagacgccca caggcgtgtg cgccgcactg gcggcggcag gtgtgcagcc ccacagccta    1440
gacctcagcc acaactcgct gcgcgccacc gtaaacccta cgctccgag atgcatgtgg    1500 tccagcgccc tgaactccct caatctgtcg ttcgctgggc tggaacaggt gcctaaagga    1560
ctgccagcca agctcagagt gctcgatctc agctgcaaca gactgaacag ggcgccgcag    1620
cctgacgagc tgcccgaggt ggataacctg acactggacg ggaatcccctt cctggtccct    1680 ggaactgccc tcccccacga gggctcaatg aactccggcg tggtcccagc ctgtgcacgt    1740
tcgaccctgt cggtggggt gtcgggaacc ctggtgctgc tccaaggggc ccggggcttt    1800
gccggtggag gcggttcagg cggaggtggc tctggcggtg gcggatcgaa gaccctccta    1860
ctgttggcag tgatcatgat ctttggccta ctgcaggccc atgggaattt ggtgaatttc    1920
cacagaatga tcaagttgac gacaggaaag gaagccgcac tcagttatgg cttctacggc    1980
tgccactgtg gcgtgggtgg cagaggatcc cccaaggatg caacggatcg ctgctgtgtc    2040
actcatgact gttgctacaa acgtctggag aaacgtggat gtggcaccaa atttctgagc    2100
tacaagttta gcaactcggg gagcagaatc acctgtgcaa acaggactc ctgcagaagt    2160 caactgtgtg agtgtgataa ggctgctgcc acctgttttg ctagaaacaa gacgacctac    2220
aataaaaagt accagtacta ttccaataaa cactgcagag ggagcacccc tcgttgctga    2280
gtcccctctt ccctggaaac cttccaccca gtgctgaatt ccctctctc ataccctccc    2340 tccctaccct aaccaagttc cttggccatg cagaaagcat ccctcaccca tcctagaggc    2400
caggcaggag cccttctata cccacccaga atgagacatc cagcagattt ccagccttct    2460
actgctctcc tccacctcaa ctccgtgctt aaccaaagaa gctgtactcc gggggggtctc    2520 ttctgaataa agcaattagc                                                 2540
```

<210> SEQ ID NO 98
<211> LENGTH: 2003
<212> TYPE: DNA
<213> ORGANISM: Homo sapiens

<400> SEQUENCE: 98

```
tccggtcgac ctatggctat tggccaggtt caatactatg tattggccct atgccatata     60
gtattccata tatgggtttt cctattgacg tagatagccc ctcccaatgg gcggtcccat    120
ataccatata tggggcttcc taataccgcc catagccact cccccattga cgtcaatggt    180
ctctatatat ggtctttcct attgacgtca tatgggcggt cctattgacg tatatggcgc    240
ctcccccatt gacgtcaatt acggtaaatg gcccgcctgg ctcaatgccc attgacgtca    300
ataggaccac ccaccattga cgtcaatggg atggctcatt gcccattcat atccgttctc    360
acgcccccta ttgacgtcaa tgacggtaaa tgggcacctt ggcagtacat caatatctat    420
taatagtaac ttggcaagta cattactatt ggaagtacgc cagggtacat tggcagtact    480
cccattgacg tcaatggcgg taatggccc gcgatggctg ccaagtacat ccccattgac    540
gtcaatgggg agggcaatg acgcaaatgg gcgttccatt gacgtaaatg gcggtaggc    600
```

```
gtgcctaatg ggaggtctat ataagcaatg ctcgtttagg gaaccgccat tctgcctggg      660
gacgtcggag gagctcgaat gggggccttg gcaagagccc tgccgtccat actgctggca      720
ttgctgctta cgtccacccc agaggctctg ggtgccaacc ccggcttggt cgccaggatc      780
accgacaagg gactgcagta tgcggcccag gaggggctat tggctctgca gagtgagctg      840
ctcaggatca cgctgcctga cttcaccggg gacttgagga tccccacgt cggccgtggg       900 cgctatgagt tccacagcct gaacatccac agctgtgagc tgcttcactc tgcgctgagg      960
cctgtccccg gccagggcct gagtctcagc atctccgact cctccatccg ggtccagggc     1020
aggtggaagg tgcgcaagtc attcttcaaa ctacagggct cctttgatgt cagtgtcaag     1080
ggcatcagca tttcggtcaa cctcctgttg ggcagcgagt cctccgggag gcccacaggt     1140
tactgcctca gctgcagcag tgacatcgct gacgtggagg tggacatgtc gggagattcg     1200
gggtggctct tgaacctctt ccacaaccag attgagtcca agttccagaa agtactggag     1260 agcagggggtg gaggcggttc aggcggaggt ggctctggcg gtggcggatc gaagaccctc    1320
ctactgttgg cagtgatcat gatctttggc ctactgcagg cccatgggaa tttggtgaat     1380
ttccacagaa tgatcaagtt gacgacagga aaggaagccg cactcagtta tggcttctac     1440
ggctgccact gtggcgtggg tggcagagga tcccccaagg atgcaacgga tcgctgctgt    1500
gtcactcatg actgttgcta caaacgtctg gagaaacgtg gatgtggcac caaatttctg     1560
agctacaagt ttagcaactc ggggagcaga atcacctgtg caaaacagga ctcctgcaga     1620
agtcaactgt gtgagtgtga taaggctgct gccacctgtt ttgctagaaa caagacgacc     1680
tacaataaaa agtaccagta ctattccaat aaacactgca gagggagcac ccctcgttgc     1740
tgagtcccct cttccctgga aaccttccac ccagtgctga atttccctct ctcataccct     1800
ccctccctac cctaaccaag ttccttggcc atgcagaaag catccctcac ccatcctaga     1860
ggccaggcag gagcccttct atacccaccc agaatgagac atccagcaga tttccagcct     1920
tctactgctc tcctccacct caactccgtg cttaaccaaa gaagctgtac tccgggggt     1980 ctcttctgaa taaagcaatt agc                                             2003

<210> SEQ ID NO 99
<211> LENGTH: 2159
<212> TYPE: DNA
<213> ORGANISM: Homo sapiens

<400> SEQUENCE: 99
tccggtcgac ctatggctat tggccaggtt caatactatg tattggccct atgccatata       60
gtattccata tatgggtttt cctattgacg tagatagccc ctcccaatgg gcggtcccat      120
ataccatata tggggcttcc taataccgcc catagccact cccccattga cgtcaatggt      180
ctctatatat ggtctttcct attgacgtca tatggcggt cctattgacg tatatggcgc       240
ctcccccatt gacgtcaatt acggtaaatg gcccgcctgg ctcaatgccc attgacgtca      300
ataggaccac ccaccattga cgtcaatggg atggctcatt gcccattcat atccgttctc      360 acgccccta ttgacgtcaa tgacggtaaa tggcccactt ggcagtacat caatatctat       420
taatagtaac ttggcaagta cattactatt ggaagtacgc cagggtacat ggcagtact       480 cccattgacg tcaatggcgg taaatggccc gcgatgctg ccaagtacat ccccattgac       540
gtcaatgggg aggggcaatg acgcaaatgg gcgttccatt gacgtaaatg ggcggtaggc      600
gtgcctaatg ggaggtctat ataagcaatg ctcgtttagg gaaccgccat tctgcctggg      660
```

```
gacgtcggag gagctcgaat gtccctgttt ccatcactcc ctctccttct cctgagtatg    720
gtggcagcgt cttactcaga aactgtggcc tgtgaggatg cccaaaagac ctgccctgca    780
gtgattgcct gtagctctcc aggcatcaac ggcttccag gcaaagatgg gcgtgatggc    840
accaagggag aaaaggggga accaggccaa gggctcagag gcttacaggg ccccctgga    900 aagttgggc ctccaggaaa tccagggcct tctgggtcac caggaccaaa gggccaaaaa    960
ggagaccctg gaaaaagtcc ggatggtgat agtagcctgg ctgcctcaga agaaaagct   1020 ctgcaaacag aaatggcacg tatcaaaaag tggctgacct tctctctggg caaacaagtt   1080
gggaacaagt tcttcctgac caatggtgaa ataatgacct ttgaaaaagt gaaggccttg   1140
tgtgtcaagt ccaggcctc tgtggccacc cccaggaatg ctgcagagaa tggagccatt   1200
cagaatctca tcaaggagga agccttcctg ggtatcactg atgagaagac agaagggcag   1260
tttgtggatc tgacaggaaa tagactgacc tacacaaact ggaacgaggg tgaacccaac   1320
aatgctggtt ctgatgaaga ttgtgtattg ctactgaaaa atggccagtg gaatgacgtc   1380
ccctgctcca cctcccatct ggccgtctgt gagttcccta tcggtggagg cggttcaggc   1440
ggaggtggct ctggcggtgg cggatcgaag accctcctac tgttggcagt gatcatgatc   1500
tttggcctac tgcaggccca tgggaatttg gtgaatttcc acagaatgat caagttgacg   1560
acaggaaagg aagccgcact cagttatggc ttctacggct gccactgtgg cgtgggtggc   1620
agaggatccc ccaaggatgc aacggatcgc tgctgtgtca ctcatgactg ttgctacaaa   1680
cgtctggaga acgtggatg tggcaccaaa tttctgagct acaagtttag caactcgggg   1740
agcagaatca cctgtgcaaa acaggactcc tgcagaagtc aactgtgtga gtgtgataag   1800
gctgctgcca cctgttttgc tagaaacaag acgacctaca ataaaaagta ccagtactat   1860
tccaataaac actgcagagg gagcacccct cgttgctgag tcccctcttc cctggaaacc   1920
ttccacccag tgctgaattt ccctctctca taccctccct ccctacccta accaagttcc   1980
ttggccatgc agaaagcatc cctcacccat cctagaggcc aggcaggagc ccttctatac   2040
ccacccagaa tgagacatcc agcagatttc cagccttcta ctgctctcct ccacctcaac   2100
tccgtgctta accaaagaag ctgtactccg ggggtctct tctgaataaa gcaattagc    2159
```

<210> SEQ ID NO 100  
<211> LENGTH: 2540  
<212> TYPE: DNA  
<213> ORGANISM: Homo sapiens

<400> SEQUENCE: 100

```
tccggtcgac ctatggctat tggccaggtt caatactatg tattggccct atgccatata     60
gtattccata tatgggtttt cctattgacg tagatagccc ctcccaatgg gcggtcccat    120
ataccatata tggggcttcc taataccgcc catagccact cccccattga cgtcaatggt    180
ctctatatat ggtctttcct attgacgtca tatgggcggt cctattgacg tatatggcgc    240
ctcccccatt gacgtcaatt acggtaaatg gcccgcctgg ctcaatgccc attgacgtca    300
ataggaccac ccaccattga cgtcaatggg atggctcatt gcccattcat atccgttctc    360
acgcccccta ttgacgtcaa tgacggtaaa tggcccactt ggcagtacat caatatctat    420
taatagtaac ttggcaagta cattactatt ggaagtacgc cagggtacat ggcagtact     480 cccattgacg tcaatggcgg taatggccc gcgatggctg ccaagtacat ccccattgac    540
gtcaatgggg aggggcaatg acgcaaatgg gcgttccatt gacgtaaatg ggcggtaggc    600
```

-continued

```
gtgcctaatg ggaggtctat ataagcaatg ctcgtttagg gaaccgccat tctgcctggg      660
gacgtcggag gagctcgaat gctgctcttc ctcctctctg cactggtcct actcacacag      720
cccctgggct acctggaagc agaaatgaag acctactccc acagaacaac gcccagtgct      780
tgcaccctgg tcatgtgtag ctcagtggag agtggcctgc ctggtcgcga tggacgggat      840
gggagagagg gccctcgggg cgagaagggg gacccaggtt tgccaggagc tgcagggcaa      900
gcagggatgc ctggacaagc tggcccagtt gggcccaaag ggacaatggg ctctgttgga      960
gaacctggac caaagggaga cactgggcca agtggacctc caggacctcc cggtgtgcct     1020
ggtccagctg gaagagaagg tcccctgggg aagcagggga acataggacc tcagggcaag     1080
ccaggcccaa aggagaagc tgggcccaaa ggagaagtag gtgccccagg catgcagggc      1140
tcggcagggg caagaggcct cgcaggccct aagggagagc gaggtgtccc tggtgagcgt     1200
ggagtccctg gaaacgcagg ggcagcaggg tctgctggag ccatgggtcc cagggaagt     1260 ccaggtgcca ggggaccccc gggattgaag ggggacaaag gcattcctgg agacaaagga     1320
gcaaagggag aaagtgggct tccagatgtt gcttctctga ggcagcaggt tgaggcctta     1380
cagggacaag tacagcacct ccaggctgct ttctctcagt ataagaaagt tgagctcttc     1440
ccaaatggcc aaagtgtcgg ggagaagatt ttcaagacag caggctttgt aaaaccattt     1500
acggaggcac agctgctgtg cacacaggct ggtggacagt tggcctctcc acgtctgcc     1560 gctgagaatg ccgccttgca acagctggtc gtagctaaga acgaggctgc tttcctgagc     1620
atgactgatt ccaagacaga gggcaagttc acctacccca caggagagtc cctggtctat     1680
tccaactggg ccccaggga gcccaacgat gatggcgggt cagaggactg tgtggagatc     1740
ttcaccaatg gcaagtggaa tgacagggct tgtggagaaa agcgtcttgt ggtctgcgag     1800
ttcggtggag gcggttcagg cggaggtggc tctggcggtg gcggatcgaa gaccctccta     1860
ctgttggcag tgatcatgat ctttggccta ctgcaggccc atgggaattt ggtgaatttc     1920
cacagaatga tcaagttgac gacaggaaag gaagccgcac tcagttatgg cttctacggc     1980
tgccactgtg gcgtgggtgg cagaggatcc cccaaggatg caacgatcg ctgctgtgtc     2040 actcatgact gttgctacaa acgtctggag aaacgtggat gtggcaccaa atttctgagc     2100
tacaagttta gcaactcggg gagcagaatc cctgtgcaa acaggactc ctgcagaagt     2160 caactgtgtg agtgtgataa ggctgctgcc acctgttttg ctagaaacaa gacgacctac     2220
aataaaaagt accagtacta ttccaataaa cactgcagag ggagcacccc tcgttgctga     2280
gtcccctctt ccctggaaac cttccaccca gtgctgaatt ccctctctc atacctccc      2340 tccctaccct aaccaagttc cttggccatg cagaaagcat ccctcaccca tcctagaggc     2400
caggcaggag cccttctata cccacccaga atgagacatc cagcagattt ccagccttct     2460
actgctctcc tccacctcaa ctccgtgctt aaccaaagaa gctgtactcc gggggtctc     2520 ttctgaataa agcaattagc                                                 2540
```

<210> SEQ ID NO 101
<211> LENGTH: 5011
<212> TYPE: DNA
<213> ORGANISM: Mus musculus

<400> SEQUENCE: 101

```
tccggtcgac ctatggctat tggccaggtt caatactatg tattggccct atgccatata       60
gtattccata tatgggtttt cctattgacg tagatagccc ctcccaatgg gcggtcccat      120
ataccatata tggggcttcc taataccgcc catagccact cccccattga cgtcaatggt      180
```

```
ctctatatat ggtctttcct attgacgtca tatgggcggt cctattgacg tatatggcgc    240
ctcccccatt gacgtcaatt acggtaaatg gcccgcctgg ctcaatgccc attgacgtca    300
ataggaccac ccaccattga cgtcaatggg atggctcatt gcccattcat atccgttctc    360
acgcccccta ttgacgtcaa tgacggtaaa tggcccactt ggcagtacat caatatctat    420
taatagtaac ttggcaagta cattactatt ggaagtacgc cagggtacat ggcagtact     480
cccattgacg tcaatggcgg taaatggccc gcgatggctg ccaagtacat ccccattgac    540
gtcaatgggg aggggcaatg acgcaaatgg gcgttccatt gacgtaaatg gcggtaggc     600
gtgcctaatg ggaggtctat ataagcaatg ctcgtttagg aaccgccat tctgcctggg     660
gacgtcggag gagctcgaat ggctgtcctg gtgctgttcc tctgcctggt tgcatttcca    720
agctgtgtcc tgtcccaggt gcagctgaag gagtcaggac ctggcctggt ggcgccctca    780
cagagcctgt ccatcacttg cactgtctct gggttttcat taaccaacta tggtgtacat    840
tgggttcgcc agcctccagg aaagggtctg gagtggctgg gagtaatatg ggctggtgga    900
aacacaaatt ataattcggc ttttatgtcc agactgagca tcaccaaaga caactccaag    960
agccaagttt tcataaaaat gaacagtctg caaactgatg acacagccat gtactactgt   1020
gccagagaat ataggcacgg ggcttactat gctatggact actggggtca aggaacctca   1080
gtcaccgtct cctcagagag tcagtccttc ccaaatgtct tcccctcgt ctcctgcgag    1140
agcccctgt ctgataagaa tctggtggcc atgggctgcc tggcccggga cttcctgccc    1200
agcaccattt ccttcacctg gaactaccag aacaacactg aagtcatcca gggtatcaga   1260
accttcccaa cactgaggac aggggcaag tacctagcca cctcgcaggt gttgctgtct    1320
cccaagagca tccttgaagg ttcagatgaa tacctggtat gcaaaatcca ctacggaggc   1380
aaaaacagag atctgcatgt gcccattcca gctgtcgcag agatgaaccc caatgtaaat   1440
gtgttcgtcc caccacggga tggcttctct ggccctgcac cacgcaagtc taaactcatc   1500
tgcgaggcca cgaacttcac tccaaaaccg atcacagtat cctggctaaa ggatgggaag   1560
ctcgtggaat ctggcttcac cacagatccg gtgaccatcg agaacaaagg atccacaccc   1620
caaacctaca aggtcataag cacacttacc atctctgaaa tcgactggct gaacctgaat   1680
gtgtacacct gccgtgtgga tcacagggt ctcaccttct tgaagaacgt gtcctccaca    1740
tgtgctgcca gtccctccac agacatcctg accttcacca tcccccctc ctttgccgac    1800
atcttcctca gcaagtccgc taacctgacc tgtctggtct caaacctggc aacctatgaa   1860
accctgaata tctcctgggc ttctcaaagt ggtgaaccac tggaaaccaa aattaaaatc   1920
atggaaagcc atcccaatgg caccttcagt gctaagggtg tggctagtgt ttgtgtggaa   1980
gactggaata acaggaagga atttgtgtgt actgtgactc acagggatct gccttcacca   2040
cagaagaaat tcatctcaaa acccaatgag gtgcacaaac atccacctgc tgtgtacctg   2100
ctgccaccag ctcgtgagca actgaacctg agggagtcag ccacagtcac ctgcctggtg   2160
aagggcttct ctcctgcaga catcagtgtg cagtggcttc agagagggca actcttgccc   2220
caagagaagt atgtgaccag tgccccgatg ccagagcctg ggccccagg cttctacttt    2280
acccacagca tcctgactgt gacagaggag gaatggaact ccggagagac ctatacctgt   2340
gttgtaggcc acgaggccct gccacacctg gtgaccgaga ggaccgtgga caagtccact   2400
ggtaaaccca cactgtacaa tgtctccctg atcatgtctg acacaggcgg cacctgctat   2460
tgaaattcgc ccctctccct ccccccccc taacgttact ggccgaagcc gcttggaata   2520
```

```
aggccggtgt gcgtttgtct atatgttatt ttccaccata ttgccgtctt ttggcaatgt   2580
gagggcccgg aaacctggcc ctgtcttctt gacgagcatt cctagggtc tttcccctct    2640 cgccaaagga atgcaaggtc tgttgaatgt cgtgaaggaa gcagttcctc tggaagcttc   2700
ttgaagacaa acaacgtctg tagcgaccct ttgcaggcag cggaaccccc cacctggcga   2760
caggtgcctc tgcggccaaa agccacgtgt ataagataca cctgcaaagg cggcacaacc   2820
ccagtgccac gttgtgagtt ggatagttgt ggaaagagtc aaatggctct cctcaagcgt   2880
attcaacaag gggctgaagg atgcccagaa ggtaccccat tgtatgggat ctgatctggg   2940
gcctcggtgc acatgcttta catgtgttta gtcgaggtta aaaaaacgtc taggcccccc   3000
gaaccacggg gacgtggttt tcctttgaaa aacacgatga tggtggaggc ggttcaggcg   3060
gaggtggctc tggcggtggc ggatcgaaga ccctcctact gttggcagtg atcatgatct   3120
ttggcctact gcaggcccat gggaatttgg tgaatttcca cagaatgatc aagttgacga   3180
caggaaagga agccgcactc agttatggct tctacggctg ccactgtggc gtgggtggca   3240
gaggatcccc caaggatgca acggatcgct gctgtgtcac tcatgactgt tgctacaaac   3300
gtctggagaa acgtggatgt ggcaccaaat ttctgagcta caagtttagc aactcgggga   3360
gcagaatcac ctgtgcaaaa caggactcct gcagaagtca actgtgtgag tgtgataagg   3420
ctgctgccac ctgttttgct agaaacaaga cgacctacaa taaaaagtac cagtactatt   3480
ccaataaaca ctgcagaggg agcacccctc gttgctgaaa ttcgcccctc tccctccccc   3540 cccctaacg ttactggccg aagccgcttg gaataaggcc ggtgtgcgtt tgtctatatg    3600
ttattttcca ccatattgcc gtcttttggc aatgtgaggg cccggaaacc tggccctgtc   3660
ttcttgacga gcattcctag gggtctttcc cctctcgcca aggaatgca aggtctgttg    3720 aatgtcgtga aggaagcagt tcctctggaa gcttcttgaa gacaaacaac gtctgtagcg   3780 acccttgca ggcagcggaa ccccccacct ggcgacaggt gcctctgcgg ccaaaagcca    3840
cgtgtataag atacacctgc aaaggcggca acccccagt gccacgttgt gagttggata    3900
gttgtggaaa gagtcaaatg gctctcctca agcgtattca acaaggggct gaaggatgcc   3960
cagaaggtac cccattgtat gggatctgat ctggggcctc ggtgcacatg ctttacatgt   4020
gtttagtcga ggttaaaaaa acgtctaggc ccccgaacc acgggacgt ggttttcctt     4080 tgaaaaacac gatgataata tgagtgtcta ctcaggtcct gggggttgctg ctgctgtggc   4140 ttacaggtgc cagatgtgac atccagatga ctcagtctcc agcctcccta tctgcatctg   4200
tgggagaaac tgtcaccatc acatgtcgag caagtgagaa catttacagt tatttagcat   4260
ggtatcagca gaaacaggga aaatctcctc agttcctggt ctataatgca gaaaccttag   4320
cagaaggtgt gccatcaagg ttcagtggca gtggatcagg caaacagttt tctctgaaga   4380
tcaacagcct gcagcctgaa gattttggga gttattactg tcaacatcat tatggtactc   4440
atccgacgtt cggtggaggc accaagctgg aaatcaaacg ggctgatgct gcaccaactg   4500
tatccatctt cccaccatcc agtgagcagt taacatctgg aggtgcctca gtcgtgtgct   4560
tcttgaacaa cttctacccc aaagacatca atgtcaagtg gaagattgat ggcagtgaac   4620
gacaaaatgg cgtcctgaac agttggactg atcaggacag caaagacagc acctacagca   4680
tgagcagcac cctcacgttg accaaggacg agtatgaacg acataacagc tatcctgtg    4740 aggccactca caagacatca acttcaccca ttgtcaagag cttcaacagg aatgagtgtt   4800
agagacaaag gtcctgagac gccaccacca gctcccagc tccatcctat cttcccttct    4860
aaggtcttgg aggcttcccc acaagcgacc taccactgtt gcggtgctcc aaacctcctc   4920
```

```
cccacctcct tctcctcctc ctccctttcc ttggcttta tcatgctaat atttgcagaa    4980
aatattcaat aaagtgagtc tttgcacttg a                                 5011
```

<210> SEQ ID NO 102

<400> SEQUENCE: 102

000

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103

```
gcattgcatc agccatgatg                                              20
```

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104

```
gatggattgc acgcaggttc                                              20
```